US010597674B2

(12) United States Patent
Linka et al.

(10) Patent No.: US 10,597,674 B2
(45) Date of Patent: Mar. 24, 2020

(54) HPPD VARIANTS AND METHODS OF USE

(71) Applicant: BASF Agricultural Solutions Seed, US LLC, Research Triangle Park, NC (US)

(72) Inventors: Marc Linka, Düsseldorf (DE); Fabien Poree, Valbonne (FR); Bernd Laber, Idstein (DE); Gudrun Lange, Kelkheim (DE); Jan Tebbe, Köln (DE); Wayne Coco, Pulheim (DE); Michael Strerath, Düsseldorf (DE); Ernst Weber, Langenfeld (DE); Nikolaus Pawlowski, Köln (DE); Sandra Geske, Köln (DE); Heike Balven-Ross, Solingen (DE); Nina Wobst, Köln (DE); Christina Thies, Dormagen (DE); Manuel Dubald, Raleigh, NC (US)

(73) Assignee: BASF Agricultural Solutions Seed, US LLC, Florham Park, NJ (US)

( * ) Notice: Subject to any disclaimer, the term of this patent is extended or adjusted under 35 U.S.C. 154(b) by 0 days.

(21) Appl. No.: 15/758,429

(22) PCT Filed: Sep. 8, 2016

(86) PCT No.: PCT/EP2016/071159

§ 371 (c)(1),
(2) Date: Mar. 8, 2018

(87) PCT Pub. No.: WO2017/042259

PCT Pub. Date: Mar. 16, 2017

(65) Prior Publication Data

US 2018/0208937 A1 Jul. 26, 2018

(30) Foreign Application Priority Data

Sep. 11, 2015 (EP) .................................... 15184866

(51) Int. Cl.
*C12N 15/82* (2006.01)
*C12N 9/02* (2006.01)

(52) U.S. Cl.
CPC ....... *C12N 15/8274* (2013.01); *C12N 9/0069* (2013.01); *C12Y 113/11027* (2013.01)

(58) Field of Classification Search
CPC .................................................. C12N 15/8274
See application file for complete search history.

(56) References Cited

U.S. PATENT DOCUMENTS

| | | | | |
|---|---|---|---|---|
| 6,268,549 | B1 | 7/2001 | Sailland et al. | |
| 6,750,378 | B2 * | 6/2004 | Derose | C12N 15/8216 435/320.1 |
| 6,812,010 | B1 | 11/2004 | Derose et al. | |
| 8,847,017 | B2 | 9/2014 | Poree et al. | |
| 8,847,018 | B2 | 9/2014 | Poree et al. | |
| 8,853,495 | B2 | 10/2014 | Poree et al. | |
| 8,853,496 | B2 | 10/2014 | Poree et al. | |
| 8,859,856 | B2 | 10/2014 | Poree et al. | |
| 2005/0257283 | A1 | 11/2005 | Matringe et al. | |
| 2011/0039706 | A1 | 2/2011 | Busch et al. | |
| 2011/0173718 | A1 | 7/2011 | Hawkes et al. | |
| 2011/0185444 | A1 | 7/2011 | Li et al. | |
| 2011/0191897 | A1 | 8/2011 | Poree et al. | |
| 2011/0197307 | A1 | 8/2011 | Poree et al. | |
| 2011/0197308 | A1 | 8/2011 | Poree et al. | |
| 2011/0197309 | A1 | 8/2011 | Poree et al. | |
| 2011/0197310 | A1 | 8/2011 | Poree et al. | |
| 2012/0042413 | A1 | 2/2012 | Albert et al. | |
| 2014/0053295 | A1 | 2/2014 | Hawkes et al. | |
| 2014/0223597 | A1 | 8/2014 | Busch et al. | |
| 2015/0159145 | A1 | 6/2015 | Poree et al. | |
| 2015/0159167 | A1 | 6/2015 | Poree et al. | |
| 2015/0159168 | A1 | 6/2015 | Poree et al. | |

(Continued)

FOREIGN PATENT DOCUMENTS

| | | | |
|---|---|---|---|
| EP | 496630 | A1 | 7/1992 |
| EP | 2453012 | A1 | 5/2012 |

(Continued)

OTHER PUBLICATIONS

International Search Report of International Patent Application No. PCT/EP2016/071159 dated Nov. 14, 2016.

Crouch, et al., "A Mechanistic Rationalisation for the Substrate Specificity of Recombinant Mammalian 4-Hydroxyphenylpyruvate Dioxygenase (4-HPPD)." Tetrahedron, (1997), vol. 53, No. 20: 6993-7010.

(Continued)

*Primary Examiner* — Eileen B O Hara

(74) *Attorney, Agent, or Firm* — McBee Moore & Vanik IP, LLC

(57) ABSTRACT

In the present invention, HPPD polypeptides and plants containing them showing a full tolerance against one or more HPPD inhibitor herbicides belonging to various chemical classes are described. A set of mutant HPPD polypeptides have been designed which have either no or only a significantly reduced affinity to HPPD inhibitor herbicides and, at the same time, the rate of dissociation of the HPPD inhibitors of the mutant HPPD polypeptide is increased to such an extent that the HPPD inhibitors no longer act as slow-binding or slow, tight-binding inhibitors but, instead of this, have become fully reversible inhibitors. In particular, isolated polynucleotides encoding mutant HPPD polypeptides conferring tolerance to HPPD inhibitor herbicides belonging to various chemical classes are provided. Additionally, amino acid sequences corresponding to the polynucleotides are encompassed.

37 Claims, 7 Drawing Sheets

Specification includes a Sequence Listing.

(56) References Cited

U.S. PATENT DOCUMENTS

| | | | |
|---|---|---|---|
| 2015/0159169 A1 | 6/2015 | Poree et al. |
| 2015/0167016 A1 | 6/2015 | Poree et al. |

FOREIGN PATENT DOCUMENTS

| | | | |
|---|---|---|---|
| WO | 96/38567 | A2 | 12/1996 |
| WO | 99/24585 | A1 | 5/1999 |
| WO | 2002/046387 | A2 | 6/2002 |
| WO | 2004/024928 | A2 | 3/2004 |
| WO | 2006/132270 | A1 | 12/2006 |
| WO | 2008/150473 | A2 | 12/2008 |
| WO | 2009/144079 | A1 | 12/2009 |
| WO | 2010/085705 | A2 | 7/2010 |
| WO | 2011/068567 | A1 | 6/2011 |
| WO | 2011/076877 | A1 | 6/2011 |
| WO | 2011/076882 | A1 | 6/2011 |
| WO | 2011/076885 | A1 | 6/2011 |
| WO | 2011/076889 | A1 | 6/2011 |
| WO | 2011/076892 | A1 | 6/2011 |
| WO | 2011/094199 | A1 | 8/2011 |
| WO | 2011145015 | A1 | 11/2011 |
| WO | 2013/064964 | A1 | 5/2013 |
| WO | 2014/043435 | A1 | 3/2014 |
| WO | 2014/177999 | A2 | 11/2014 |
| WO | 2015/022634 | A2 | 2/2015 |

OTHER PUBLICATIONS

Fritze, et al., "The Crystal Structures of *Zea mays* and *Arabidopsis* 4-Hydroxyphenylpyruvate Dioxygenase," Plant Physiology, (2004), vol. 134:1388-1400.

Rüetschi, et al., "Characterization of 4-hydroxyphenylpyruvate dioxygenase, Primary structure of the Pseudomonas enzyme," Eur. J. Biochem., (1992), vol. 205: 459-466.

Matringe, et al., "p-Hydroxyphenylpyruvate dioxygenase inhibitor-resistant plants," Pest Management Science, (2005), vol. 61: 269-276.

Dufourmantel, et al., "Generation and characterization of soybean and marker-free tobacco plastid transformants over-expressing a bacterial 4-hydroxyphenylpyruvate dioxygenase which provides strong herbicide tolerance," Plant Biotechnol J., (2007), vol. 5: 118-133.

Morrison, John F., "The slow-binding and slow, tight-binding inhibition of enzyme-catalysed reactions," Trends Biochem. Sci., (1982), vol. 7: 102-105.

* cited by examiner

Figure 1: Simplistic scheme of the coupled HPPD activity assay
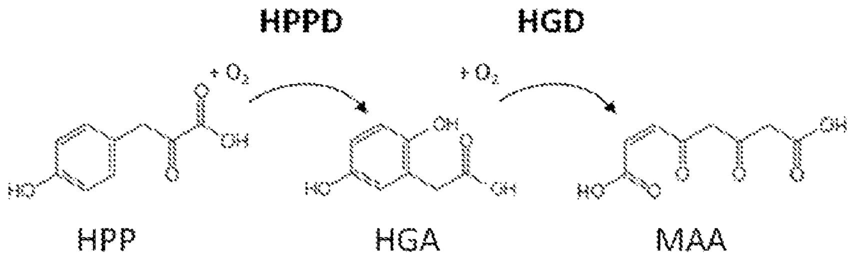

Figure 2: Kinetic changes in absorbance at 320 nm (Abs320) in raw extract samples of wild-type and knock-out HPPD polypetide observed with 200 μM HPP and 0 μM, 4 μM or 13 μM Cmpd. 1 in the coupled HPPD activity assay.
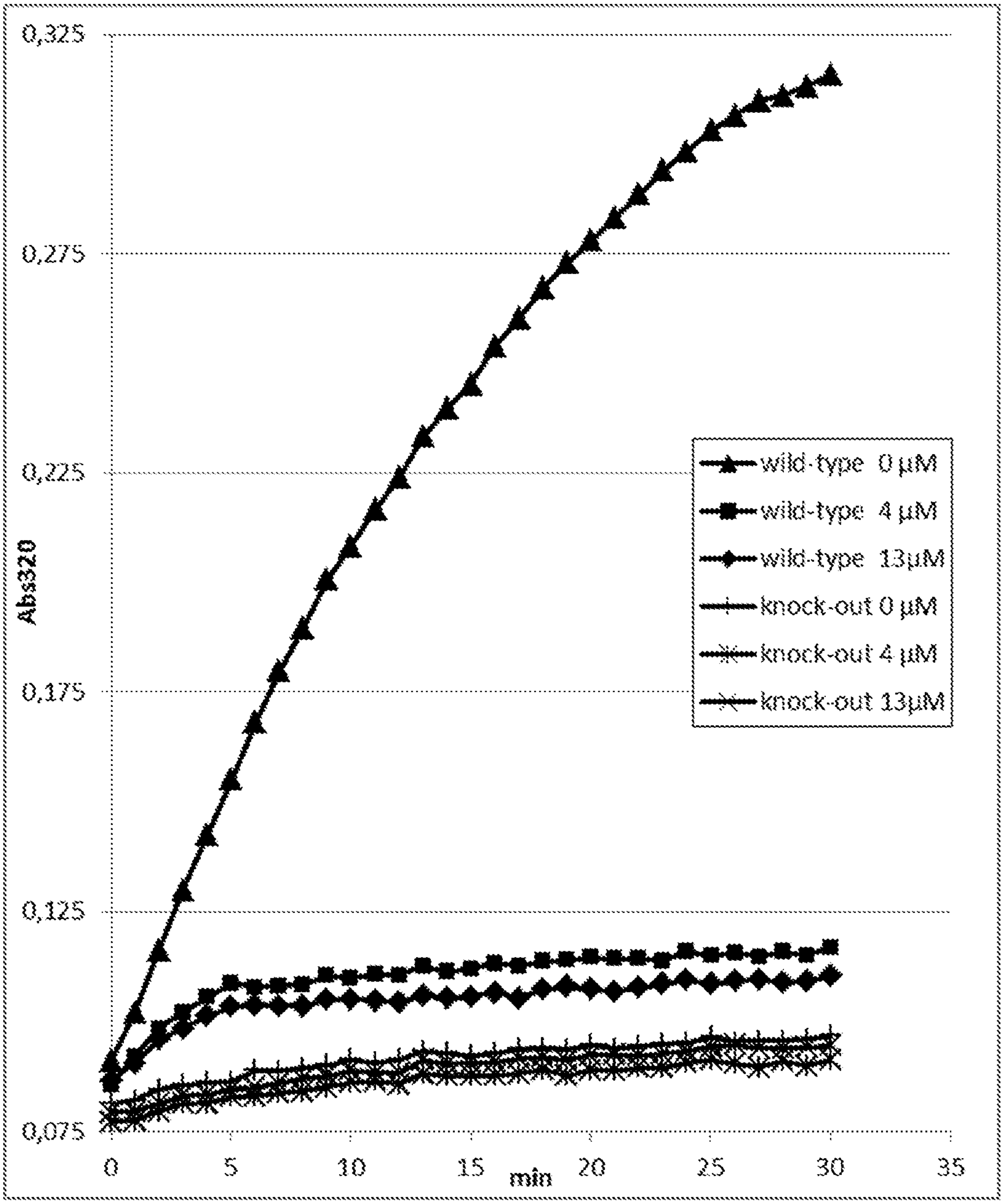

Figure 3: Kinetic changes in absorbance at 320 nm (Abs320) of a purified mutant HPPD polypeptide corresponding to SEQ ID NO:17 observed with 200 µM HPP and 0, 48, 240 or 1200 µM Cmpd. 2 in the coupled HPPD activity assay. The apparent kinetic constant ($k_{app}$) was determined as signal change over time in the boxed timeframe.
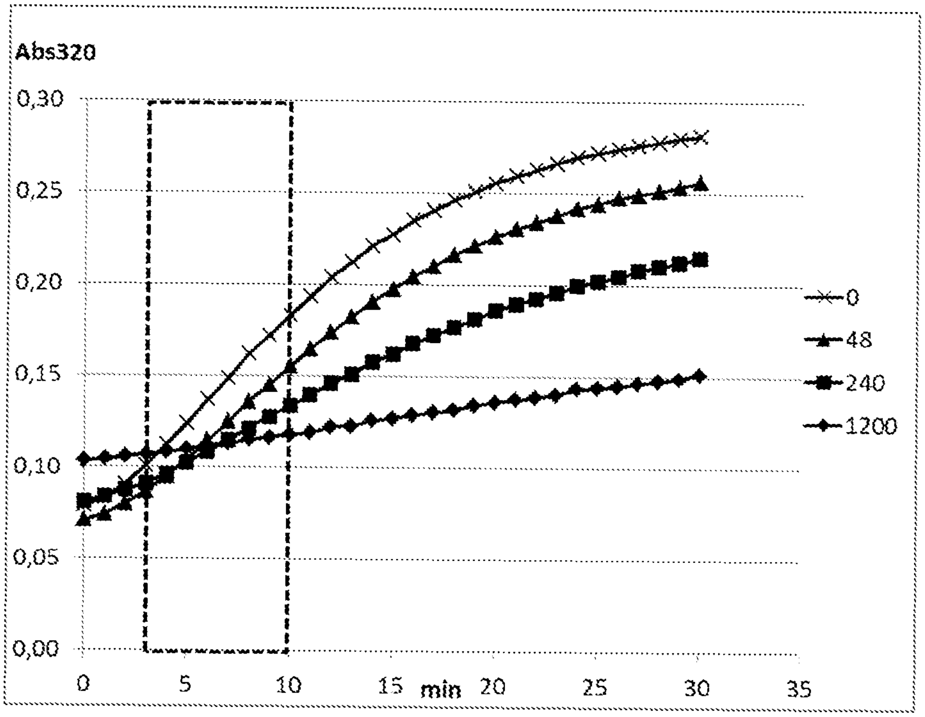

Figure 4: Exemplary ki determination with a purified mutant HPPD polypeptide corresponding to SEQ ID NO:17 with different inhibitor and substrate (HPP) concentrations by fitting according to the competitive inhibition model.
a) Kinetic changes in absorbance at 320 nm over time (delta_Abs320/min) in the presence of 0 – 0.0012 M of Cmpd. 2 at the given substrate concentration
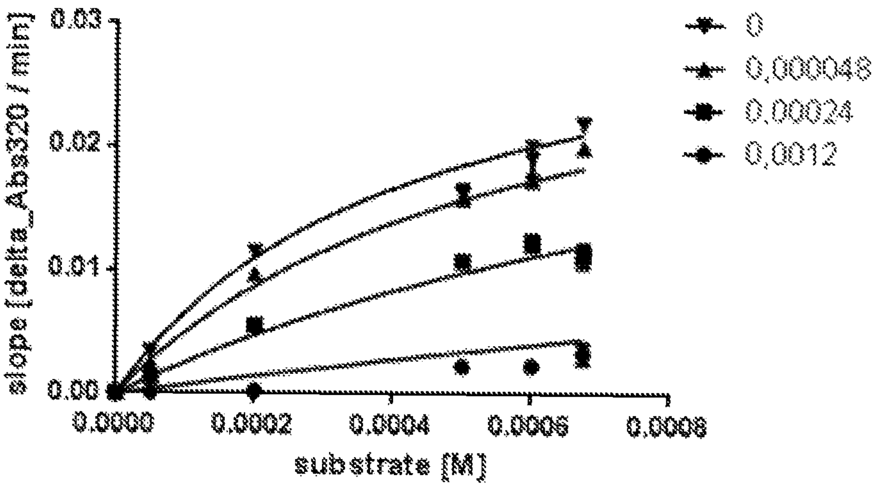

b) Kinetic changes in absorbance at 320 nm over time (delta_Abs320/min) in the presence of 0 – 0.0012 M of Cmpd. 1 at the given substrate concentration c) Kinetic changes in absorbance at 320 nm over time (delta_Abs320/min) in the presence of 0 – 0.0012 M of MST at the given substrate concentration d) Kinetic changes in absorbance at 320 nm over time (delta_Abs320/min) in the presence of 0 – 0.0012 M of DKN at the given substrate concentration

HPPD VARIANTS AND METHODS OF USE

CROSS REFERENCE TO RELATED APPLICATIONS

This application is a National Stage entry of International Application No. PCT/EP2016/071159 filed 8 Sep. 2016, which claims priority to European Patent Application No. 15184866.0, filed 11 Sep. 2015.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2923343-423000_ST25.txt" created on 23 Feb. 2018, and 343,979 bytes in size) is submitted concurrently with the instant application, and the entire contents of the Sequence Listing are incorporated herein by reference.

BACKGROUND

Field of the Invention

This invention relates to plant molecular biology, particularly novel HPPD polypeptides that confer improved tolerance to HPPD inhibitor herbicides.

Description of Related Art

The 4-hydroxyphenylpyruvate dioxygenases (HPPDs) are enzymes which catalyze the reaction in which para-hydroxyphenylpyruvate (abbreviated herein as HPP), a tyrosine degradation product, is transformed into homogentisate (abbreviated herein as HGA), the precursor in plants of tocopherol and plastoquinone (Crouch N. P. et al. (1997), Tetrahedron, 53, 20, 6993-7010, Fritze et al. (2004), Plant Physiology 134:1388-1400). Tocopherol acts as a membrane-associated antioxidant. Plastoquinone, firstly acts as an electron carrier between PSII and the cytochrome b6/f complex and secondly, is a redox cofactor for phytoene desaturase, which is involved in the biosynthesis of carotenoids.

Up to now, more than 1000 nucleic acid sequences from various organisms present in the NCBI database were annotated as coding for a putative protein having an HPPD domain. But for most of those, it has not been proven that the protein would have an HPPD enzymatic activity, neither in an in vitro assay, nor in an in planta approach, nor that such HPPD protein can confer herbicide tolerance to HPPD inhibitor herbicides when expressed in a plant. Several HPPD proteins and their primary sequences have been described in the state of the art, in particular the HPPD proteins of bacteria such as *Pseudomonas* (Rüetschi et al., Eur. J. Biochem., 205, 459-466, 1992, WO96/38567), Kordia (WO2011/076889) *Synechococcus* (WO2011/076877), *Acidobacterium* and *Mucilaginibacter* (WO2015/022634), *Rhodococcus* (WO2011/076892), of protists such as *Blepharisma* (WO2011/076882), of euryarchaeota such as *Picrophilus* (WO2011/076885), of algae such as *Chlamydomonas reinhardtii* (ES2275365; WO2011145015), *Scenedesmus* (WO2015/022634), of plants such as *Arabidopsis* (WO96/38567, GENBANK® AF047834), carrot (WO 96/38567, GENBANK® 87257), *Avena sativa* (WO2002/046387, WO2011/068567), wheat (WO2002/046387), *Brachiaria platyphylla* (WO2002/046387), *Cenchrus echinatus* (WO2002/046387), *Lolium rigidum* (WO2002/046387), *Festuca arundinacea* (WO2002/046387), *Setaria faberi* (WO 2002/046387), *Eleusine indica* (WO2002/046387), *Sorghum* (WO2002046387, WO2012021785), corn (WO2012/021785), *Coptis japonica* (WO2006/132270), *Lemna* (WO2015/022634), or of mammals such as mouse or pig, or of fungi such as Coccicoides (GENBANK® COITRP).

Inhibition of HPPD leads to uncoupling of photosynthesis, deficiency in accessory light-harvesting pigments and, most importantly, to destruction of chlorophyll by UV-radiation and reactive oxygen species (bleaching) due to the lack of photo-protection normally provided by carotenoids (Norris et al. (1995), Plant Cell 7: 2139-2149). Bleaching of photosynthetically active tissues leads to growth inhibition and plant death.

Some molecules which inhibit HPPD (hereinafter named HPPD inhibitor herbicides), and which inhibit transformation of the HPP into HGA while binding specifically to the enzyme, have proven to be very effective herbicides.

At present, most commercially available HPPD inhibitor herbicides belong to one of these chemical families, as listed below:

1) the triketones, e.g. benzobicyclon [i.e. 3-[2-chloro-4-(methylsulfonyl)benzoyl]-4-(phenylsulfanyl)bicyclo[3.2.1]oct-3-en-2-one]; sulcotrione [i.e. 2-[2-chloro-4-(methylsulfonyl)benzoyl]-1,3-cyclohexanedione], mesotrione [i.e. 2-[4-(methylsulfonyl)-2-nitrobenzoyl]-1,3-cyclohexanedione] (abbreviated herein as MST); tembotrione [i.e. 2-[2-chloro-4-(methylsulfonyl)-3-[(2,2,2,-trifluoroethoxy)methyl]benzoyl]-1,3-cyclohexanedione]; tefuryltrione [i.e. 2-[2-chloro-4-(methylsulfonyl)-3-[[(tetrahydro-2-furanyl)methoxy]methyl]benzoyl]-1,3-cyclohexanedione]]; bicyclopyrone [i.e. 4-hydroxy-3-[[2-[(2-methoxyethoxy)methyl]-6-(trifluoromethyl)-3-pyridinyl]carbonyl]bicyclo[3.2.1]oct-3-en-2-one]; fenquinotrione [i.e. 2-[[8-chloro-3,4-dihydro-4-(4-methoxyphenyl)-3-oxo-2-quinoxalinyl]carbonyl]-1,3-cyclohexanedione], and as described in WO2007088876, WO2009016841, WO2010089993, WO2010116122, WO2012002096, WO201131658, WO2012136703, JP2013040141, WO2013080484, WO2014014904, WO2014031971, US20140106968;

2) the diketonitriles, e.g. 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1,3-dione;

3) the isoxazoles, e.g. isoxaflutole [i.e. (5-cyclopropyl-4-isoxazolyl)[2-(methylsulfonyl)-4-(trifluoromethyl)phenyl]methanone]. In plants, isoxaflutole (abbreviated herein as IFT) is rapidly metabolized to DKN, a diketonitrile compound which exhibits the HPPD inhibitor property;

4) the hydroxypyrazoles, e.g. pyrazoxyfen [i.e. 2-[[4-(2,4-dichlorobenzoyl)-1,3-dimethyl-1H-pyrazol-5-yl]oxy]-1-phenylethanone]; benzofenap [i.e. 2-[[4-(2,4-dichloro-3-methylbenzoyl)-1,3-dimethyl-1H-pyrazol-5-yl]oxy]-1-(4-methylphenyl)ethanone]; pyrazolynate [i.e. (2,4-dichlorophenyl)[1,3-dimethyl-5-[[(4-methylphenyl)sulfonyl]oxy]-1H-pyrazol-4yl]methanone]; pyrasulfotole [i.e. (5-hydroxy-1,3-dimethyl-1H-pyrazol-4-yl)[2-(methylsulfonyl)-4-(trifluoromethyl)phenyl]methanone]; topramezone [i.e. [3-(4,5-dihydro-3-isoxazolyl)-2-methyl-4-(methylsulfonyl)phenyl](5-hydroxy-1-methyl-1H-pyrazol-4-yl)methanone]; tolpyralate [i.e. 1-[[1-ethyl-4-[3-(2-methoxyethoxy)-2-methyl-4-(methylsulfonyl)benzoyl]-1H-pyrazol-5-yl]oxy]ethyl methyl carbonate];

5) N-(1,2,5-oxadiazol-3-yl)benzamides as described in WO2011035874, and WO2012123416, WO2012123409, EP2562174, WO2013064459, WO2013087577, WO2013124238, WO2013124228, WO2013164333, WO2013037342, WO2014053473, WO2014086737, WO2015007662, WO2015007632, WO2015007633, and as described in WO2013072300, WO2013072402, WO2013072450, WO2014184014, WO2014184019, WO2014184058, WO2014192936, WO2015052152, WO2015052178 and the N-(1,3,4-oxadiazol-2-yl)benzamides as described in WO2012126932, and EP2562174, WO2013064459, WO2013087577, WO2013124238, WO2013124228, WO2013124245, WO2013164333, WO2013037342, WO20141053473, WO2014086737, WO2015007662, WO2015007632, WO2015007633; e.g. 2-methyl-N-(5-methyl-1,3,4-oxadiazol-2-yl)-3-(methylsulfonyl)-4-(trifluoromethyl)benzamide (hereinafter also named “Cmpd. 2”); 2-chloro-N-(5-methyl-1,3,4-oxadiazol-2-yl)-3-(methylsulfonyl)-4-(trifluoromethyl)benzamide; 2-chloro-3-(ethylsulfonyl)-N-(5-methyl-1,3,4-oxadiazol-2-yl)-4-(trifluoromethyl)benzamide;

6) N-(tetrazol-5-yl)- or N-(triazol-5-yl)arylcarboxamides as described in WO2012028579, and WO2012123409, WO2013017559, EP2562174, WO2013064459, WO2013064457, WO2013087577, WO2013104705, WO2013124238, WO2013124228, WO2013124245, WO2013164331, WO2013164333, WO2013174843, WO2013037342, WO2014053473, WO2014086737, WO2015007662, WO2015007632, WO2015007633; e.g. 2-chloro-3-ethoxy-4-(methylsulfonyl)-N-(1-methyl-1H-tetrazol-5-yl)benzamide; 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl)benzamide (hereinafter also named “Cmpd. 1”); 2-(methoxymethyl)-3-(methylsulfinyl)-N-(1-methyl-1H-tetrazol-5-yl)-4-(trifluoromethyl)benzamide, and as described in WO2013072528, WO2013076315, WO2013076316, WO2013083859, WO2013092834, WO2013139760, WO2013144231, WO2014126070, WO2014135654, WO2014184015, WO2014184016, WO2014184017, WO2014184073, WO2014184074, WO2014192936, WO2015022284, WO2015052153, WO2015052173;

7) pyridazinone derivatives as described in WO2013050421 and WO2013083774, WO2014154828, WO2014154882;

8) oxoprazine derivatives as described in WO2013054495;

9) N-(triazol-2-yl)arylcarboxamides as described in WO2013144234, WO2015007564;

10) triazinones as described in WO2014154829; and 11) pyrazolones as described in EP2881387 and EP2881388.

These HPPD inhibitor herbicides can be used against grass and/or broad leaf weeds in field of crop plants that display metabolic tolerance, such as maize (*Zea mays*), rice (*Oryza Sativa*) and wheat (*Triticum aestivum*) in which they are rapidly degraded (Schulz et al. (1993), FEBS letters, 318, 162-166; Mitchell et al. (2001), Pest Management Science, Vol 57, 120-128; Garcia et al. (2000), Biochem., 39, 7501-7507; Pallett et al. (2001), Pest Management Science, Vol 57, 133-142). In order to extend the scope of use of these HPPD inhibitor herbicides, several efforts have been developed in order to confer to plants, particularly plants without or with an underperforming metabolic tolerance, a tolerance level acceptable under agronomic field conditions.

Besides the attempt of by-passing HPPD-mediated production of homogentisate (U.S. Pat. No. 6,812,010), overexpressing the sensitive enzyme so as to produce quantities of the target enzyme in the plant which are sufficient in relation to the herbicide has been performed (WO96/38567). Overexpression of HPPD polypeptides resulted in better pre-emergence tolerance to the diketonitrile derivative (abbreviated herein as DKN) of IFT, but the tolerance level was not sufficient for tolerance to post-emergence treatment (Matringe et al. (2005), Pest Management Science 61: 269-276).

A third strategy was to mutate the HPPD polypeptide in order to obtain a target enzyme which, while retaining its properties of catalyzing the transformation of HPP into HGA, is less sensitive to HPPD inhibitors than is the native HPPD polypeptide before mutation.

This strategy has been successfully applied for the production of plants tolerant to 2-cyano-3-cyclopropyl-1-(2-methylsulphonyl-4-trifluoromethylphenyl)-propane-1,3-dione and to 2-cyano-1-[4-(methylsulphonyl)-2-trifluoromethylphenyl]-3-(1-methylcyclopropyl)propane-1,3-dione (EP496630), two HPPD inhibitor herbicides belonging to the diketonitriles family (WO99/24585). Pro215Leu, Gly336Glu, Gly336Ile, and more particularly Gly336Trp (positions of the mutated amino acid are indicated with reference to the wild-type *Pseudomonas fluorescens* HPPD polypeptide corresponding to SEQ ID NO: 1 of present invention) were identified as mutations which are responsible for an increased tolerance to treatment with these diketonitrile herbicides.

Quite recently, introduction of a *Pseudomonas fluorescens* HPPD gene into the plastid genome of tobacco and soybean has shown to be more effective than nuclear transformation, conferring tolerance to post-emergence application of IFT (Dufourmantel et al. (2007), Plant Biotechnol J. 5(1):118-33).

In WO2004/024928, the inventors sought to increase the prenylquinone biosynthesis (e.g. synthesis of plastoquinones, tocopherols) in the cells of plants by increasing the flux of the HPP precursor into the cells of these plants. This has been done by connecting the synthesis of said precursor to the “shikimate” pathway by overexpression of a prephenate dehydrogenase (PDH) enzyme. They have also noted that the transformation of plants with a gene encoding a PDH enzyme and a gene encoding an HPPD enzyme makes it possible to increase the tolerance of said plants to HPPD inhibitor herbicides.

In WO2009/144079, nucleic acid sequences encoding an hydroxyphenylpyruvate dioxygenase (HPPD) with specific mutations at position 336 of the *Pseudomonas fluorescens* HPPD protein and their use for obtaining plants which are tolerant to HPPD inhibitor herbicides was disclosed.

In WO2002/046387, several domains of HPPD polypeptides originating from plants have been identified that may be relevant to confer tolerance to various HPPD inhibitor herbicides but neither in planta nor biochemical data have been shown to confirm the impact of the as described domain functions.

In WO2008/150473, the combination of two distinct tolerance mechanisms—a modified *Avena sativa* gene coding for a mutant HPPD enzyme and a CYP450 Maize monooxygenase (nsf1 gene)—was exemplified in order to obtain an improved tolerance to HPPD inhibitor herbicides, but no data have been disclosed demonstrating the synergistic effects based on the combination of both proteins.

Further a method to generate plants tolerant to HPPD inhibitor herbicides by overexpressing not only a gene coding for a tolerant HPPD, as for example from *Avena sativa* (US2011/0173718) or *Arabidopsis* (WO2013/064964, WO2014/177999), but also in combination with several plant genes coding for an HST (homogentisate solanesyltransferase) protein is disclosed. However, the level of tolerance to some selected HPPD inhibitor herbicides was rather limited.

In WO2011/094199 and US2011/0185444, the tolerance of several hundred of soybean wild-type lines to the HPPD inhibitor IFT was evaluated. Very few lines displayed reasonable level of tolerance to the herbicides. The putative QTL (quantitative trait loci) responsible for the tolerance was identified. In this region of the genome, a gene coding for an ABC transporter was identified as being the main trait responsible for the improved tolerance to the HPPD inhibitor herbicide observed. However, transgenic plants expressing the identified genes did not display any improvement in tolerance to the tested HPPD inhibitor herbicides.

In WO2010/085705 and US2014/0053295, several mutants of the *Avena sativa* HPPD polypeptide were disclosed. In WO2010/085705 it was shown that some of the variants displayed improved tolerance in vitro to the triketone "Mesotrione" (abbreviated herein as MST), however, only very few mutants were expressed in tobacco plants. Additionally, none of the tobacco plants expressing these mutants displayed improved tolerance to MST or IFT compared to tobacco plants expressing the wild-type *Avena sativa* HPPD gene. In US2014/0053295, a few *Avena sativa* HPPD mutants were expressed in soybean plants and had good tolerance level to MST as known from plants expressing the wild-type *Avena sativa* HPPD gene. However, other herbicides such as tembotrione or IFT induced much higher leaf damage in these soybean plants.

US 2012/0042413 describes mutant maize HPPD polypeptides having HPPD activity but also showing a certain insensitivity to at least one HPPD inhibitor herbicide and further suggests a certain set of mutations at different positions of HPPD polypeptides and finally discloses biochemical data as well as tolerance levels of plants containing few of such mutated HPPD polypeptides. In EP 2453012, several mutants of HPPD polypeptides have been described; however, the improved tolerance of the described mutants was not demonstrated in planta against several HPPD inhibitor herbicides.

In WO2014/043435, recombinant nucleic acid molecules encoding the *Pseudomonas* spp. HPPD polypeptides consisting of an amino acid sequence comprising a proline at the amino acid position corresponding to amino acid position 335 of SEQ ID NO:1; or a proline at the amino acid position corresponding to amino acid position 335 of SEQ ID NO:1 and a tryptophan at the amino acid position corresponding to amino acid position 336 of SEQ ID NO:1; or a serine at the amino acid position corresponding to amino acid position 335 of SEQ ID NO:1, a serine at the amino acid position corresponding to amino acid position 336 of SEQ ID NO:1, a threonine at the amino acid position corresponding to amino acid position 339 of SEQ ID NO:1, and a glutamine at the amino acid position corresponding to amino acid position 340 of SEQ ID NO:1; or a tryptophan at the amino acid position corresponding to amino acid position 188 of SEQ ID NO:1 and a tryptophan at the amino acid position corresponding to amino acid position 336 of SEQ ID NO:1; or a proline at the amino acid position corresponding to amino acid position 335 of SEQ ID NO:1, a serine at the amino acid position corresponding to amino acid position 336 of SEQ ID NO:1, and a glutamic acid at the amino acid position corresponding to amino acid position 340 of SEQ ID NO:1; or a proline at the amino acid position corresponding to amino acid position 335 of SEQ ID NO:1, a tryptophan at the amino acid position corresponding to amino acid position 336 of SEQ ID NO:1, an alanine at the amino acid position corresponding to amino acid position 339 of SEQ ID NO:1, and a glutamine at the amino acid position corresponding to amino acid position 340 of SEQ ID NO:1 were described.

The currently described and partly commercialized HPPD inhibitor herbicides act as slow-binding or slow, tight-binding inhibitors (see Morrison (1982) Trends Biochem. Sci. 7, 102-105). These inhibitors bind slowly (i.e. they have slow rates of association, kon) but not covalently to the HPPD polypeptide (i.e. they produce time-dependent inhibition), and are released very slowly (i.e. they have exceptionally slow rates of dissociation, koff) due to their exceedingly tight interaction with the enzyme.

These inhibitors bind so tightly that stoichiometric titrations with the enzyme are possible.

It has become increasingly recognized that the slow-binding or slow, tight-binding inhibitors are not only extraordinary potent HPPD-inhibitor, but, in addition, have features that make them attractive agrochemicals for weed control. The slow rate of dissociation enhances inhibitor effectiveness to such an extent that ideally only one inhibitor molecule per HPPD polypeptide active site is sufficient to fully inhibit the activity and to maintain this level of inhibition for a long time period even in the absence of free inhibitor molecules in the plant cell. This translates into low application rates of these inhibitors to control undesired weeds in crop growing areas.

The properties of slow-binding or slow, tight-binding inhibitors are advantageous when achieving HPPD inhibition and herbicidal activity is the goal. However, these properties are a major disadvantage when HPPD polypeptides tolerant to these inhibitors are to be invented. Mutations in the HPPD polypeptide that solely reduce the affinity of the inhibitor to the enzyme (ki) do not fully overcome HPPD inhibition since binding of the inhibitor and inhibition of the HPPD polypeptide can still take place and, therefore, the achieved level of inhibition will be maintained for a long time period even in the absence of free inhibitor in the plant cell. In addition the in part commercially available HPPD inhibitor herbicides belong to structurally diverse chemical classes, such as the triketones, the diketonitriles, the isoxazoles, the hydroxypyrazoles, the N-(1,2,5-oxadiazol-3-yl) benzamides, the N-(1,3,4-oxadiazol-2-yl)benzamides, the N-(tetrazol-5-yl)- or N-(triazol-5-yl)arylcarboxamides, the pyridazinone derivatives, the oxoprazine derivatives, the N-(triazol-2-yl), the triazinones, and the pyrazolones. The currently described state of the art HPPD polypeptides demonstrate a rather narrow range of tolerance to structurally diverse HPPD inhibitor herbicides.

Due to the above described kinetic properties of all the currently described and partly commercialized HPPD inhibitor herbicides, up to now, no HPPD inhibitor herbicide tolerant plants with full tolerance against HPPD inhibitor herbicides have been published, despite the many efforts to generate them.

SUMMARY

In the present invention, HPPD polypeptides and plants containing them, showing a full tolerance against one or more HPPD inhibitor herbicides belonging to various chemical classes, are described. It turned out that in order to generate such HPPD polypeptides with maximized and broad tolerance against several classes of HPPD inhibitor herbicides, it is important to reduce the affinity to the HPPD polypeptide (ki) concerning the respective HPPD inhibitor herbicide(s) and simultaneously to ensure an improved rate of dissociation (koff) of a slow-binding or slow, tight-binding inhibitor as known from the wild-type and several mutant HPPD polypeptides to achieve high level of inhibitor tolerance.

In the present invention, this goal was achieved by developing a set of HPPD polypeptides, which have either no or only a significantly reduced affinity to HPPD inhibitor herbicides and, at the same time, the rate of dissociation of the HPPD inhibitor herbicides of the enzyme is increased to such an extent that the HPPD inhibitor herbicides no longer act as slow-binding or slow, tight-binding inhibitors but, instead of this, have become fully reversible inhibitors.

In the present invention, compositions and methods for obtaining a new set of HPPD polypeptides having the before mentioned characteristics (i.e. no or only a significantly reduced affinity to HPPD inhibitor herbicides, increased rate of dissociation of the HPPD inhibitor herbicides of the enzyme; HPPD inhibitor herbicides no longer act as slow-binding or slow, tight-binding inhibitors but have become fully reversible inhibitors) are provided. Compositions include HPPD polypeptides and isolated, recombinant or chimeric nucleic acid molecules encoding such HPPD polypeptides, vectors and host cells comprising those nucleic acid molecules. Compositions also include the antibodies to those polypeptides. The nucleotide sequences can be used in DNA constructs or expression cassettes for transformation and expression in organisms, including microorganisms and plants. The nucleotide sequences may be synthetic sequences that have been designed for expression in an organism including, but not limited to, a microorganism or a plant.

The compositions include nucleic acid molecules encoding herbicide tolerant HPPD polypeptides, including nucleic acid molecules encoding an HPPD polypeptide having (a) a proline at the amino acid position corresponding to amino acid position 335 of SEQ ID NO:1, (b) a histidine or an aspartic acid at the position corresponding to amino acid position 336 of SEQ ID NO:1, and (c) a serine at the position corresponding to amino acid position 337 of SEQ ID NO:1 and, optionally, one or more further amino acid substitutions at the positions corresponding to amino acid positions 204, 213, 264, 268, 270, 310, 315, 330, 331, 338, 339, 340, 344, 345 of SEQ ID NO: 1, including the HPPD polypeptides set forth in any of SEQ ID NO:3-108 as well as fragments thereof.

Compositions also comprise transformed plants, plant cells, tissues, and seeds that are tolerant to the HPPD inhibitor herbicides by the introduction of the nucleic acid sequence of the invention into the genome of the plants, plant cells, tissues, and seeds. The introduction of the sequence allows for HPPD inhibitor herbicides to be applied to plants to selectively kill HPPD inhibitor sensitive weeds or other untransformed plants, but not the transformed organism. The sequences can additionally be used as a marker for selection of plant cells growing in the presence of one or more HPPD inhibitor herbicides.

Methods for identifying HPPD polypeptides with HPPD inhibitor herbicide tolerance activity are additionally provided.

The compositions and methods of the invention are useful for the production of organisms with enhanced tolerance to HPPD inhibitor herbicides. These organisms and compositions comprising the organisms are desirable for agricultural purposes. Plants or seeds comprising the nucleic acid sequence encoding an HPPD polypeptide according to the invention can be grown in a field and harvested to obtain a plant product. The compositions of the invention are also useful for detecting the presence of HPPD inhibitor herbicide tolerant polypeptides or nucleic acids in products or organisms.

BRIEF DESCRIPTION OF THE FIGURES

FIG. 1 shows a simplistic scheme of the coupled HPPD activity assay used in this invention to determine the enzymatic activity of the exemplary HPPD polypeptides.

FIG. 2 shows exemplary kinetic changes in absorbance at 320 nm (Abs320) in raw extracts samples of wild-type and knock-out HPPD polypeptide observed with 200 μM HPP and 0, 4 or 13 μM Cmpd. 1 (2-chloro-3-(methylsulfanyl)-N-(1-methyl-1H-tetrazol-5-yl)-4-(trifluoromethyl)benzamide) according to Example 3 in the coupled HPPD activity assay. The knock-out HPPD polypeptide was obtained by exchanging a histidine to an alanine at the amino acid position corresponding to amino acid position 162 of SEQ ID NO:1. This position is well known for its importance due to its involvement in the coordinated binding of the iron atom in the active site of the HPPD polypeptide (Serre et al. (1999), Structure, 7, 977-988).

FIG. 3 shows exemplary kinetic changes in absorbance at 320 nm (Abs320) of a purified mutant HPPD polypeptide corresponding to SEQ ID NO:17 according to Example 3 observed at high substrate concentration and with 0, 48, 240 or 1200 μM Cmpd. 2 (2-methyl-N-(5-methyl-1,3,4-oxadiazol-2-yl)-3-(methylsulfonyl)-4-(trifluoromethyl)benzamide) in the coupled HPPD activity assay. The apparent kinetic constant ($k_{app}$) was determined as signal change over time (delta_Abs320/min) in the boxed timeframe.

a) Kinetic changes in absorbance at 320 nm over time (delta_Abs320/min) in the presence of 0-0.0012 M of Cmpd. 2 at the given substrate concentration, according to Example 3;

b) Kinetic changes in absorbance at 320 nm over time (delta_Abs320/min) in the presence of 0-0.0012 M of Cmpd. 1 (2-chloro-3-(methylsulfanyl)-N-(1-methyl-1H-tetrazol-5-yl)-4-(trifluoromethyl)benzamide) at the given substrate concentration, according to Example 3;

c) Kinetic changes in absorbance at 320 nm over time (delta_Abs320/min) in the presence of 0-0.0012 M of MST at the given substrate concentration, according to Example 3;

d) Kinetic changes in absorbance at 320 nm over time (delta_Abs320/min) in the presence of 0-0.0012 M of DKN at the given substrate concentration, according to Example 3.

Figure 4:
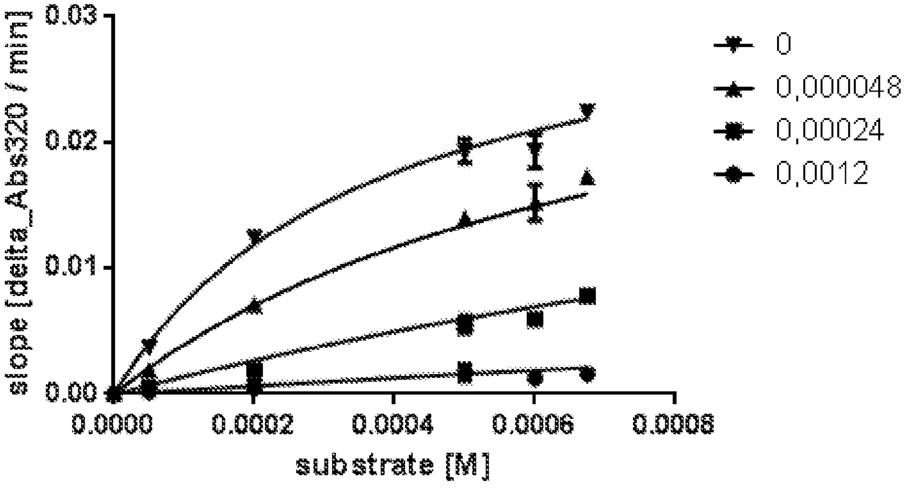
FIG. 4 depicts data from an exemplary ki determination with a purified mutant HPPD polypeptide corresponding to SEQ ID NO:17 with different inhibitor and substrate (HPP) concentrations by fitting according to the competitive inhibition model.
Figure 4:
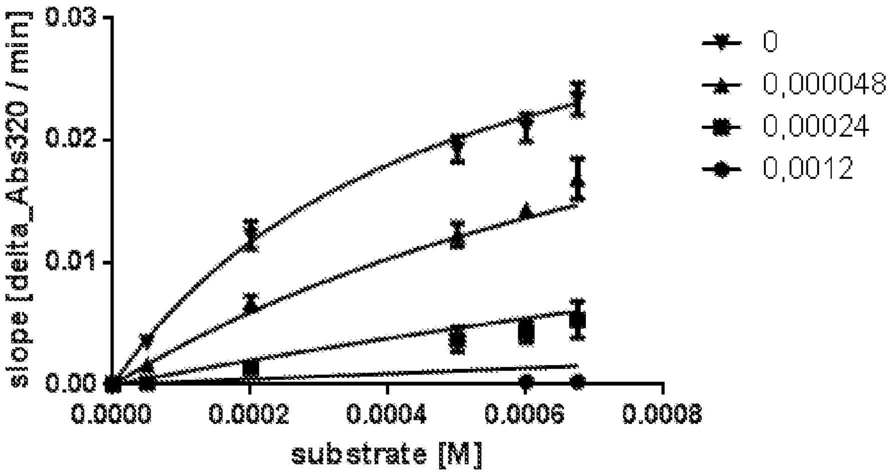
Figure 4:
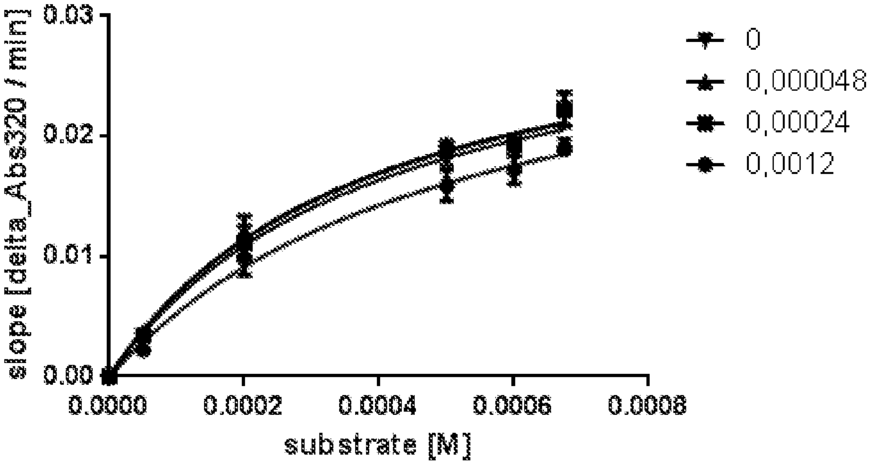

All exemplary HPPD polypeptides, which are summarized in Tables 2, 3, 4, and 5 were measured and analyzed as shown for example with SEQ ID NO:17 in FIGS. 3 & 4.

DETAILED DESCRIPTION OF A PREFERRED EMBODIMENT

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Overview

Several efforts have been developed in order to confer to plants an agronomically-acceptable level of tolerance to a broad range of HPPD inhibitor herbicides, including bypassing HPPD-mediated production of homogentisate (U.S. Pat. No. 6,812,010), overexpressing the sensitive enzyme so as to produce quantities of the target enzyme in the plant, which are sufficient in relation to the herbicide (WO96/38567), and mutating the HPPD in order to obtain a target enzyme which, while retaining its properties of catalyzing the transformation of HPP into homogentisate, is less sensitive to HPPD inhibitors than is the native HPPD before mutation.

Despite these successes obtained for the development of plants showing tolerance to several HPPD inhibitor herbicides described above, it is still necessary to develop and/or improve the tolerance of plants to newer or to several different HPPD inhibitor herbicides belonging to various chemical classes, particularly HPPD inhibitor herbicides belonging to the classes of triketones (e.g. benzobicyclon, sulcotrione mesotrione, tembotrione, tefuryltrione, bicyclopyrone, fenquinotrione), diketonitriles, isoxazoles (e.g. isoxaflutole), hydroxypyrazoles (e.g. pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (e.g. 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (e.g. 2-chloro-3-ethoxy-4-(methylsulfonyl)-N-(1-methyl-1H-tetrazol-5-yl)benzamide), 4-(difluoromethyl)-2-methoxy-3-(methylsulfonyl)-N-(1-methyl-1H-tetrazol-5-yl)benzamide); 2-chloro-3-(methylsulfanyl)-N-(1-methyl-1H-tetrazol-5-yl)-4-(trifluoromethyl)benzamide (hereinafter also named "Cmpd. 1"); 2-(methoxymethyl)-3-(methylsulfinyl)-N-(1-methyl-1H-tetrazol-5-yl)-4-(trifluoromethyl)benzamide, pyridazinone derivatives, oxoprazine derivatives, triketones, N-(triazol-2-yl)arylcarboxamides, triazinones, and pyrazolones.

Thus, the present invention provides improved compositions and methods for regulating HPPD inhibitor herbicide tolerance. HPPD inhibitor herbicides like those of the class of triketones (e.g. benzobicyclon, sulcotrione mesotrione, tembotrione, tefuryltrione, bicyclopyrone, fenquinotrione), diketonitriles, isoxazoles (e.g. isoxaflutole), hydroxypyrazoles (e.g. pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (e.g. 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (e.g. 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl)benzamide (hereinafter also named "Cmpd. 1"); 2-(methoxymethyl)-3-(methylsulfinyl)-N-(1-methyl-1H-tetrazol-5-yl)-4-(trifluoromethyl)benzamide, pyridazinone derivatives, oxoprazine derivatives, N-(triazol-2-yl)arylcarboxamides, triazinones, and pyrazolones have an outstanding herbicidal activity against a broad spectrum of economically important monocotyledonous and dicotyledonous annual harmful plants. The active substances also act efficiently on perennial harmful plants, which produce shoots from rhizomes, wood stocks or other perennial organs and which are difficult to control. Within the meaning of the present invention, "herbicide" is understood as being a herbicidally active substance on its own or such a substance which is combined with an additive which alters its efficacy, such as, for example, an agent which increases its activity (a synergistic agent) or which limits its activity (a safener). The herbicide may further comprise solid or liquid adjuvants or carriers that are ordinarily employed in formulation technology (e.g. natural or regenerated mineral substances, solvents, dispersants, wetting agents, tackifiers, emulsifiers, growth promoting agents, and the like), as well as one or more additional herbicides and/or one or more pesticides (e.g. insecticides, virucides, microbicides, amoebicides, pesticides, fungicides, bactericides, nematicides, molluscicides, and the like).

The methods involve transforming organisms with nucleotide sequences encoding an HPPD inhibitor herbicide tolerance gene of the invention or otherwise introducing such HPPD inhibitor herbicide tolerance genes in organisms not containing them (e.g. by mating, cell fusion, or by crossing organisms containing an introduced HPPD inhibitor herbicide tolerance gene of the invention with organisms not containing it and obtaining progeny containing such gene). The nucleotide sequences of the invention are useful for preparing plants that show increased tolerance to HPPD inhibitor herbicides, particularly increased tolerance to HPPD inhibitor herbicides of the class of triketones (preferably benzobicyclon, sulcotrione, mesotrione, tembotrione, tefuryltrione, bicyclopyrone, or fenquinotrione), diketonitriles, isoxazoles (preferably isoxaflutole), hydroxypyrazoles (preferably pyrazoxyfen, benzofenap, pyrazolynate, pyrasulfotole, topramezone, or tolpyralate), N-(1,2,5-oxadiazol-3-yl)benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl)benzamide (hereinafter also named "Cmpd. 1"); 2-(methoxymethyl)-3-(methylsulfinyl)-N-(1-methyl-1H-tetrazol-5-yl)-4-(trifluoromethyl)benzamide, pyridazinone derivatives, oxoprazine derivatives, N-(triazol-2-yl)arylcarboxamides, triazinones, and pyrazolones.

The expression of the HPPD inhibitor herbicide tolerance gene of the invention may also result in tolerance towards the "coumarone-derivative herbicides" (described in WO2009/090401, WO2009/090402, WO2008/071918, WO2008/009908). In this regard, any one of the HPPD inhibitor herbicide tolerance genes of the invention can also be expressed in a plant also expressing a chimeric homogentisate solanesyltransferase (HST) gene or a mutated HST gene as described in WO2011/145015, WO2013/064987, WO2013/064964, or WO2010/029311, to obtain plants tolerant to HST inhibitor herbicides. As used herein, a "coumarone-derivative herbicide" or "HST inhibitor herbicide" encompasses compounds which fall under the IUPAC nomenclature of 5H-thiopyrano[4,3-b]pyridin-8-ol, 5H-thiopyrano[3,4-b]pyrazin-8-ol, oxathiino[5,6-b]pyridin-4-ol, and oxathiino[5,6-b]pyrazin-4-ol. Thus, by "HPPD inhibitor herbicide tolerance" gene of the invention is intended a gene encoding a polypeptide that confers upon a cell or organism the ability to tolerate a higher concentration of an HPPD inhibitor herbicide than such cell or organism that does not express the protein, or to tolerate a certain concentration of an HPPD inhibitor herbicide for a longer time than such cell or organism that does not express the protein, or that confers upon a cell or organism the ability to perform photosynthesis, grow, and/or reproduce with less damage or growth inhibition observed than such cell or organism not expressing such protein.

An "HPPD inhibitor herbicide tolerance polypeptide" comprises a polypeptide that confers upon a cell or organism the ability to tolerate a higher concentration of HPPD inhibitor herbicides than such cell or organism that does not express the protein, or to tolerate a certain concentration of HPPD inhibitor herbicides for a longer period of time than such cell or organism that does not express the polypeptide, or that confers upon a cell or organism the ability to perform photosynthesis, grow, and/or reproduce with less damage or growth inhibition observed than such cell or organism not expressing such polypeptide.

The term "polypeptide" comprises proteins such as enzymes, antibodies and medium-length polypeptides and short peptides down to an amino acid sequence length below ten.

The term "enzyme" means in the present invention any polypeptide catalyzing the reaction in which para-hydroxyphenylpyruvate is transformed into homogentisate. It includes naturally-occurring enzymes, as well as enzyme variants and derivatives thereof. It also comprises any fragment of such an enzyme, and variants engineered by insertion, deletion, recombination and/or any other method, that leads to enzymes that differ in their amino acid sequence from the naturally-occurring enzyme or the enzyme variants. It also comprises protein molecules with posttranslational and/or chemical modifications, e.g. glycosylation, gamma carboxylation and acetylation, any molecular complex or fusion protein comprising one of the aforementioned proteins.

The terms "polypeptide variant" or "mutant polypeptide" means any polypeptide molecule obtained by mutagenesis, preferably by site-directed or random mutagenesis with an altered amino acid sequence compared to the respective wild-type sequence. By "tolerate", "tolerance" or "resistant" is intended either to survive a particular HPPD inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with HPPD inhibitor herbicide compared to such plants not treated with such herbicide (but where weeds have been removed or prevented by a mechanism other than application of the HPPD inhibitor herbicide, such as the methods described in WO2011/100302, which is herein incorporated by reference in its entirety).

In addition to conferring upon a cell HPPD inhibitor herbicide tolerance, the HPPD nucleic acid sequences of the invention encode polypeptides having HPPD activity, i.e. catalyzing the reaction in which para-hydroxyphenylpyruvate (HPP) is transformed into homogentisate. The catalytic activity of an HPPD polypeptide may be defined by various methods well-known in the art. WO2009/144079 and WO2014/043435 describe various suitable screening methods.

The enzymatic activity of HPPD polypeptides can be measured by any method that makes it possible either to measure the decrease in the amount of the HPP or $O_2$ substrates, or to measure the accumulation of any of the products derived from the enzymatic reaction, i.e. homogentisate or $CO_2$. In particular, the HPPD activity can be measured by means of the method described in WO2009/144079; Garcia et al. (1997), Biochem. J. 325, 761-769; Garcia et al. (1999), Plant Physiol. 119, 1507-1516; or in WO2012/021785, which are incorporated herein by reference.

For the purposes of the present invention, a "reference" HPPD polypeptide (or HPPD gene encoding such polypeptide) is any HPPD polypeptide or nucleic acid against which the HPPD polypeptide or HPPD nucleic acid of the invention is being compared. For the purposes of describing the HPPD polypeptides of the present invention, the terms "protein" and "polypeptide" are used interchangeably. This reference HPPD polypeptide can be a native plant, bacterial, or animal HPPD, or can be a mutated HPPD polypeptide that is known in the art such as the PfP215L and PfG336F mutants described in International Patent Publication WO2009/144079, or can be either of the PfHPPDevo33, PfHPPDevo36, PfHPPDevo37, PfHPPDevo40, or PfHPPDevo41 proteins of WO2014/043435; PfHPPDevo41 is set forth in present application as SEQ ID NO:2. Such reference HPPD polypeptide can be used to determine whether the HPPD polypeptide or nucleic acid of the invention has a particular property of interest (e.g., improved, comparable or decreased HPPD inhibitor herbicide tolerance or HPPD polypeptide enzymatic activity; improved, comparable or decreased expression in a host cell; improved, comparable or decreased protein stability, and the like). In various embodiments herein, the HPPD inhibitor herbicide tolerant polypeptide encoded by a nucleic acid (including isolated, recombinant and chimeric genes thereof, vectors, host cells, plants, plant parts, and seeds comprising the nucleic acid, HPPD polypeptides and compositions thereof encoded by the nucleic acid, as well as methods of using the polypeptide encoded by the nucleic acid for increasing tolerance of a plant to HPPD inhibitor herbicides, particularly increased tolerance to HPPD inhibitor herbicides of the class of triketones (preferably benzobicyclon, sulcotrione, mesotrione, tembotrione, tefuryltrione, bicyclopyrone, fenquinotrione), diketonitriles, isoxazoles (preferably isoxaflutole), hydroxypyrazoles (preferably pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl)benzamide (hereinafter also named "Cmpd. 1"); 2-(methoxymethyl)-3-(methylsulfinyl)-N-(1-methyl-1H-tetrazol-5-yl)-4-(trifluoromethyl)benzamide), pyridazinone derivatives, oxoprazine derivatives, N-(triazol-2-yl)arylcarboxamides, triazinones, and pyrazolones) has (a) a proline at the amino acid position corresponding to amino acid position 335 of SEQ ID NO:1, (b) a histidine or aspartic acid at the position corresponding to amino acid position 336 of SEQ ID NO:1, and (c) a serine at the position corresponding to amino acid position 337 of SEQ ID NO:1 and, optionally, one or more further amino acid substitutions at the positions corresponding to amino acid positions 204, 213, 264, 268, 270, 310, 315, 330, 331, 338, 339, 340, 344, 345 of SEQ ID NO:1, including the HPPD proteins set forth in any of SEQ ID NOs:3-108. By "corresponding to" is intended the nucleotide or amino acid position relative to that position in SEQ ID NO:1 when two (or more) sequences are aligned using standard alignment algorithms. The term "position" in a polynucleotide or polypeptide refers to specific single bases or amino acids in the sequence of the polynucleotide or polypeptide, respectively. The term "site" in a polynucleotide or polypeptide refers to a certain position or region in the sequence of the polynucleotide or polypeptide, respectively. The term "polynucleotide" corresponds to any genetic material of any length and any sequence, comprising single-stranded and double-stranded DNA and RNA molecules, including regulatory elements, structural genes, groups of genes, plasmids, whole genomes, and fragments thereof.

In one embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) consists of an amino acid sequence comprising (a) a proline at the amino acid position corresponding to amino acid position 335 of SEQ ID NO:1, (b) a histidine or an aspartic acid at the position corresponding to amino acid position 336 of SEQ ID NO:1, and (c) a serine at the position corresponding to amino acid position 337 of SEQ ID NO:1, and wherein said HPPD polypeptide is tolerant to one or more HPPD inhibitor herbicides.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising (a) a proline at the amino acid position corresponding to amino acid position 335 of SEQ ID NO:1, (b) a histidine or an aspartic acid at the position corresponding to amino acid position 336 of SEQ ID NO:1, and (c) a serine at the position corresponding to amino acid position 337 of SEQ ID NO:1, and further comprising i. a methionine, threonine, serine, or leucine at the amino acid position corresponding to amino acid position 204 of SEQ ID NO:1; and/or ii. a lysine or leucine at the amino acid position corresponding to amino acid position 213 of SEQ ID NO:1; and/or iii. an arginine, lysine, glutamine, or leucine at the amino acid position corresponding to amino acid position 264 of SEQ ID NO:1; and/or iv. an arginine, glycine, or serine at the amino acid position corresponding to amino acid position 268 of SEQ ID NO:1; and/or v. an arginine, leucine, glutamic acid, proline or serine at the amino acid position corresponding to amino acid position 270 of SEQ ID NO:1; and/or vi. a serine, histidine, or lysine at the amino acid position corresponding to amino acid position 310 of SEQ ID NO:1; and/or vii. an arginine, methionine or histidine at the amino acid position corresponding to amino acid position 315 of SEQ ID NO:1; and/or viii. a histidine, alanine, phenylalanine, valine, or glycine at the amino acid position corresponding to amino acid position 330 of SEQ ID NO:1; and/or ix. a proline, histidine, serine, isoleucine, or leucine at the amino acid position corresponding to amino acid position 331 of SEQ ID NO:1; and/or x. a valine at the amino acid position corresponding to amino acid position 338 of SEQ ID NO:1; and/or xi. a glutamic acid, arginine, alanine, or threonine at the amino acid position corresponding to amino acid position 339 of SEQ ID NO:1; and/or xii. an arginine, glutamine, methionine, glutamic acid, glycine, leucine, or valine at the amino acid position corresponding to amino acid position 340 of SEQ ID NO:1; and/or xiii. a glutamine, proline, or arginine at the amino acid position corresponding to amino acid position 344 of SEQ ID NO:1; and/or xiv. a lysine, arginine, methionine, alanine, or valine at the amino acid position corresponding to amino acid position 345 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising (a) a proline at the amino acid position corresponding to amino acid position 335 of SEQ ID NO:1, (b) a histidine or an aspartic acid at the position corresponding to amino acid position 336 of SEQ ID NO:1, and (c) a serine at the position corresponding to amino acid position 337 of SEQ ID NO:1, and further comprising i. a leucine or lysine at the amino acid position corresponding to amino acid position 213 of SEQ ID NO:1; and/or ii. an arginine or leucine at the amino acid position corresponding to amino acid position 264 of SEQ ID NO:1; and/or iii. an arginine, glycine or serine at the amino acid position corresponding to amino acid position 268 of SEQ ID NO:1; and/or iv. a glutamic acid or serine at the amino acid position corresponding to amino acid position 270 of SEQ ID NO:1; and/or v. an arginine or methionine at the amino acid position corresponding to amino acid position 315 of SEQ ID NO:1; and/or vi. a histidine at the amino acid position corresponding to amino acid position 330 of SEQ ID NO:1; and/or vii. a valine at the amino acid position corresponding to amino acid position 338 of SEQ ID NO:1; and/or viii. an arginine, or valine at the amino acid position corresponding to amino acid position 340 of SEQ ID NO:1; and/or ix. a glutamine at the amino acid position corresponding to amino acid position 344 of SEQ ID NO:1; and/or x. a lysine, valine, or methionine at the amino acid position corresponding to amino acid position 345 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising
(a) a proline at the amino acid position corresponding to amino acid position 335 of SEQ ID NO:1,
(b) a histidine or an aspartic acid at the position corresponding to amino acid position 336 of SEQ ID NO:1, and
(c) a serine at the position corresponding to amino acid position 337 of SEQ ID NO:1 and further comprising

- i. a lysine at the amino acid position corresponding to amino acid position 213 of SEQ ID NO:1; and/or
- ii. an arginine or leucine at the amino acid position corresponding to amino acid position 264 of SEQ ID NO:1; and/or
- iii. a glycine or arginine at the amino acid position corresponding to amino acid position 268 of SEQ ID NO:1; and/or
- iv. a glutamic acid at the amino acid position corresponding to amino acid position 270 of SEQ ID NO:1; and/or
- v. an arginine at the amino acid position corresponding to amino acid position 315 of SEQ ID NO:1; and/or
- vi. a histidine at the amino acid position corresponding to amino acid position 330 of SEQ ID NO:1; and/or
- vii. a valine at the amino acid position corresponding to amino acid position 338 of SEQ ID NO:1; and/or
- viii. an arginine or valine at the amino acid position corresponding to amino acid position 340 of SEQ ID NO:1; and/or
- ix. a glutamine at the amino acid position corresponding to amino acid position 344 of SEQ ID NO:1; and/or
- x. a lysine, valine, or methionine at the amino acid position corresponding to amino acid position 345 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising
(a) a proline at the amino acid position corresponding to amino acid position 335 of SEQ ID NO:1,
(b) a histidine or an aspartic acid at the position corresponding to amino acid position 336 of SEQ ID NO:1, and
(c) a serine at the position corresponding to amino acid position 337 of SEQ ID NO:1 and further comprising

- (i) a glycine or arginine at the amino acid position corresponding to amino acid position 268 of SEQ ID NO:1,
- (ii) a glutamic acid at the amino acid position corresponding to amino acid position 270 of SEQ ID NO:1,
- (iii) a valine at the amino acid position corresponding to amino acid position 340 of SEQ ID NO:1; and
- (iv) a valine at the amino acid position corresponding to amino acid position 345 of SEQ ID NO:1, In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising
(a) a proline at the amino acid position corresponding to amino acid position 335 of SEQ ID NO:1,
(b) a histidine or an aspartic acid at the position corresponding to amino acid position 336 of SEQ ID NO:1, and
(c) a serine at the position corresponding to amino acid position 337 of SEQ ID NO:1 and further comprising

- (i) a lysine at the amino acid position corresponding to amino acid position 213 of SEQ ID NO: 1,
- (ii) a glycine at the amino acid position corresponding to amino acid position 268 of SEQ ID NO:1,
- (iii) a glutamic acid at the amino acid position corresponding to amino acid position 270 of SEQ ID NO:1,
- (iv) a valine at the amino acid position corresponding to amino acid position 340 of SEQ ID NO:1; and
- (v) a valine at the amino acid position corresponding to amino acid position 345 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising
(a) a proline at the amino acid position corresponding to amino acid position 335 of SEQ ID NO:1,
(b) a histidine or an aspartic acid at the position corresponding to amino acid position 336 of SEQ ID NO:1, and
(c) a serine at the position corresponding to amino acid position 337 of SEQ ID NO:1 and further comprising

- (i) a lysine at the amino acid position corresponding to amino acid position 213 of SEQ ID NO: 1,
- (ii) a leucine at the amino acid position corresponding to amino acid position 264 of SEQ ID NO: 1,
- (iii) a glycine at the amino acid position corresponding to amino acid position 268 of SEQ ID NO:1,
- (iv) a glutamic acid at the amino acid position corresponding to amino acid position 270 of SEQ ID NO:1,
- (v) a valine or arginine at the amino acid position corresponding to amino acid position 340 of SEQ ID NO:1;
- (vi) a glutamine at the amino acid position corresponding to amino acid position 344 of SEQ ID NO: 1, and
- (vii) a methionine at the amino acid position corresponding to amino acid position 345 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising
(a) a proline at the amino acid position corresponding to amino acid position 335 of SEQ ID NO:1,
(b) a histidine or an aspartic acid at the position corresponding to amino acid position 336 of SEQ ID NO:1, and
(c) a serine at the position corresponding to amino acid position 337 of SEQ ID NO:1 and further comprising

- (i) a leucine at the amino acid position corresponding to amino acid position 264 of SEQ ID NO: 1,
- (ii) an arginine at the amino acid position corresponding to amino acid position 268 of SEQ ID NO:1,
- (iii) a glutamic acid at the amino acid position corresponding to amino acid position 270 of SEQ ID NO:1,
- (iv) an arginine at the amino acid position 315 corresponding to amino acid position SEQ ID NO: 1,
- (v) a valine at the amino acid position corresponding to amino acid position 340 of SEQ ID NO:1;

(vi) a glutamine at the amino acid position corresponding to amino acid position 344 of SEQ ID NO: 1, and (vii) a methionine at the amino acid position corresponding to amino acid position 345 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising a. a proline at the amino acid position corresponding to amino acid position 335 of SEQ ID NO:1, and b. a histidine at the position corresponding to amino acid position 336 of SEQ ID NO:1, or c. an aspartic acid at the position corresponding to amino acid position 336 of SEQ ID NO:1, and d. a serine at the position corresponding to amino acid position 337 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) consists of an amino acid sequence comprising:

a. a proline at the amino acid position corresponding to amino acid position 335 of SEQ ID NO:1;

b. a histidine at the position corresponding to amino acid position 336 of SEQ ID NO:1 or an aspartic acid at the position corresponding to amino acid position 336 of SEQ ID NO:1;

c. a serine at the position corresponding to amino acid position 337 of SEQ ID NO:1; and d. a histidine at the position corresponding to amino acid position 330 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising:

a. a proline at the amino acid position corresponding to amino acid position 335 of SEQ ID NO:1;

b. a histidine at the position corresponding to amino acid position 336 of SEQ ID NO:1, or an aspartic acid at the position corresponding to amino acid position 336 of SEQ ID NO:1;

c. a serine at the position corresponding to amino acid position 337 of SEQ ID NO:1; and d. a valine at the position corresponding to amino acid position 340 of SEQ ID NO:1.

In another embodiment, the HPPD polypeptide of the present invention (including the nucleotide sequence encoding it and recombinant and chimeric genes thereof, vectors, host cells, plants, plant parts, and seeds comprising the nucleotide sequence encoding the HPPD polypeptide of the invention) being tolerant to one or more HPPD inhibitor herbicides consists of an amino acid sequence comprising:

a. a proline at the amino acid position corresponding to amino acid position 335 of SEQ ID NO:1 b. a histidine at the position corresponding to amino acid position 336 of SEQ ID NO:1 or an aspartic acid at the position corresponding to amino acid position 336 of SEQ ID NO:1;

c. a serine at the position corresponding to amino acid position 337 of SEQ ID NO:1; and d. a valine at the position corresponding to amino acid position 345 of SEQ ID NO:1.

Table 1 summarizes the respective amino acid positions in comparison to the reference wild-type *Pseudomonas fluorescens* HPPD polypeptide (SEQ ID NO:1) where the HPPD polypeptide variants according to the invention comprising three or more amino acid substitutions. If not otherwise explicitly stated the exchanges at the relevant amino acid positions are always referred to the reference wild-type *Pseudomonas fluorescens* HPPD polypeptide corresponding to SEQ ID NO:1.

TABLE 1

Overview of exemplary amino acid exchanges relative to the HPPD polypeptide corresponding to SEQ ID NO: 1

| Amino acid position relative to SEQ ID NO: 1 | Exemplary amino acid exchanges |
|---|---|
| 204 | M, T, S, L |
| 213 | L, K |
| 264 | R, K, Q, L |
| 268 | G, S, R |
| 270 | R, L, E, P, S |
| 310 | S, H, K |
| 315 | R, M, H |
| 330 | H, A, F, V, G |
| 331 | I, H, P, S, L |
| 335 | P |
| 336 | D, H |
| 337 | S |
| 338 | V |
| 339 | E, R, A, T |
| 340 | G, R, E, V, Q, M, L |
| 344 | Q, P, R |
| 345 | V, K, M, R, A |

Amino acids are referred to herein using the name of the amino acid, the three letter abbreviation or the single letter abbreviation. The table below provides a list of the standard amino acids together with their abbreviations.

| | | |
|---|---|---|
| Alanine | A | Ala |
| Cysteine | C | Cys |
| Aspartic acid | D | Asp |
| Glutamic acid | E | Glu |
| Phenylalanine | F | Phe |
| Glycine | G | Gly |
| Histidine | H | His |
| Isoleucine | I | Ile |
| Lysine | K | Lys |
| Leucine | L | Leu |
| Methionine | M | Met |
| Asparagine | N | Asn |
| Proline | P | Pro |
| Glutamine | Q | Gln |
| Arginine | R | Arg |
| Serine | S | Ser |
| Threonine | T | Thr |
| Valine | V | Val |
| Tryptophan | W | Trp |
| Tyrosine | Y | Tyr |
| Cysteine | C | Cys |

It is well known to one of ordinary skill in the art that the genetic code is degenerate, that is more than one codon triplet can code for the same amino acid. Therefore, the amino acid sequences provided herein, can be generated by alternate sequences that use different codons to encode the same amino acid sequence.

In another embodiment, HPPD polypeptides according to the invention have at least 53%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence set forth herein as SEQ ID NO:1.

Exemplary HPPD sequences that can be modified according to the present invention include those from bacteria, particularly from *Pseudomonas* spp. type, more particularly from *Pseudomonas fluorescens, Pseudomonas putida, Pseudomonas aeruginosa, Pseudomonas testosteroni* (*Comamonas testosteroni*).

For the purposes of the present invention, the HPPD polypeptide of the invention may also comprise further modifications, for example, wherein some amino acids (e.g. 1 to 17 amino acids) have been replaced, added or deleted for cloning purposes, to make a transit peptide fusion, and the like, which retains HPPD activity, i.e. the property of catalyzing the conversion of para-hydroxyphenylpyruvate to homogentisate, or can be any HPPD polypeptide that can be further improved. For example, the HPPD polypeptide that can be further improved by the modifications described herein can be the variant HPPD derived from *Pseudomonas fluorescens* set forth herein as any of SEQ ID NOs:3-108.

In a preferred embodiment, HPPD polypeptides according to present invention and being tolerant to one or more HPPD inhibitor herbicides are equivalent to SEQ ID NO:1 (*Pseudomonas fluorescens*) beside the amino acids being replaced according to present invention, ie.

the respective HPPD polypeptide is identical to SEQ ID NO:1 but having (a) a proline at the amino acid position 335 of SEQ ID NO:1, (b) a histidine or an aspartic acid at amino acid position 336 of SEQ ID NO:1, and (c) a serine at amino acid position 337 of SEQ ID NO:1.

In a further preferred embodiment, HPPD polypeptides according to present invention being tolerant to one or more HPPD inhibitor herbicides are equivalent to SEQ ID NO:1 (*Pseudomonas fluorescens*) beside the amino acids being replaced according to present invention, ie., the respective HPPD polypeptide is identical to SEQ ID NO:1 but having one or more amino acid exchanges at the respective amino acid position according to Table 1, above, with the proviso that a proline exists at position 335 of SEQ ID NO:1, a histidine or an aspartic acid exists at position 336 of SEQ ID NO:1 and a serine exists at position 337 of SEQ ID NO:1.

In a further preferred embodiment, HPPD polypeptides according to present invention being tolerant to one or more HPPD inhibitor herbicides are equivalent to SEQ ID NO:1 (*Pseudomonas fluorescens*) beside the amino acids being replaced according to present invention, ie., the respective HPPD polypeptide is identical to SEQ ID NO:1 but having amino acid exchanges at respective amino acid position(s) as defined at Table 2 (below) at lines SEQ ID NO:7 to SEQ ID NO:19 and SEQ ID NO: 21 to SEQ ID NO:108.

In some embodiments, the nucleotide sequence of the invention (including isolated, recombinant and chimeric genes thereof, vectors, host cells, plants, plant parts, and seeds comprising the nucleic acid sequence, amino acid sequences and compositions thereof encoded by the nucleic acid sequence, as well as methods of using the nucleic acid sequence for increasing tolerance of a plant to HPPD inhibitor herbicides, particularly increased tolerance to HPPD inhibitor herbicides of the class of triketones (preferably benzobicyclon, sulcotrione, mesotrione, tembotrione, tefuryltrione, bicyclopyrone, fenquinotrione), diketonitriles, isoxazoles (preferably isoxaflutole) hydroxypyrazoles (preferably pyrazoxyfen, benzofenap, pyrazolynate, pyrasulfotole, topramezone, tolpyralate), N-(1,2,5-oxadiazol-3-yl) benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl) benzamide (hereinafter also named "Cmpd. 1"); 2-(methoxymethyl)-3-(methylsulfinyl)-N-(1-methyl-1H-tetrazol-5-yl)-4-(trifluoromethyl)benzamide, pyridazinone derivatives, oxoprazine derivatives, N-(triazol-2-yl)arylcarboxamides, triazinones, and pyrazolones encodes the amino acid sequence set forth in any one of SEQ ID NOs:3-108, and fragments and variants thereof that encode an HPPD inhibitor herbicide tolerance polypeptide.

A. Methods for Measuring HPPD Inhibitor Tolerance

Any suitable method for measuring tolerance to HPPD inhibitor herbicides can be used to evaluate the HPPD polypeptides of the invention. Tolerance can be measured by monitoring the ability of a cell or organism to survive a particular HPPD inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with HPPD inhibitor herbicide compared to such plants not treated with such herbicide (but where weeds have been removed or prevented by a mechanism other than application of the HPPD inhibitor herbicide). In some embodiments, tolerance can be measured according to a visible indicator phenotype of the cell or organism transformed with a nucleic acid comprising the gene coding for the respective HPPD polypeptide, or in an in vitro assay of the HPPD polypeptide, in the presence of different concentrations of the various HPPD inhibitor herbicides. Dose responses and relative shifts in dose responses associated with these indicator phenotypes (formation of brown color, growth inhibition, bleaching, herbicidal effect etc.) are conveniently expressed in terms, for example, of GR50 (concentration for 50% reduction of growth) or MIC (minimum inhibitory concentration) values where increases in values correspond to increases in inherent tolerance of the expressed HPPD polypeptide, in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed HPPD polypeptide. Herbicides can suitably be applied pre-emergence or post emergence.

In various embodiments, tolerance level of the nucleic acid or gene encoding an HPPD polypeptide according to the invention, or the HPPD polypeptide of the invention can be screened via transgenesis, regeneration, breeding and spray testing of a test plant such as tobacco, or a crop plant such as soybean, corn, or cotton. In line with the results obtained by such screening, such plants are more tolerant, desirably tolerant to at least 2 times the normal dose recommended for field applications, even more preferably tolerant up to 4 times the normal dose recommended for field applications, to HPPD inhibitor herbicides (e.g. HPPD inhibitor herbicides of the class of triketones (preferably benzobicyclon, sulcotrione, mesotrione, tembotrione, tefuryltrione, bicyclopyrone, fenquinotrione), diketonitriles, isoxazoles (preferably isoxaflutole), hydroxypyrazoles (preferably pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl) benzamide (hereinafter also named "Cmpd. 1"); 2-(methoxymethyl)-3-(methylsulfinyl)-N-(1-methyl-1H-tetrazol-5-yl)-4-(trifluoromethyl)benzamide, pyridazinone derivatives, oxoprazine derivatives, N-(triazol-2-yl)arylcarboxamides, triazinones, and pyrazolones than such plants that do not contain any exogenous gene encoding an HPPD polypeptide, or than plants that contain a gene comprising a reference HPPD polypeptide encoding DNA, for example, a *Pseudomonas fluorescens* HPPD-encoding DNA, under control of the same promoter as the nucleic acid encoding the HPPD polypeptide of present invention. Accordingly, the term "capable of increasing the tolerance of a plant to at least one herbicide acting on HPPD" denotes a tolerance by the plant expressing the HPPD of the invention to at least 1×, 2×, or 3×, or 4×, or greater, the normal field dose of the HPPD inhibitor herbicide as compared to a plant only expressing its endogenous HPPD or a plant expressing a reference HPPD polypeptide. In this regard, the term "herbicide acting on HPPD" is not limited to substances which are known and/or used as herbicides but to any substances which inhibit the catalytic activity of HPPD polypeptides.

The term "herbicide tolerance", "inhibitor tolerance", or "inhibitor insensitivity" means also the ability of an enzyme to perform its respective catalytic reaction in the presence of an inhibitor/herbicide or after an exposition to an inhibitor/herbicide. The herbicide tolerance of enzymes, i.e. their ability to resist the inhibitory effect of the herbicide, can be expressed qualitatively and quantitatively. Qualitatively, enzymes that tolerate different entities or even different classes of inhibitors have a high tolerance and vice versa. In quantitative terms, the tolerance of an enzyme compared to one herbicide can be expressed as the respective "residual activity" or "residual turnover" observed in one sample of this enzyme calculated as ratio of activities ($k_{app}$, kinetic measure) or total substrate turnover (change in signal, endpoint measurement) in the absence and presence of one inhibitor (Bergmeyer, H. U.: "Methods of enzymatic analysis", 1974). In various embodiments, for the determination of the residual activity, the apparent kinetic constant ($k_{app}$) of the determined substrate conversion can be measured as kinetic changes in absorbance at 320 nm in a coupled assay, in that homogentisate (HGA) formed by HPPD from HPP is directly converted into the well absorbing molecule maleylacetoacetate (MAA) by a second enzyme homogentisate dioxygenase (HGD), applied in excess uniformly in all assays. The $k_{cat}/k_M$ ratio of an enzymatic activity is proportional to the apparent kinetic constant $k_{app}$ and is proportional to $k_{cat}/k_M$*[E] ([E]=enzyme concentration). A competitive inhibitor exhibits an apparent increase in $k_M$ and thereby a reciprocal decrease in $k_{app}$ at non-saturating substrate concentrations. As both $k_{app}$ measurements in the presence and absence of inhibitor are performed by use of the identical enzyme sample, raw or purified, and thereby at the same enzyme concentration, the enzyme concentration eliminates from the calculation of residual activity and the ratio of both $k_{app}$ directly indicates the change of $k_M$ due to the inhibition. Noteworthy, this concept applies to enzyme/inhibitor pairs interacting in a "competitive inhibition" manner, probably correct for almost all polypeptide variants and inhibitors described. The inhibition constant ki for an enzyme and the respective inhibitor describes the binding strength of the inhibitor to this enzyme. An increased tolerance is given for ratios of 1.5, 2, 3, 4, 5, 7, 10, 20, 30, 40, 50, 100, 200 or higher and compared to a reference HPPD sequence in presence or absence of any respective HPPD inhibitor herbicide.

A specific, although non-limiting, type of assay that can be used to evaluate the HPPD polypeptide sequences of the invention is a colorimetric assay (as described, for example, see U.S. Pat. No. 6,768,044). In this assay, for example, *E. coli* cells containing the vector pSE420-HPPDx (HPPDx means any gene coding for a putative HPPD polypeptide; basic vector "pSE420" was obtained from Invitrogen Karlsruhe, Germany) or a modified version of pSE420 (pSE420(RI)NX)-HPPDx are producing soluble melanin-like pigments from the tyrosine catabolism when the over-expressed HPPD polypeptide is active. These melanin-like pigments are assayed in a liquid culture or by applying *E. coli* culture on LB-broth type solid agar. After 16 hours to 8 days at 20-30° C., the culture medium or agar wells which have been inoculated with an *E. coli* culture containing the empty vector pSE420 do not alter the color of the medium, or those which have been seeded with an *E. coli* culture containing a vector pSE420-HPPDx containing a gene coding for an inactive HPPD also do not alter the color of the medium, while the wells inoculated with an *E. coli* culture containing the vector pSE420-HPPDx coding for an active HPPD are brownish. In the presence of an HPPD inhibitor herbicide, this pigment production can be inhibited and the culture will not alter the color of the medium, unless an HPPD inhibitor herbicide tolerant HPPD polypeptide is expressed and active. It has been previously demonstrated that this test reflects the HPPD activity and HPPD inhibitor herbicide tolerance, whatever the origin of this activity is, and allows the identification of HPPD activities (U.S. Pat. No. 6,768,044), i.e. at a qualitative level.

B. Methods of Introducing Mutations into HPPD Sequences

In the mutated HPPD polypeptides encoded by the nucleic acid of the invention at least three amino acid have been replaced as defined above.

The replacement can be effected in the nucleic acid sequence which encodes the reference HPPD polypeptide as defined above by any means which is appropriate for replacing, in the said sequence, the codon which encodes the amino acid to be replaced with the codon which corresponds to the amino acid which is to replace it, with the said codons being widely described in the literature and well known to the skilled person.

Several molecular biological methods can be used to achieve this replacement. A useful method for preparing a mutated nucleic acid sequence according to the invention and the corresponding protein comprises carrying out site-directed mutagenesis on codons encoding one or more amino acids which are selected in advance. The methods for obtaining these site-directed mutations are well known to the skilled person and widely described in the literature (in particular: Directed Mutagenesis: A Practical Approach, 1991, Edited by M. J. McPHERSON, IRL PRESS), or are methods for which it is possible to employ commercial kits (for example the QUIKCHANGE™ lightening mutagenesis kit from Qiagen or Stratagene). After the site-directed mutagenesis, it is useful to select the cells which contain a mutated HPPD which is less sensitive to an HPPD inhibitor by using an appropriate screening aid. Appropriate screening methods to achieve this have been described above.

Alternatively, a DNA sequence encoding the reference HPPD polypeptide can be modified in silico to encode an HPPD polypeptide having one or more of the substitutions recited herein, and then synthesized de novo. This method is also well known in the art, described in the literature. The nucleotide sequence encoding the mutated HPPD polypeptide can be introduced into a host cell as described elsewhere herein.

C. Isolated Polynucleotides, and Variants and Fragments Thereof

In some embodiments, the present invention comprises isolated or recombinant, polynucleotides. The term "polynucleotide" corresponds to any genetic material of any length and any sequence, comprising single-stranded and double-stranded DNA and RNA molecules, including regulatory elements, structural genes, groups of genes, plasmids, whole genomes, and fragments thereof. A "recombinant" polynucleotide or polypeptide/protein, or biologically active portion thereof, as defined herein is no longer present in its original, native organism, such as when contained in a heterologous host cell or in a transgenic plant cell, seed or plant. In one embodiment, a recombinant polynucleotide is free of sequences (for example, protein encoding or regulatory sequences) that naturally flank the nucleic acid (i.e., sequences located at the 5' and 3' ends of the nucleic acid) in the genomic DNA of the organism from which the polynucleotide is derived. The term "recombinant" encompasses polynucleotides or polypeptides that have been manipulated with respect to the native polynucleotide or polypeptide, such that the polynucleotide or polypeptide differs (e.g., in chemical composition or structure) from what is occurring in nature. In another embodiment, a "recombinant" polynucleotide is free of internal sequences (i.e. introns) that naturally occur in the genomic DNA of the organism from which the polynucleotide is derived. A typical example of such polynucleotide is a so-called Complementary DNA (cDNA). For example, in various embodiments, the isolated HPPD inhibitor herbicide tolerance-encoding polynucleotide can contain less than about 5 kb, 4 kb, 3 kb, 2 kb, 1 kb, 0.5 kb, or 0.1 kb of nucleotide sequence that naturally flanks the polynucleotide in genomic DNA of the cell from which the polynucleotide is derived. Nucleic acid molecules of the invention include those that encode the HPPD of the invention. In some embodiments, the nucleic acid molecule of the invention is operably linked to a promoter capable of directing expression of the nucleic acid molecule in a host cell (e.g., a plant host cell or a bacterial host cell).

The present invention further contemplates exemplary variants and fragments of any nucleic acid sequence encoding the amino acid sequences set forth in any of SEQ ID NOs:3-108. A "fragment" of a polynucleotide may encode a biologically active portion of a polypeptide, or it may be a fragment that can be used as a hybridization probe or PCR primer using methods disclosed elsewhere herein. Polynucleotides that are fragments of a polynucleotide comprise at least about 15, 20, 50, 75, 100, 200, 300, 350, 400, 450, 500, 550, 600, 650, 700, 750, 800, 850, 900, 950, 1000, 1050, 1100, 1150, contiguous nucleotides, or up to the number of nucleotides present in a full-length polynucleotide disclosed herein depending upon the intended use (e.g., an HPPD nucleic acid described herein). By "contiguous" nucleotides are intended nucleotide residues that are immediately adjacent to one another.

Fragments of the polynucleotides of the present invention generally will encode polypeptide fragments that retain the biological activity of the full-length HPPD inhibitor herbicide tolerance protein; i.e., herbicide-tolerance activity. By "retains herbicide tolerance activity" is intended that the fragment will have at least about 30%, at least about 50%, at least about 70%, at least about 80%, 85%, 90%, 95%, 100%, 110%, 125%, 150%, 175%, 200%, 250%, at least about 300% or greater of the herbicide tolerance activity of the full-length HPPD inhibitor herbicide tolerance protein disclosed herein as SEQ ID NOs:3-108. Methods for measuring herbicide tolerance activity are well known in the art and exemplary methods are described herein. In a non-limiting example, a fragment of the invention will be tolerant to the same dose of an HPPD inhibitor herbicide, or tolerant to 1×, 2×, 3×, 4×, or higher dose of an HPPD inhibitor herbicide, or the fragments will be as or more tolerant based on ki between the fragment and SEQ ID NOs:3-108.

A fragment of a polynucleotide that encodes a biologically active portion of a polypeptide of the invention will encode at least about 150, 175, 200, 250, 300, 350 contiguous amino acids, or up to the total number of amino acids present in a full-length polypeptide of the invention. In a non-limiting example, a fragment of a polynucleotide that encodes a biologically active portion of an HPPD polypeptide having (a) a proline at the amino acid position corresponding to amino acid position 335 of SEQ ID NO:1 and (b) a histidine or an aspartic acid at the position corresponding to amino acid position 336 of SEQ ID NO:1 and (c) a serine at the position corresponding to amino acid position 337 of SEQ ID NO:1 and, optionally, one or more further amino acid substitutions at the positions corresponding to amino acid positions 204, 213, 264, 268, 270, 310, 315, 330, 331, 338, 339, 340, 344, 345 of SEQ ID NO:1, including the HPPD protein set forth in any of SEQ ID NOs:3-108.

The invention also encompasses variant polynucleotides as described supra. "Variants" of the polynucleotide also include those sequences that encode the HPPD of the invention but that differ conservatively because of the degeneracy of the genetic code, as well as those that are sufficiently identical. Variants of the present invention will retain HPPD polypeptide activity and HPPD herbicide inhibitor tolerance. The term "sufficiently identical" is intended a polypeptide or polynucleotide sequence that has at least about 53%, at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs using standard parameters. One of skill in the art will recognize that these values can be appropriately adjusted to determine corresponding identity of polypeptides encoded by two polynucleotides by taking into account codon degeneracy, amino acid similarity, reading frame positioning, and the like.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants that confer herbicide tolerance. These herbicide tolerance proteins are encompassed in the present invention and may be used in the methods of the present invention. Naturally occurring allelic variants can be identified with the use of well-known molecular biology techniques, such as polymerase chain reaction (PCR) and hybridization techniques as outlined below. Variant polynucleotides also include synthetically derived polynucleotides that have been generated, for example, by using site-directed or other mutagenesis strategies but which still encode the polypeptide having the desired biological activity.

The skilled artisan will further appreciate that changes can be introduced by further mutation of the polynucleotides of the invention thereby leading to further changes in the amino acid sequence of the encoded polypeptides, without altering the biological activity of the polypeptides. Thus, variant isolated polynucleotides can be created by introducing one or more additional nucleotide substitutions, additions, or deletions into the corresponding polynucleotide encoding the HPPD of the invention, such that 3-5, 1-7, 1-9, 1-11, 1-13, 1-15, or 1-17 amino acid substitutions, additions or deletions, or 3, 4, 5, 6, 7, 8, 9, 10, 11, 12, 13, 14, 15, 16 or 17 amino acid substitutions, additions or deletions, are introduced into the encoded polypeptide. Further mutations can be introduced by standard techniques, such as site-directed mutagenesis and PCR-mediated mutagenesis, or gene shuffling techniques. Such variant polynucleotides are also encompassed by the present invention.

Variant polynucleotides can be made by introducing mutations randomly along all or part of the coding sequence, such as by saturation mutagenesis or permutational mutagenesis, and the resultant mutants can be screened for the ability to confer herbicide tolerance activity to identify mutants that retain activity.

Additional methods for generating variants include subjecting a cell expressing a protein disclosed herein (or library thereof) to a specific condition that creates a stress to the activity of the protein. Specific conditions can include (but are not limited to) changes in temperature, changes in pH, changes in the concentrations of substrates or inhibitors, and changes in the buffer composition or their concentrations. The protein library can be subjected to these conditions during the time of protein expression (e.g. in *E. coli* or other host) or following creation of a protein extract, or following protein purification.

The functional or enzymatic activity of the protein library that has been subjected to a stress condition can then be compared to the reference protein to identify proteins with improved properties. This activity comparison can be carried out as part of a growth screen or alternatively as part of an enzymatic assay that quantifies the activity of the protein. The properties that can be identified as improved can include HPPD inhibitor herbicide tolerance, changes in kinetic constants (including KM, Ki, $k_{cat}$), protein stability, protein thermostability, or protein temperature and pH optimum.

D. Isolated Proteins and Variants and Fragments Thereof

Herbicide tolerance polypeptides are also encompassed within the present invention. A herbicide tolerance polypeptide includes preparations of polypeptides having less than about 30%, 20%, 10%, or 5% (by dry weight) of non-herbicide tolerance polypeptide (also referred to herein as a "contaminating protein"). In the present invention, "herbicide tolerance protein" is intended an HPPD polypeptide disclosed herein. Fragments, biologically active portions, and variants thereof are also provided, and may be used to practice the methods of the present invention.

"Fragments" or "biologically active portions" include polypeptide fragments comprising a portion of an amino acid sequence encoding an herbicide tolerance protein and that retains herbicide tolerance activity. A biologically active portion of an herbicide tolerance protein can be a polypeptide that is, for example, 10, 25, 50, 100 or more amino acids in length. Such biologically active portions can be prepared by recombinant techniques and evaluated for herbicide tolerance activity.

By "variants" is intended proteins or polypeptides having an amino acid sequence that is at least about 53%, 60%, 65%, about 70%, 75%, about 80%, 85%, 90%, 91%, 92%, 93%, 94%, 95%, 96%, 97%, 98% or 99% identical to any of the exemplary SEQ ID NOs:3-108, wherein said variant has HPPD polypeptide activity and HPPD inhibitor herbicide tolerance. One of skill in the art will recognize that these values can be appropriately adjusted to determine corresponding identity of polypeptides encoded by two polynucleotides by taking into account codon degeneracy, amino acid similarity, reading frame positioning, and the like.

For example, conservative amino acid substitutions may be made at one or more nonessential amino acid residues. A "nonessential" amino acid residue is a residue that can be altered from the reference sequence of a polypeptide without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g. alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine). Amino acid substitutions may be made in non-conserved regions that retain function. In general, such substitutions would not be made for conserved amino acid residues, or for amino acid residues residing within a conserved motif, where such residues are essential for polypeptide activity. However, one of skill in the art would understand that functional variants may have minor conserved or non-conserved alterations in the conserved residues.

Antibodies to the HPPD of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NOs:1-108 or a fragment thereof.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

E. Gene Stacking

In the commercial production of crops, it is desirable to eliminate under reliable pesticidal management unwanted plants (i.e. "weeds") from a field of crop plants. An ideal treatment would be one which could be applied to an entire field but which would eliminate only the unwanted plants while leaving the crop plants unaffected. One such treatment system would involve the use of crop plants which are tolerant to an herbicide so that when the herbicide is sprayed on a field of herbicide-tolerant crop plants, the crop plants would continue to thrive while non-herbicide-tolerant weeds are killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

While a number of herbicide-tolerant crop plants are presently commercially available, an issue that has arisen for many commercial herbicides and herbicide/crop combinations is that individual herbicides typically have incomplete spectrum of activity against common weed species. For most individual herbicides which have been in use for some time, populations of herbicide resistant weed species and biotypes have become more prevalent (see, e.g., Tranel and Wright (2002) *Weed Science* 50: 700-712; Owen and Zelaya (2005) *Pest Manag. Sci.* 61: 301-311). Transgenic plants which are tolerant to more than one herbicide have been described (see, e.g. WO2005/012515). However, improvements in every aspect of crop production, weed control options, extension of residual weed control, and improvement in crop yield are continuously in demand.

The HPPD protein or nucleotide sequence of the invention is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides that, according to their chemical structure, differ from HPPD inhibitor herbicides, and others which confer tolerance to certain insects, those which confer tolerance to certain diseases, DNAs that encodes RNAs that provide nematode or insect control, and the like.

Such genes are in particular described in published PCT Patent Applications WO91/02071 and WO95/06128 and in U.S. Pat. No. 7,923,602 and US Patent Application Publication No. 20100166723, each of which is herein incorporated by reference in its entirety.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769,061, 5,094,945, 4,940,835, 5,188,642, 4,971,908, 5,145,783, 5,310,667, 5,312,910, 5,627,061, 5,633,435), a gene encoding glyphosate-n-acetyltransferase (for example, U.S. Pat. Nos. 8,222,489, 8,088,972, 8,044,261, 8,021,857, 8,008,547, 7,999,152, 7,998,703, 7,863,503, 7,714,188, 7,709,702, 7,666,644, 7,666,643, 7,531,339, 7,527,955, and 7,405,074), or a gene encoding glyphosate oxydoreductase (for example, U.S. Pat. No. 5,463,175).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO2004/074443), and which is described in U.S. Pat. No. 6,566,587, hereinafter named double mutant maize EPSPS or 2mEPSPS, or the gene which encodes an EPSPS isolated from *Agrobacterium* and which is described by sequence ID No. 2 and sequence ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACES, particularly the mutants or variants of GRG23 as described in WO2008/100353, such as GRG23(ace3)R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. No. 5,510,471 or 5,633,448.

Exemplary herbicide tolerance traits that can be combined with the nucleic acid sequence of the invention further include at least one ALS (acetolactate synthase) inhibitor (WO2007/024782); a mutated *Arabidopsis* ALS/AHAS gene (U.S. Pat. No. 6,855,533); genes encoding 2,4-D-monooxygenases conferring tolerance to 2,4-D (2,4-dichlorophenoxyacetic acid) by metabolization (U.S. Pat. No. 6,153,401); and, genes encoding Dicamba monooxygenases conferring tolerance to dicamba (3,6-dichloro-2-methoxybenzoic acid) by metabolization (US 2008/0119361 and US 2008/0120739).

In various embodiments, the HPPD of the invention is stacked with one or more herbicide tolerant genes, including one or more additional HPPD inhibitor herbicide tolerant genes, and/or one or more genes tolerant to glyphosate and/or glufosinate. In one embodiment, the HPPD of the invention is combined with 2mEPSPS and bar.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO97/17432 & WO98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1A-Cry1F proteins described in U.S. Pat. Nos. 6,326,169; 6,281,016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO2002/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO2005/054479 and WO2005/054480, respectively), the Cry proteins as described in WO2001/47952, the VIP3Aa protein or a toxic fragment thereof as described in Estruch et al. (1996), Proc Natl Acad Sci USA. 28; 93(11):5389-94 and U.S. Pat. No. 6,291,156, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932 (e.g., Waterfield et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

In various embodiments, the HPPD sequence of the invention can be combined in plants with one or more genes conferring a desirable trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like.

Particularly useful transgenic events which may be combined with the genes of the current invention in plants of the same species (e.g., by crossing or by re-transforming a plant containing another transgenic event with a chimeric gene of the invention), include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946 Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671); Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-1 (brinjal, insect control, not deposited, described in WO 07/091277); Event FI117 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1), event 4114 (Maize, insect control, ATCC Accession No PTA-11506) WO201314901, event MON87411 (Maize, ATCC Accession No PTA-12669) WO2013169923, event A26-5 (Cotton, insect control) WO2013170398, event A2-6 (Cotton, insect control) WO2013170399, event 9582.816.15.1 (Soybean, insect control, herbicide tolerance), ATCC Accession No PTA-12588) WO2014004458, event 33121 (Maize, insect control, herbicide tolerance, ATCC Accession No PTA-13392) WO2014116854, event 32218 (Maize insect control, herbicide tolerance, ATCC Accession No PTA-13391) WO2014116989, event "SPT-7R-949D SPT-7R-1425D" (Rice male sterility) WO2014154115, event MON87751 (Soybean, ATCC Accession No. PYA-120166) WO2014201235, event "Pp009-401 Pp009-415 Pp009-469" (Turfgrass, ATCC Accession No PTA-120354, PTA-120353, PTA-120355) WO2015006774, event Bs2-X5 (Tomato, ATCC) WO2015017637, event MON87403 (Maize, grain yield, ATCC Accession No PTA-13584 WO2015053998, event 32218 (Maize, insect control, ATCC Accession No PTA-13391) WO2015112182.

F. Polynucleotide Constructs

The polynucleotides encoding the HPPD polypeptides of the present invention may be modified to obtain or enhance expression in plant cells. The polynucleotides encoding the polypeptides identified herein may be provided in expression cassettes for expression in the plant of interest. A "plant expression cassette" includes a DNA construct, including a recombinant DNA construct, that is capable of resulting in the expression of a polynucleotide in a plant cell. The cassette can include in the 5'-3' direction of transcription, a transcriptional initiation region (i.e. promoter, particularly a heterologous promoter) operably-linked to one or more polynucleotides of interest, and/or a translation and transcriptional termination region (i.e. termination region) functional in plants. The cassette may additionally contain at least one additional polynucleotide to be introduced into the organism, such as a selectable marker gene. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions.

In a further embodiment, the present invention relates to a chimeric gene comprising a coding sequence comprising heterologous the nucleic acid of the invention operably linked to a plant-expressible promoter and optionally a transcription termination and polyadenylation region. "Heterologous" generally refers to the polynucleotide or polypeptide that is not endogenous to the cell or is not endogenous to the location in the native genome in which it is present, and has been added to the cell by infection, transfection, microinjection, electroporation, microprojection, or the like. By "operably linked" is intended a functional linkage between two polynucleotides. For example, when a promoter is operably linked to a DNA sequence, the promoter sequence initiates and mediates transcription of the DNA sequence. It is recognized that operably linked polynucleotides may or may not be contiguous and, where used to reference the joining of two polypeptide coding regions, the polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the DNA sequence of the invention. Where the promoter is "native" or "analogous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natl. Acad. Sci. USA,* 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); the 35S promoter described in Kay et al. (1987) *Science* 236: 1299-1302; promoters of *Chlorella* virus methyltransferase genes (U.S. Pat. No. 5,563,328) and the full-length transcript promoter from figwort mosaic virus (FMV) (U.S. Pat. No. 5,378,619); the promoters from genes such as rice actin (McElroy et al. (1990) *Plant Cell* 2:163-171 and U.S. Pat. No. 5,641,876); ubiquitin (Christensen et al. (1989) *Plant Mol. Biol.* 12:619-632 and Christensen et al. (1992) *Plant Mol. Biol.* 18:675-689) and Grefen et al. (2010) *Plant J,* 64:355-365; pEMU (Last et al. (1991) *Theor. Appl. Genet.* 81:581-588); MAS (Velten et al. (1984) *EMBO J.* 3:2723-2730 and U.S. Pat. No. 5,510,474); maize H3 histone (Lepetit et al. (1992) *Mol. Gen. Genet.* 231:276-285 and Atanassova et al. (1992) *Plant J.* 2(3):291-300); *Brassica napus* ALS3 (PCT application WO97/41228); a plant ribulose-biscarboxylase/oxygenase (RuBisCO) small subunit gene; the circovirus (AU 689 311) or the Cassava vein mosaic virus (CsVMV, U.S. Pat. No. 7,053,205); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) *PNAS* 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.,* 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

In one embodiment of this invention, a promoter sequence specific for particular regions or tissues of plants can be used to express the HPPD proteins of the invention, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO92/17580), the albumin promoter (WO98/45460), the oleosin promoter (WO98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO98/45445). Multiple promoters can be used in the constructs of the invention, including in succession.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850, 019), the CaMV 35S enhancer element (U.S. Pat. Nos. 5,106,739 and 5,164,316) and the FMV enhancer element (Maiti et al. (1997) *Transgenic Res.* 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adh1 intron of maize or intron 1 of rice actin. See also PCT WO96/23898, WO2012/021794, WO2012/021797, WO2011/084370, and WO2011/028914.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in co-translational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; Joshi et al. (1987) *Nucleic Acid Res.* 15:9627-9639; and European Patent Application EP 0 633 317 A1.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that is expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the nucleotide of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

This plant expression cassette can be inserted into a plant transformation vector. By "transformation vector" is intended a DNA molecule that allows for the transformation of a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a polynucleotide construct designed for transfer between different host cells. "Expression vector"

refers to a vector that has the ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "polynucleotide of interest" (a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g., LBA4404, GV3101, EHA101, EHA105, etc.) can be used for plant transformation. The second plasmid vector is not necessary for introduction of polynucleotides into plants by other methods such as microprojection, microinjection, electroporation, polyethylene glycol, etc.

G. Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods. See, for example, the methods for transforming plant cells and regenerating plants described in: U.S. Pat. Nos. 4,459,355, 4,536,475, 5,464,763, 5,177,010, 5,187,073, EP 267,159 A1, EP 604 662 A1, EP 672 752 A1, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174 A1, EP 486 233 A1, EP 486 234 A1, EP 539 563 A1, EP 674 725 A1, WO91/02071, WO95/06128, WO2011/095460, WO2012006439A2, WO2012006443A2, WO2012015039A1, WO2012019660A1, WO2012021494A1, WO2012064827A1, WO2012075562A1, WO2012077664A1, WO2012083137A1, WO2012084962A1, WO2012092577A1, WO2012109947A1, WO2012129443A2, WO2012138629A2, WO2012139416A1, WO2012149011A1, WO2013014585A1, WO2013025670A1, WO2013033308A2, WO2013066007A1, WO2013077420A1, WO2013090734A1, WO2013149726A1, WO2013180311A1, WO2014029044A1, WO2014029045A1, WO2014062036A1, WO2014065857A1, WO2014100234A1, WO2014100406A1, WO2014123208A1, WO2014143304A1, WO2014144513A2, WO2014157541A1, WO2014200842A2, WO2015051083A1, WO2015077620A1, WO2015085990A1, WO2015099674A1, WO2015118640A1, WO2015119166A1, each of which is herein incorporated by reference, particularly with respect to the transformation methods described therein.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grow into mature plants and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The plant cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome. In various embodiments, the seed can be coated with at least one fungicide and/or at least one insecticide, at least one herbicide, and/or at least one safener, or any combination thereof.

H Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, N.Y.)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled $^{32}P$ target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by nucleotide sequences of the invention is then tested by hybridizing the filter to a radioactive probe derived by methods known in the art (Sambrook and Russell (2001) supra). RNA can also be detected and/or quantified using reverse transcriptase PCR as known in the art (e.g., Green and Sambrook (2012) Molecular Cloning: A Laboratory Manual, 4th Edition, Cold Spring Harbor Laboratory Press, Woodbury, N.Y.).

Western blot, ELISA, lateral flow testing, and biochemical assays and the like may be carried out on the transgenic plants to determine the presence of protein encoded by the herbicide tolerance gene by standard procedures (Sambrook and Russell (2001) supra) using antibodies that bind to one or more epitopes present on the herbicide tolerance protein.

In one aspect of the invention, the HPPD genes described herein are useful as markers to assess transformation of bacterial or plant cells.

I. Use as a Marker for Transformation

The invention also relates to the use, in a method for transforming plants, of a nucleic acid which encodes an HPPD according to the invention as a marker gene or as a coding sequence which makes it possible to confer to the plant tolerance to herbicides which are HPPD inhibitors, and the use of one or more HPPD inhibitor(s) on plants comprising a nucleic acid sequence encoding an HPPD according to the invention. See, for example, U.S. Pat. No. 6,791,014, which is herein incorporated by reference in its entirety.

In this embodiment, an HPPD inhibitor can be introduced into the culture medium of the competent plant cells so as to bleach said cells before the transformation step. The bleached competent cells are then transformed with the gene for tolerance to HPPD inhibitors, as a selection marker, and the transformed cells which have integrated said selection marker into their genome become green, enabling them to be selected. Such a process makes it possible to decrease the time required for selecting the transformed cells.

Thus, one embodiment of the present invention consists of a method for transforming plant cells by introducing a heterologous gene into said plant cells with a gene for tolerance to HPPD inhibitors as selection markers, wherein the method comprises preparing and culturing competent plant cells capable of receiving the heterologous gene in a suitable medium and introducing a suitable amount of HPPD inhibitor into the suitable culture medium of the competent plant cells. The competent cells are then transformed with the heterologous gene and the selection marker, and the transformed cells comprising the heterologous gene are grown in a suitable medium and transformants selected therefrom. The transformed cells can then be regenerated into a fertile transformed plant.

J. Plants and Plant Parts

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), *sorghum*, wheat, sunflower, tomato, crucifers, peppers, potato, cotton, rice, soybean, sugar beet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to tomatoes, lettuce, green beans, lima beans, peas, and members of the genus *Curcumis* such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Crop plants are also of interest, including, for example, maize, *sorghum*, wheat, sunflower, tomato, crucifers, peppers, potato, cotton, rice, soybean, sugar beet, sugarcane, tobacco, barley, oilseed rape, etc.

This invention is suitable for any member of the monocot plant family including, but not limited to, maize, rice, barley, oats, wheat, *sorghum*, rye, sugarcane, pineapple, yams, onion, banana, coconut, and dates K. Methods for Increasing Plant Yield Methods for increasing plant yield are provided. The methods comprise providing a plant comprising, or introducing into a plant or plant cell, a polynucleotide comprising a nucleotide sequence encoding an HPPD of the invention, growing the plant or a seed thereof in a field, and producing a harvest from said plants or seeds. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant comprising an HPPD sequence of the invention is treated with an effective concentration of an HPPD inhibitor herbicide, such as one or more HPPD inhibitor herbicide(s) selected from the group consisting of HPPD inhibitor herbicides of the class of triketones (preferably benzobicyclon, sulcotrione, mesotrione, tembotrione, tefuryltrione, bicyclopyrone, fenquinotrione), diketonitriles, isoxazoles (preferably isoxaflutole), hydroxypyrazoles (preferably pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl)benzamide (hereinafter also named "Cmpd. 1"); 2-(methoxymethyl)-3-(methylsulfinyl)-N-(1-methyl-1H-tetrazol-5-yl)-4-(trifluoromethyl)benzamide, pyridazinone derivatives, oxoprazine derivatives, N-(triazol-2-yl)arylcarboxamides, triazinones, and pyrazolones, where the herbicide application results in enhanced plant yield.

Methods for conferring herbicide tolerance in a plant or plant part are also provided. In such methods, a nucleotide sequence encoding an HPPD of the invention is introduced into the plant, wherein expression of the polynucleotide results in HPPD inhibitor herbicide tolerance. Plants produced via this method can be treated with an effective concentration of an herbicide (such as one or more HPPD inhibitor herbicide(s) selected from the group consisting of HPPD inhibitor herbicides of the class of triketones (preferably benzobicyclon, sulcotrione, mesotrione, tembotrione, tefuryltrione, bicyclopyrone, fenquinotrione), diketonitriles, isoxazoles (preferably isoxaflutole), hydroxypyrazoles (preferably pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl)benzamide (hereinafter also named "Cmpd. 1"); 2-(methoxymethyl)-3-(methylsulfinyl)-N-(1-methyl-1H-tetrazol-5-yl)-4-(trifluoromethyl)benzamide, pyridazinone derivatives oxoprazine derivatives, N-(triazol-2-yl)arylcarboxamides, triazinones, and pyrazolones and display an increased tolerance to the herbicide. An "effective concentration" of an herbicide in this application is an amount sufficient to slow or stop the growth of plants or plant parts that are not naturally tolerant or rendered tolerant to the herbicide.

L. Methods of Controlling Weeds in a Field

The present invention therefore also relates to a method of controlling undesired plants or for regulating the growth of plants in crops of plants comprising a nucleotide sequence encoding an HPPD polypeptide according to the invention, where one or more HPPD inhibitor herbicides, for example, one or more HPPD inhibitor herbicides selected from the class of triketones (preferably benzobicyclon, sulcotrione, mesotrione, tembotrione, tefuryltrione, bicyclopyrone, fenquinotrione), diketonitriles, isoxazoles (preferably isoxaflutole), hydroxypyrazoles (preferably pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl)benzamide (hereinafter also named "Cmpd. 1"); 2-(methoxymethyl)-3-(methylsulfinyl)-N-(1-methyl-1H-tetrazol-5-yl)-4-(trifluoromethyl)benzamidepyridazinone derivatives, oxoprazine derivatives, N-(triazol-2-yl)arylcarboxamides, triazinones, and pyrazolones, are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, an effective concentration of one or more HPPD inhibitor herbicide(s), for example, one or more HPPD inhibitor herbicides selected from the group consisting of HPPD inhibitor herbicides of the class of triketones (preferably benzobicyclon, sulcotrione, mesotrione, tembotrione, tefuryltrione, bicyclopyrone, fenquinotrione), diketonitriles, isoxazoles (preferably isoxaflutole), hydroxypyrazoles (preferably pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide; 2-chloro-3-(methylsulfanyl)-N-(1-methyl-1H-tetrazol-5-yl)-4-(trifluoromethyl)benzamide (hereinafter also named "Cmpd. 1");

2-(methoxymethyl)-3-(methylsulfinyl)-N-(1-methyl-1H-tetrazol-5-yl)-4-(trifluoromethyl)benzamide, pyridazinone derivatives, oxoprazine derivatives, N-(triazol-2-yl)arylcarboxamides, triazinones, and pyrazolones, can be applied for example pre-planting (if appropriate also by incorporation into the soil), pre-emergence or post-emergence, and may be combined with the application of other herbicides to which the crop is naturally tolerant, or to which it is resistant via expression of one or more other herbicide resistance transgenes. See, e.g., U.S. App. Pub. No. 2004/0058427 and PCT App. Pub. No. WO98/20144. By "effective concentration" is intended the concentration which controls the growth or spread of weeds or other untransformed plants without significantly affecting the HPPD inhibitor-tolerant plant or plant seed. Those of skill in the art understand that application of herbicides can take many different forms and can take place at many different times prior to and/or throughout the seed planting and growth process. "Pre-emergent" application refers to an herbicide which is applied to an area of interest (e.g., a field or area of cultivation) before a plant emerges visibly from the soil. "Post-emergent" application refers to an herbicide which is applied to an area after a plant emerges visibly from the soil. In some instances, the terms "pre-emergent" and "post-emergent" are used with reference to a weed in an area of interest, and in some instances these terms are used with reference to a crop plant in an area of interest. When used with reference to a weed, these terms may apply to a particular type of weed or species of weed that is present or believed to be present in the area of interest. "Pre-plant incorporation" of an herbicide involves the incorporation of compounds into the soil prior to planting.

Thus, the present invention comprises a method of controlling weeds in a field comprising planting in a field a plant or a seed thereof comprising an HPPD polypeptide of present invention and applying to said plant or area surrounding said plant an effective concentration of one or more HPPD inhibitor herbicides.

In one embodiment of this invention, a field to be planted with plants (such as soybean, cotton, corn, or wheat plants, e.g.) containing an HPPD nucleotide sequence of the invention, can be treated with an HPPD inhibitor herbicide, such as isoxaflutole (IFT), before the plants are planted or the seeds are sown, which cleans the field of weeds that are killed by the HPPD inhibitor herbicide, allowing for no-till practices, followed by planting or sowing of the plants in that same pre-treated field later on (burndown application using an HPPD inhibitor herbicide). The residual activity of IFT will also protect the emerging and growing plants from competition by weeds in the early growth stages. Once the plants have a certain size, and weeds tend to re-appear, glufosinate or glyphosate, or an HPPD inhibitor herbicide or a mixture of an HPPD inhibitor herbicide with another herbicide such as glyphosate, can be applied as post-emergent herbicide over the top of the plants, when such plants are tolerant to said herbicides.

In another embodiment of this invention, a field in which seeds containing an HPPD nucleotide sequence of the invention were sown, can be treated with an HPPD inhibitor herbicide, such as IFT, before the plants emerge but after the seeds are sown (the field can be made weed-free before sowing using other means, typically conventional tillage practices such as ploughing, chissel ploughing, or seed bed preparation), where residual activity will keep the field free of weeds killed by the herbicide so that the emerging and growing plants have no competition by weeds (pre-emergence application of an HPPD inhibitor herbicide). Once the plants have a certain size, and weeds tend to re-appear, glufosinate or glyphosate, or an HPPD inhibitor herbicide or a mixture of an HPPD inhibitor herbicide with another herbicide such as glyphosate, can be applied as post-emergent herbicide over the top of the plants, when such plants are tolerant to said herbicides.

In another embodiment of this invention, plants containing an HPPD nucleotide sequence of the invention, can be treated with an HPPD inhibitor herbicide, over the top of the plants that have emerged from the seeds that were sown, which cleans the field of weeds killed by the HPPD inhibitor herbicide, which application can be together with (e.g., in a spray tank mix), followed by or preceded by a treatment with glyphosate or glufosinate as post-emergent herbicide over the top of the plants (post-emergence application of an HPPD inhibitor herbicide (with or without glyphosate)), when such plants are tolerant to such herbicides.

Examples of individual representatives of the monocotyledonous and dicotyledonous weeds which can be controlled with an HPPD inhibitor herbicide include:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

HPPD inhibitor herbicides useful in the present invention, including but not limited to HPPD inhibitor herbicides of the class of triketones (preferably benzobicyclon, sulcotrione, mesotrione, tembotrione, tefuryltrione, bicyclopyrone, fenquinotrione), diketonitriles, isoxazoles (preferably isoxaflutole), hydroxypyrazoles (preferably pyrazoxyfen, benzofenap, pyrazolynate, pyrasulfotole, topramezone, tolpyralate), N-(1,2,5-oxadiazol-3-yl)benzamides, N-(1,3,4-oxadiazol-2-yl)benzamides (preferably 2-methyl-N-(5-methyl-1,3,4-oxadiazol-2-yl)-3-(methylsulfonyl)-4-(trifluoromethyl)benzamide (hereinafter also named "Cmpd. 2"), N-(tetrazol-5-yl)- or N-(triazol-5-yl)arylcarboxamides (preferably 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl) benzamide; 2-chloro-3-(methylsulfanyl)-N-(1-methyl-1H-tetrazol-5-yl)-4-(trifluoromethyl)benzamide (hereinafter also named "Cmpd. 1"); 2-(methoxymethyl)-3-(methylsulfinyl)-N-(1-methyl-1H-tetrazol-5-yl)-4-(trifluoromethyl)benzamide, pyridazinone derivatives, oxoprazine derivatives, N-(triazol-2-yl)arylcarboxamides, triazinones, and pyrazolones, can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], Volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], Volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

M. Methods of Introducing Gene of the Invention into Another Plant

Also provided herein are methods of introducing the HPPD nucleotide sequence of the invention into another plant. The HPPD nucleotide sequence of the invention, or a fragment thereof, can be introduced into second plant by recurrent selection, backcrossing, pedigree breeding, line selection, mass selection, mutation breeding and/or genetic marker enhanced selection.

Thus, in one embodiment, the methods of the invention comprise crossing a first plant comprising an HPPD nucleotide sequence of the invention with a second plant to produce F1 progeny plants and selecting F1 progeny plants that are tolerant to an HPPD inhibitor herbicide or that comprise the HPPD nucleotide sequence of the invention. The methods may further comprise crossing the selected progeny plants with the first plant comprising the HPPD nucleotide sequence of the invention to produce backcross progeny plants and selecting backcross progeny plants that are tolerant to an HPPD inhibitor herbicide or that comprise the HPPD nucleotide sequence of the invention. Methods for evaluating HPPD inhibitor herbicide tolerance are provided elsewhere herein. The methods may further comprise repeating these steps one or more times in succession to produce selected second or higher backcross progeny plants that are tolerant to an HPPD inhibitor herbicide or that comprise the HPPD nucleotide sequence of the invention.

Any breeding method involving selection of plants for the desired phenotype can be used in the method of the present invention. In some embodiments, the F1 plants may be self-pollinated to produce a segregating F2 generation. Individual plants may then be selected which represent the desired phenotype (e.g., HPPD inhibitor herbicide tolerance) in each generation (F3, F4, F5, etc.) until the traits are homozygous or fixed within a breeding population.

The second plant can be a plant having a desired trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like. The second plant may be an elite event as described elsewhere herein.

In various embodiments, plant parts (whole plants, plant organs (e.g., leaves, stems, roots, etc.), seeds, plant cells, propagules, embryos, and the like) can be harvested from the resulting cross and either propagated or collected for downstream use (such as food, feed, biofuel, oil, flour, meal, etc).

N. Methods of Obtaining a Plant Product

The present invention also relates to a process for obtaining a commodity product, comprising harvesting and/or milling the grains from a crop comprising an HPPD sequence of the invention to obtain the commodity product. Agronomically and commercially important products and/or compositions of matter including but not limited to animal feed, commodities, and plant products and by-products that are intended for use as food for human consumption or for use in compositions and commodities that are intended for human consumption, particularly devitalized seed/grain products, including a (semi-)processed products produced from such grain/seeds, wherein said product is or comprises whole or processed seeds or grain, animal feed, corn or soy meal, corn or soy flour, corn, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans (raw, roasted, or as edamame), soy yogurt, soy cheese, tofu, yuba, as well as cooked, polished, steamed, baked or parboiled grain, and the like are intended to be within the scope of the present invention if these products and compositions of matter contain detectable amounts of the nucleotide and/or amino acid sequences set forth herein as being diagnostic for any plant containing such nucleotide sequences.

The following examples are offered by way of illustration and not by way of limitation.

EXPERIMENTAL

Overview

Example 1: Creation of mutated HPPD polypeptides by site-directed mutagenesis

Example 2: Cloning, expression, and purification of recombinant wild-type and mutant HPPD polypeptides Example 3: HPPD enzyme assay to analyse mutant HPPD polypeptides with improved HPPD inhibitor herbicide tolerance Example 4: Improved herbicide tolerance mediated by residue exchanges in HPPD polypeptides Example 5: Brown Color assay to test for mutant HPPD polypeptides, tolerant to HPPD inhibitor herbicides Example 6: Soybean transformation and tolerance of the T0 soybean plants Example 7: Cotton T0 plant establishment and selection Example 8: Transformation of Maize Plant Cells by *Agrobacterium*-Mediated Transformation Example 9: Tolerance of T1 soybean plants to HPPD inhibitor herbicides/Field Trials

Example 1. Creation of Mutated HPPD Polypeptides by Site-Directed Mutagenesis The *Pseudomonas fluorescens* HPPD nucleotide sequence (SEQ ID NO:109) as described in WO2009/144079 encoding the HPPD polypeptide corresponding to SEQ ID NO:1 was cloned according to well known methods in the art and as described in WO2014/043435. Subsequent site-saturated mutagenesis, site-directed mutagenesis and combinatorial variants with one or more mutations of the nucleic acid encoding sequence of wild-type PfHPPD polypeptide encoding the recombinant HPPD polypeptide corresponding to SEQ ID NO: 1 were carried out using standard PCR-based technologies well known in the art (and as described likewise in WO2014/043435). All designed and synthesized mutant clones were confirmed by DNA sequencing using plasmid specific oligonucleotides. Table 2, below, summarizes the exemplary mutant HPPD polypeptides (SEQ ID NO:2-SEQ ID NO:108).

TABLE 2

Overview of exemplary amino acid exchanges corresponding to amino acid position in SEQ ID NO: 1.

| SEQ ID | Amino acid position relative to HPPD polypeptide SEQ ID NO: 1 | | | | | | | | | | | | | | | | |
|---|---|---|---|---|---|---|---|---|---|---|---|---|---|---|---|---|---|
| NO: | 204 | 213 | 264 | 268 | 270 | 310 | 315 | 330 | 331 | 335 | 336 | 337 | 338 | 339 | 340 | 344 | 345 |
| 1 | A | R | M | P | T | Q | T | D | D | E | G | N | F | K | A | S | I |
| 2 | | | | | | | | | | P | W | | | A | Q | | |
| 3 | | | | | | | | | | P | | | | | | | |
| 4 | | | | | | | | | | | | S | | | | | |
| 5 | | | | | | | | | | P | | S | | | | | |
| 6 | | | | | | | | | | P | D | | | | | | |
| 7 | | | | | | | | | | P | D | S | | | | | |
| 8 | | | | | | | | | | P | D | S | | | V | | |
| 9 | | | | | | | | | | P | D | S | | | | | V |
| 10 | | | | | | | | | | P | D | S | | | V | | V |
| 11 | | | | | | | | H | | P | D | S | | | | | |
| 12 | | | | | | | | H | | P | D | S | | | V | | |
| 13 | | | | | | | | H | | P | D | S | | | | | V |
| 14 | | | | | | | | H | | P | D | S | | | V | | V |
| 15 | | | | S | S | | | | | P | D | S | | | V | | V |
| 16 | | | | S | S | | | | | P | D | S | | | V | | K |
| 17 | | | | G | E | | | | | P | D | S | | | V | | V |
| 18 | | | R | | | | | H | | P | D | S | | | V | | |
| 19 | | | R | G | E | | | H | | P | D | S | | | V | | V |
| 20 | | | | | | | | | | P | H | | | | | | |
| 21 | | | | | | | | | | P | H | S | | | | | |
| 22 | | | | | | | | | | P | H | S | | | V | | |
| 23 | | | | | | | | | | P | H | S | | | | | V |
| 24 | | | | | | | | | | P | H | S | | | V | | V |
| 25 | | | | | | | | H | | P | H | S | | | | | |
| 26 | | | | | | | | H | | P | H | S | | | V | | |
| 27 | | | | | | | | H | | P | H | S | | | | | V |
| 28 | | | | | | | | H | | P | H | S | | | V | | V |
| 29 | | | | S | S | | | | | P | H | S | | | V | | V |

TABLE 2-continued

Overview of exemplary amino acid exchanges corresponding to amino acid position in SEQ ID NO: 1.

| SEQ ID | Amino acid position relative to HPPD polypeptide SEQ ID NO: 1 | | | | | | | | | | | | | | | | |
|---|---|---|---|---|---|---|---|---|---|---|---|---|---|---|---|---|---|
| NO: | 204 | 213 | 264 | 268 | 270 | 310 | 315 | 330 | 331 | 335 | 336 | 337 | 338 | 339 | 340 | 344 | 345 |
| 30 | | | | S | S | | | | | P | H | S | | | V | | K |
| 31 | | | | G | E | | | | | P | H | S | | | V | | V |
| 32 | | | | R | E | | | | | P | H | S | | | V | | V |
| 33 | | | | G | E | | | | | P | D | S | | | R | | V |
| 34 | | | | G | E | | | H | | P | D | S | | | R | | K |
| 35 | | | | G | E | | | | | P | D | S | | | R | | K |
| 36 | | | R | G | E | | | H | | P | D | S | | | V | | M |
| 37 | | | | G | R | | | H | | P | D | S | | | V | | K |
| 38 | | | | G | E | | | V | | P | D | S | | | V | | V |
| 39 | L | | | G | E | | | | | P | D | S | | | V | | V |
| 40 | M | | | G | E | | | | | P | D | S | | | V | | V |
| 41 | S | | | G | E | | | | | P | D | S | | | V | | V |
| 42 | T | | | G | E | | | | | P | D | S | | | V | | V |
| 43 | | K | | G | E | | | | | P | D | S | | | V | | V |
| 44 | | L | | G | E | | | | | P | D | S | | | V | | V |
| 45 | | | | G | E | | R | | | P | D | S | | | V | | V |
| 46 | | | | G | E | | M | | | P | D | S | | | V | | V |
| 47 | | | | G | E | | H | | | P | D | S | | | V | | V |
| 48 | | | | G | E | | | | H | P | D | S | | | V | | V |
| 49 | | | | G | E | | | | I | P | D | S | | | V | | V |
| 50 | | | | G | E | | | | P | P | D | S | | | V | | V |
| 51 | | | | G | E | | | | L | P | D | S | | | V | | V |
| 52 | | | | G | E | | | | S | P | D | S | | | V | | V |
| 53 | | | | G | E | | | | | P | D | S | V | | V | | V |
| 54 | | | | G | E | | | | | P | D | S | | A | V | | V |
| 55 | | | | G | E | | | | | P | D | S | | E | V | | V |
| 56 | | | | G | E | | | | | P | D | S | | R | V | | V |
| 57 | | | | G | E | | | | | P | D | S | | T | V | | V |
| 58 | | | | G | E | | | | | P | D | S | | | V | P | V |
| 59 | | | | G | E | | | | | P | D | S | | | V | R | V |
| 60 | | | R | G | E | | | H | | P | D | S | | | V | Q | V |
| 61 | | | R | G | E | | | H | | P | D | S | | | V | P | V |
| 62 | | | R | G | E | | | H | | P | D | S | | | V | R | V |
| 63 | | | | G | | | | | | P | D | S | | | V | | V |
| 64 | | | | G | E | | | | | P | D | S | | | V | | V |
| 65 | | | | G | E | | | | | P | D | S | | | V | | V |

TABLE 2-continued

Overview of exemplary amino acid exchanges corresponding to amino acid position in SEQ ID NO: 1.

| SEQ ID NO: | Amino acid position relative to HPPD polypeptide SEQ ID NO: 1 | | | | | | | | | | | | | | | | |
|---|---|---|---|---|---|---|---|---|---|---|---|---|---|---|---|---|---|
| | 204 | 213 | 264 | 268 | 270 | 310 | 315 | 330 | 331 | 335 | 336 | 337 | 338 | 339 | 340 | 344 | 345 |
| 66 | | | | G | E | | | | | P | D | S | | | V | | V |
| 67 | | | K | G | E | | | | | P | D | S | | | V | | V |
| 68 | | | L | G | E | | | | | P | D | S | | | V | | V |
| 69 | | | Q | G | E | | | | | P | D | S | | | V | | V |
| 70 | | | R | G | E | | | | | P | D | S | | | V | | V |
| 71 | | | | | E | | | | | P | D | S | | | V | | V |
| 72 | | | | R | E | | | | | P | D | S | | | V | | V |
| 73 | | | | S | E | | | | | P | D | S | | | V | | V |
| 74 | | | | G | L | | | | | P | D | S | | | V | | V |
| 75 | | | | G | P | | | | | P | D | S | | | V | | V |
| 76 | | | | G | R | | | | | P | D | S | | | V | | V |
| 77 | | | | G | S | | | | | P | D | S | | | V | | V |
| 78 | | | | G | E | | | A | | P | D | S | | | V | | V |
| 79 | | | | G | E | | | F | | P | D | S | | | V | | V |
| 80 | | | | G | E | | | G | | P | D | S | | | V | | V |
| 81 | | | | G | E | | | | | P | D | S | | | | | V |
| 82 | | | | G | E | | | | | P | D | S | | | E | | V |
| 83 | | | | G | E | | | | | P | D | S | | | G | | V |
| 84 | | | | G | E | | | | | P | D | S | | | L | | V |
| 85 | | | | G | E | | | | | P | D | S | | | M | | V |
| 86 | | | | G | | | | | | P | D | S | | | Q | | V |
| 87 | | | | G | | | | | | P | D | S | | | V | | A |
| 88 | | | | G | | | | | | P | D | S | | | V | | |
| 89 | | | | G | | | | | | P | D | S | | | V | | K |
| 90 | | | | G | | | | | | P | D | S | | | V | | M |
| 91 | | | | G | | | | | | P | D | S | | | V | | R |
| 92 | | | R | G | | | H | | | P | D | S | | | V | | A |
| 93 | | | R | G | | | H | | | P | D | S | | | V | | |
| 94 | | | R | G | | | H | | | P | D | S | | | V | | K |
| 95 | | | R | G | | | H | | | P | D | S | | | V | | R |
| 96 | | K | | G | | | | | | P | H | S | | | V | | V |
| 97 | | | | G | | | H | S | | P | D | S | | | V | | K |
| 98 | | | | G | | | H | S | | P | D | S | | | R | | K |
| 99 | | | | G | | | | | | P | D | S | V | | R | | V |
| 100 | | | L | G | | | H | | | P | D | S | | | V | Q | M |
| 101 | | | L | G | | R | | | | P | D | S | | | V | Q | M |

TABLE 2-continued

Overview of exemplary amino acid exchanges corresponding to amino acid position in SEQ ID NO: 1.

| SEQ ID | Amino acid position relative to HPPD polypeptide SEQ ID NO: 1 | | | | | | | | | | | | | | | | |
|---|---|---|---|---|---|---|---|---|---|---|---|---|---|---|---|---|---|
| NO: | 204 | 213 | 264 | 268 | 270 | 310 | 315 | 330 | 331 | 335 | 336 | 337 | 338 | 339 | 340 | 344 | 345 |
| 102 | | | L | R | | R | | | | P | H | S | | | V | Q | M |
| 103 | | K | L | G | | R | | | | P | H | S | | | V | Q | M |
| 104 | | K | L | G | | | | | | P | H | S | | | V | Q | M |
| 105 | | K | L | G | | | | | | P | H | S | | | R | Q | M |
| 106 | | | L | G | | | H | P | | P | D | S | | | V | Q | M |
| 107 | | K | | G | | | | | | P | H | S | V | | R | | V |
| 108 | | | | G | | M | H | | | P | D | S | | | V | | M |

For clarity, empty cells at the respective amino acid position in SEQ ID NO:2 to NO:108 are defined as identical to the amino acids corresponding to SEQ ID NO:1, highlighting only the exchanges in the mutant HPPD polypeptides. The mutant HPPD polypeptides represented here are examples by a way of illustration, not by a way of limitation.

Example 2: Cloning, Expression, and Purification of Recombinant Wild-Type and Mutant HPPD Polypeptides All resulting nucleic acid encoding sequences of wild-type and mutant HPPD encoding the recombinant HPPD polypeptide were cloned, produced and purified using methods well known in the art (Sambrook et al., Molecular Cloning: A Laboratory Manual, 3rd ed., CSH Laboratory Press, 2001, Cold Spring Harbor, N.Y.). All resulting nucleic acid encoding sequences were cloned into pSE420(RI)NX fused with an N-terminal His-tag (encoding the amino acid sequence M1-A2-H3-H4-H5-H6-H7-H8-), as described in WO2014/043435, and were expressed in *Escherichia coli* strain BL21 (DE3) (New England Biolabs, Frankfurt, Germany). For clarity, all listed positions with the respective amino acid exchanges from mutant HPPD polypeptides in Tables 1 to 5, and Table 7 corresponding to SEQ ID NO:2 to SEQ ID NO:108 in this invention, refer to the native wild-type HPPD amino acid sequence without the N-terminal His-tag corresponding to SEQ ID NO:1.

For the generation of purified HPPD polypeptide samples, cells were grown for 3 h at 37° C. in 5 ml LB medium containing 100 μg/ml ampicillin in a 50 ml shaker flask at 140 rpm. One ml of this starter culture was used as inoculum for the expression culture. Cells were grown for about 3 h at 37° C. in 100 ml LB medium containing 100 μg/ml ampicillin and 150 mM Hepes (Merck, Darmstadt, Germany) in a 500 ml shaker flask at 120 rpm. At an OD600 of about 0.6, IPTG (Roth, Karlsruhe, Germany) was added to a concentration of 0.4 mM. After further growth for 60 min at 37° C., the temperature was reduced to 28° C. and growth continued for another 18 h at 140 rpm. Cells were harvested by centrifugation at 4° C., 3200 g for 30 min in 50 ml Falcon tubes and cell pellets were stored at −80° C. Cells were lysed and his-tagged protein was purified according to manufacturer protocol of the used Ni-NTA Fast Start Kit (Qiagen, Hilden, Germany) with following adaptions for increased yield: cells from 50 ml culture were lysed in 4 ml and lysate supernatant was generated by centrifugation for 15 min at 18000 g. The amount of matrix in the columns was increased by addition of 1 ml of NiNTA Superflow (Qiagen, Hilden, Germany) each and extensively re-buffered into 20 mM Tris (pH 7.6) (Merck, Darmstadt, Germany) Lysate supernatant was applied and His-tagged protein was bound to the Ni-NTA matrix by incubation for 1 h at 4° C.

The resulting protein samples were re-buffered into 20 mM Tris, 20% Glycerol (pH 7.8) (Sigma-Aldrich, St. Louis, USA) by use of Zeba™ Spin Desalting Columns, 7K MWCO, 10 mL (Thermo Fisher Scientific, Waltham, USA) and analysed for protein concentration and purity by Abs280 (NANODROP 8000, Thermo Fisher Scientific, Waltham, USA) and SDS-PAGE. The concentrations of purified proteins were generally in the range of 0.6-4.6 mg/ml by an estimated purity of about 90%.

For the generation of crude HPPD polypeptide extract in micro titer plates (MTP) for the determination of residual activity in inhibition assays, cells were grown in 40 or 150 μl LB medium containing 1% Glucose (Merck, Darmstadt, Germany) and 100 μg/ml ampicillin in a standard 96 well plate (Thermo Fisher Scientific, Waltham, USA) incubated for about 18 h in a humidity incubator at 37° C.

30 μl of this starter culture were added to 600 μl LB medium containing 100 μg/ml ampicillin and 150 mM Hepes (Merck, Darmstadt, Germany) as inoculum for the expression culture in 96 well plates (2 ml deep wells; HJ Bioanalytik, Erkelenz, Germany) The plates were sealed by an aluminium foil, and cells were incubated for 5 h at 37° C. on a plate shaker at 750 rpm. The expression was induced by addition of IPTG in a final concentration of 1 mM followed by further sealed incubation for about 18 h at 30° C. on a plate shaker at 750 rpm.

Cells were harvested by centrifugation at 4° C., 2500 g for 15 min discarding the supernatant. Cell pellets were stored at −80° C. and lysed in 250 μl 1× BugBuster® (Merck, Darmstadt, Germany) in 140 mM Tris (pH 7.8), with 1:25000 diluted BNase® (Qiagen, Hilden, Germany) by incubation of the resuspended cells for 30 min at 4° C. and 1000 rpm. Lysates were clarified by centrifugation for 15 min at 4° C., 2500 g, and 150 μl supernatant were transferred in standard 96 well plate (Thermo Fisher Scientific, Waltham, USA) for subsequent testing in quadruplets.

Example 3: HPPD Enzyme Assay to Analyse Mutant HPPD Polypeptides with Improved HPPD Inhibitor Herbicide Tolerance The activity of HPPD polypeptides was determined in absence or presence of HPPD inhibitors using the coupled HPPD activity assay (FIG. 1).

For the determination of the residual activity, the apparent kinetic constant ($k_{app}$) of the determined substrate conversion was measured as kinetic changes in absorbance at 320 nm in a coupled assay, in that homogentisate (HGA) formed by HPPD from HPP is directly converted into the well absorbing molecule maleylacetoacetate (MAA) by a second enzyme homogentisate dioxygenase (HGD), applied in excess uniformly in all assays (see FIG. 1). The measurements were performed in 384 micro titer plates (Greiner Bio-One GmbH, Frickenhausen, Germany) by plate readers (Tecan infinite M1000 or M1000PRO, Tecan, Männedorf, Switzerland). The $k_{cat}/k_M$ ratio of an enzymatic activity is proportional to the apparent kinetic constant $k_{app}$ and is proportional to $k_{cat}/k_M$*[E] ([E]=enzyme concentration). A competitive inhibitor exhibits an apparent increase in $k_M$ and thereby a reciprocal decrease in $k_{app}$ at non-saturating substrate concentrations. As both $k_{app}$ measurements in the presence and absence of inhibitor were performed by use of the identical enzyme sample, crude or purified, and thereby at the same enzyme concentration, the enzyme concentration eliminates from the calculation of residual activity and the ratio of both $k_{app}$ directly indicates the change of $k_M$ due to the inhibition. Noteworthy, this concept applies to enzyme/inhibitor pairs interacting in a "competitive inhibition" manner, probably correct for almost all polypeptide variants and inhibitors described herein, but for sure not with respect to the wild-type polypeptide, which is inhibited irreversibly (for comparison see WO2014/043435, FIGS. 2 and 3). Consequently, residual activities of the wild-type HPPD polypeptide referring to "competitive inhibition" and ki values can't be correctly calculated, nevertheless, for the purpose of illustration unfounded values are given in Table 3 for the wild-type HPPD polypeptide, which are calculated by initial changes in signal before the irreversible inhibition took place.

The assay solution used for determination of residual activities in raw HPPD polypeptide samples was composed by 200 mM sodium phosphate (Merck, Darmstadt, Germany, pH 7.0), 5 mM $MgCl_2$ (Merck, Darmstadt, Germany), 20 mM ascorbate (Sigma-Aldrich, St. Louis, USA), 1 mM DTT (Sigma-Aldrich, St. Louis, USA), 0.1% Pluronic F-68 (Sigma-Aldrich, St. Louis, USA), 40 μM $FeSO_4$ (Sigma-Aldrich, St. Louis, USA), about 8 mg/ml purified HGD and low or high concentrations of substrate HPP (100 or 400 μM) from a 1 M stock solution in DMSO (Sigma-Aldrich, St. Louis, USA) and equilibrated for 20 min on ice. For every HPPD polypeptide sample two assays were performed in quadruplets, whereby 5 μl of HPPD polypeptide sample were mixed firstly with 5 μl buffer (1× BugBuster®; (Merck, Darmstadt, Germany); in 140 mM Tris, pH7.8, with 1:25000 diluted BNase®; Qiagen, Hilden, Germany)) or 5 μl inhibitor diluted in the same buffer from a 0.1 M stock solution in DMSO (30, 100 or 120 μM resulting in 15, 50 and 60 μM in the HPPD polypeptide/inhibitor sample) in the reference and inhibition assay, respectively, and subsequently with 10 μl assay solution. The change in absorbance at 320 nm was followed in 1 min intervals for 30 min. The $k_{app}$ values were calculated as signal slope over time in the early phase of the kinetic reaction, usually for the first 5-10 minutes of the measurements (compare FIG. 3). Additionally and according to the calculated residual activity, the total conversion, i.e. the absolute change in signal, in the 30 min timeframe was monitored as measure of turnover, and a residual turnover was calculated by dividing the change in signal in the presence of inhibitor by the change in signal in the reference sample without inhibitor.

The assay solutions used for determination of ki values were composed in the same way containing six different concentrations of HPP substrate (0-1350 μM) for each of the four inhibitor concentrations tested. The inhibitors were diluted in 140 mM Tris, 0.05% Pluronic F-68 (Sigma-Aldrich, St. Louis, USA) and applied in concentrations adopted for the respective HPPD polypeptide/inhibitor pairs to generate dynamic data (FIG. 4*a-d*); generally, their concentrations in the HPPD polypeptide/inhibitor sample were in the range from 0 to 0.0012 M.

Example 4: Improved Herbicide Tolerance Mediated by Residue Exchanges in HPPD Polypeptides When the tolerance of mutant HPPD polypeptides was determined against different available chemical classes of HPPD inhibitor herbicides (triketones, isoxazoles, N-(1,3,4-oxadiazol-2-yl)benzamides, or N-(tetrazol-5-yl)-arylcarboxamides), it became evident that some of the new embodiments in this invention are not only significantly improved compared to reference wild-type HPPD (SEQ ID NO:1), but also unexpectedly better than the prior art mutant HPPD polypeptides (like, for example, those being disclosed in WO2014/043435) with SEQ ID NO:2 in this invention as an example.

As outlined in Table 3, prior art mutant HPPD polypeptides (WO2014/043435) corresponding to SEQ ID NO:2 in this invention contains residue exchanges at position 335, 336, 339 and 340. Based on mutant HPPD polypeptide comprising 335 (E=>P), 336 (G=>D/H), 337 (N=>S), the introduction of further residue exchanges at position 264, 268, 270, 330, 340 and/or 345 generated mutant HPPD polypeptides showing strongly improved tolerance (Table 3), concerning multiple applied HPPD inhibitors belonging to various chemical classes.

Accordingly, we generated and evaluated new mutant HPPD polypeptides by combinatorial residue exchanges at position 335 (glutamic acid=>proline), 336 (glycine=>aspartic acid/histidine), 337 (asparagine=>serine) and, optionally, further comprising exchanges at position 204, 213, 264, 268, 270, 310, 315, 330, 331, 338, 339, 340, 344 and/or 345 (Table 3, 4 and 5), that exhibit improved residual activities, higher residual turnover, higher ki values and thereby significantly higher herbicide tolerance. Depending on the HPPD inhibitor herbicide tested, the level of improvement might differ concerning the HPPD polypeptides employed in such assay, with a level of 1.5 up to 110 fold, compared to SEQ ID NO: 2 (Table 4).

Analysis of the time-course of inhibition against the different HPPD inhibitor herbicide chemical classes revealed, that the HPPD inhibitor herbicides appear to be reversible inhibitors against the new mutant HPPD polypeptides, in contrast to the slow and tight binding inhibitor characteristic of the wild-type HPPD polypeptide corresponding to SEQ ID NO:1 (see FIGS. 2 and 3). These behaviors provide a better and versatile potential for tolerances in crop plants to various HPPD inhibitor herbicides.

For high residual activity in the presence of HPPD inhibitor herbicides, the disclosed positions and residue changes are highlighted in Table 1 relative to the amino acid position in the HPPD polypeptide corresponding to SEQ ID NO:1 in this invention are shown to be important.

TABLE 3

Tolerance of mutant HPPD polypeptides against different HPPD inhibitor herbicides belonging to diverse chemical classes.

Table 3a) Residual activity and turnover in the presence of Cmpd. 1 according to Example 3 at high substrate concentration and 15 μM inhibitor.

| SEQ ID | Amino acid position relative to HPPD polypeptide SEQ ID NO: 1 | | | | | | | | | | Residual | Residual |
|---|---|---|---|---|---|---|---|---|---|---|---|---|
| NO | 264 | 268 | 270 | 330 | 335 | 336 | 337 | 339 | 340 | 345 | activity | turnover |
| 1 | M | P | T | D | E | G | N | K | A | I | 6% | 6% |
| 2 | | | | | P | W | | A | Q | | 39% | 50% |
| 3 | | | | | P | | | | | | 9% | 9% |
| 4 | | | | | | | S | | | | 13% | 12% |
| 5 | | | | | P | | S | | | | 20% | 24% |
| 7 | | | | | P | D | S | | | | 27% | 38% |
| 8 | | | | | P | D | S | | V | | 21% | 44% |
| 9 | | | | | P | D | S | | | V | 36% | 51% |
| 10 | | | | | P | D | S | | V | V | 41% | 66% |
| 11 | | | | H | P | D | S | | | | 24% | 30% |
| 12 | | | | H | P | D | S | | V | | 43% | 55% |
| 13 | | | | H | P | D | S | | | V | 35% | 40% |
| 14 | | | | H | P | D | S | | V | V | 44% | 60% |
| 15 | | S | S | | P | D | S | | V | V | 46% | 74% |
| 16 | | S | S | | P | D | S | | V | K | 45% | 69% |
| 17 | | G | E | | P | D | S | | V | V | 43% | 68% |
| 18 | R | | | H | P | D | S | | V | | 67% | 79% |
| 19 | R | G | E | H | P | D | S | | V | V | 68% | 79% |
| 20 | | | | | P | H | | | | | 14% | 16% |
| 21 | | | | | P | H | S | | | | 18% | 30% |
| 22 | | | | | P | H | S | | V | | 26% | 53% |
| 23 | | | | | P | H | S | | | V | 26% | 36% |
| 24 | | | | | P | H | S | | V | V | 28% | 57% |
| 25 | | | | H | P | H | S | | | | 33% | 37% |
| 26 | | | | H | P | H | S | | V | | 55% | 65% |
| 27 | | | | H | P | H | S | | | V | 36% | 42% |
| 28 | | | | H | P | H | S | | V | V | 45% | 57% |
| 29 | | S | S | | P | H | S | | V | V | 33% | 59% |
| 30 | | S | S | | P | H | S | | V | K | 39% | 65% |
| 31 | | G | E | | P | H | S | | V | V | 40% | 67% |

TABLE 3-continued

Tolerance of mutant HPPD polypeptides against different HPPD inhibitor herbicides belonging to diverse chemical classes.

Table 3b) Residual activity and turnover in the presence of Cmpd. 2 according to Example 3 at high substrate concentration and 15 μM inhibitor.

| SEQ ID | Amino acid position relative to HPPD polypeptide SEQ ID NO: 1 | | | | | | | | | | Residual | Residual |
|---|---|---|---|---|---|---|---|---|---|---|---|---|
| NO | 264 | 268 | 270 | 330 | 335 | 336 | 337 | 339 | 340 | 345 | activity | turnover |
| 1 | M | P | T | D | E | G | N | K | A | I | 8% | 8% |
| 2 | | | | | P | W | | A | Q | | 51% | 72% |
| 3 | | | | | P | | | | | | 16% | 22% |
| 4 | | | | | | | S | | | | 18% | 17% |
| 5 | | | | | P | | S | | | | 36% | 53% |
| 7 | | | | | P | D | S | | | | 75% | 83% |
| 8 | | | | | P | D | S | | V | | 67% | 74% |
| 9 | | | | | P | D | S | | | V | 79% | 89% |
| 10 | | | | | P | D | S | | V | V | 89% | n.i. |
| 11 | | | | H | P | D | S | | | | 59% | 67% |
| 12 | | | | H | P | D | S | | V | | 93% | n.i. |
| 13 | | | | H | P | D | S | | | V | 82% | 88% |
| 14 | | | | H | P | D | S | | V | V | 82% | 92% |
| 15 | | S | S | | P | D | S | | V | V | 90% | n.i. |
| 16 | | S | S | | P | D | S | | V | K | 94% | 94% |
| 17 | | G | E | | P | D | S | | V | V | 90% | 90% |
| 18 | R | | | H | P | D | S | | V | | n.i. | n.i. |
| 19 | R | G | E | H | P | D | S | | V | V | 92% | 93% |
| 20 | | | | | P | H | | | | | 31% | 50% |
| 21 | | | | | P | H | S | | | | 73% | 84% |
| 22 | | | | | P | H | S | | V | | 90% | n.i. |
| 23 | | | | | P | H | S | | | V | 76% | 83% |
| 24 | | | | | P | H | S | | V | V | 90% | n.i. |
| 25 | | | | H | P | H | S | | | | 82% | 83% |
| 26 | | | | H | P | H | S | | V | | 92% | 95% |
| 27 | | | | H | P | H | S | | | V | 80% | 86% |
| 28 | | | | H | P | H | S | | V | V | 83% | 93% |
| 29 | | S | S | | P | H | S | | V | V | 85% | n.i. |
| 30 | | S | S | | P | H | S | | V | K | 95% | n.i. |
| 31 | | G | E | | P | H | S | | V | V | 95% | n.i. |

TABLE 3-continued

Tolerance of mutant HPPD polypeptides against different HPPD inhibitor herbicides belonging to diverse chemical classes.

Table 3c) Residual activity and turnover in the presence of mesotrione (MST) according to Example 3 at high substrate concentration and 60 μM inhibitor.

| SEQ ID | Amino acid position relative to HPPD polypeptide SEQ ID NO: 1 | | | | | | | | | | Residual | Residual |
|---|---|---|---|---|---|---|---|---|---|---|---|---|
| NO | 264 | 268 | 270 | 330 | 335 | 336 | 337 | 339 | 340 | 345 | activity | turnover |
| 1 | M | P | T | D | E | G | N | K | A | I | 6% | 8% |
| 2 | | | | | P | W | | A | Q | | 71% | 85% |
| 3 | | | | | P | | | | | | 13% | 17% |
| 4 | | | | | | | S | | | | 16% | 15% |
| 5 | | | | | P | | S | | | | 46% | 71% |
| 7 | | | | | P | D | S | | | | 70% | 85% |
| 8 | | | | | P | D | S | | V | | 70% | 85% |
| 9 | | | | | P | D | S | | | V | 71% | 86% |
| 10 | | | | | P | D | S | | V | V | 82% | n.i. |
| 11 | | | | H | P | D | S | | | | 64% | 85% |
| 12 | | | | H | P | D | S | | V | | 80% | 94% |
| 13 | | | | H | P | D | S | | | V | 72% | 88% |
| 14 | | | | H | P | D | S | | V | V | 70% | 89% |
| 15 | | S | S | | P | D | S | | V | V | 83% | 94% |
| 16 | | S | S | | P | D | S | | V | K | 88% | 92% |
| 17 | | G | E | | P | D | S | | V | V | 85% | 90% |
| 19 | R | G | E | H | P | D | S | | V | V | 51% | 78% |
| 20 | | | | | P | H | | | | | 25% | 40% |
| 21 | | | | | P | H | S | | | | 62% | 89% |
| 22 | | | | | P | H | S | | V | | 77% | 99% |
| 23 | | | | | P | H | S | | | V | 63% | 79% |
| 24 | | | | | P | H | S | | V | V | 51% | 68% |
| 25 | | | | H | P | H | S | | | | 70% | 87% |
| 26 | | | | H | P | H | S | | V | | 81% | 92% |
| 27 | | | | H | P | H | S | | | V | 64% | 82% |
| 28 | | | | H | P | H | S | | V | V | 66% | 84% |
| 29 | | S | S | | P | H | S | | V | V | 79% | 95% |
| 30 | | S | S | | P | H | S | | V | K | 87% | n.i. |
| 31 | | G | E | | P | H | S | | V | V | 83% | n.i. |

TABLE 3-continued

Tolerance of mutant HPPD polypeptides against different HPPD inhibitor herbicides belonging to diverse chemical classes.

Table 3d) Residual activity Hand turnover in the presence of diketonitrile (DKN) according to Example 3 at high substrate concentration and 60 μM inhibitor.

| SEQ ID NO | Amino acid position relative to HPPD polypeptide SEQ ID NO: 1 | | | | | | | | | | Residual activity | Residual turnover |
|---|---|---|---|---|---|---|---|---|---|---|---|---|
| | 264 | 268 | 270 | 330 | 335 | 336 | 337 | 339 | 340 | 345 | | |
| 1 | M | P | T | D | E | G | N | K | A | I | 7% | 8% |
| 2 | | | | | P | W | | A | Q | | 86% | 93% |
| 3 | | | | | P | | | | | | 17% | 17% |
| 4 | | | | | | | S | | | | 17% | 14% |
| 5 | | | | | P | | S | | | | 41% | 47% |
| 7 | | | | | P | D | S | | | | 79% | 92% |
| 8 | | | | | P | D | S | | V | | 91% | 95% |
| 9 | | | | | P | D | S | | | V | 90% | 92% |
| 10 | | | | | P | D | S | | V | V | n.i. | n.i. |
| 11 | | | | H | P | D | S | | | | 81% | 95% |
| 12 | | | | H | P | D | S | | V | | n.i. | n.i. |
| 13 | | | | H | P | D | S | | | V | n.i | n.i. |
| 14 | | | | H | P | D | S | | V | V | 91% | n.i |
| 15 | | S | S | | P | D | S | | V | V | n.i. | n.i. |
| 16 | | S | S | | P | D | S | | V | K | n.i. | n.i. |
| 17 | | G | E | | P | D | S | | V | V | n.i. | 95% |
| 18 | R | | | H | P | D | S | | V | | n.i. | n.i. |
| 19 | R | G | E | H | P | D | S | | V | V | n.i. | n.i |
| 20 | | | | | P | H | | | | | 37% | 40% |
| 21 | | | | | P | H | S | | | | 81% | n.i |
| 22 | | | | | P | H | S | | V | | n.i | n.i. |
| 23 | | | | | P | H | S | | | V | 83% | 87% |
| 24 | | | | | P | H | S | | V | V | 93% | n.i. |
| 25 | | | | H | P | H | S | | | | n.i. | n.i. |
| 26 | | | | H | P | H | S | | V | | n.i | n.i. |
| 27 | | | | H | P | H | S | | | V | 92% | n.i. |
| 28 | | | | H | P | H | S | | V | V | 90% | 95% |
| 29 | | S | S | | P | H | S | | V | V | 94% | n.i. |
| 30 | | S | S | | P | H | S | | V | K | n.i. | n.i. |
| 31 | | G | E | | P | H | S | | V | V | n.i. | n.i. |

Residual activities and residual turnover were determined according to Example 3 by measuring $k_{app}$ and total change in signal, respectively, in the presence and absence of (a) Cmpd. 1 (2-chloro-3-(methylsulfanyl)-N-(1-methyl-1H-tetrazol-5-yl)-4-(trifluoromethyl)benzamide), (b) Cmpd. 2 (2-methyl-N-(5-methyl-1,3,4-oxadiazol-2-yl)-3-(methylsulfonyl)-4-(trifluoromethyl)benzamide), (c) mesotrione (MST), and (d) diketonitrile (DKN). For each mutant HPPD polypeptide, the $k_{app}$ and total change in signal without HPPD inhibitor herbicides served for normalization of the $k_{app}$ and total change in signal in the presence of the herbicide. The summarized resulting "%-values" in the respective tables 3a), 3b), 3c), and 3d) are means of two independent experiments with an average standard deviation of 5%. The reaction was performed at high substrate concentrations with Cmpd. 1 and Cmpd. 2 at a concentration of 15 μM and the other two herbicides (DKN, MST) at a concentration of 60 μM. For clarity, empty cells at the respective amino acid position in SEQ ID NO:2 to SEQ ID NO:108 are defined as identical to the amino acids corresponding to SEQ ID NO:1, highlighting only the exchanges in the HPPD polypeptide variant. The abbreviation "n.i." means that no inhibition was observed under the given conditions, i.e. the $k_{app}$ or the total change in signal in the presence of inhibitor is not decreased compared to the corresponding value in the absence of inhibitors.

The mutant HPPD polypeptides corresponding to SEQ ID NO:10 and SEQ ID NO:24 with amino acid exchanges at positions 335, 336, 337, 340, and 345 relative to HPPD polypeptide according to SEQ ID NO:1, exhibit in the presence of various HPPD inhibitors tested a significant improvement regarding residual activities and residual turnovers (Table 3a-d). The depicted herbicide tolerance of SEQ ID NO:10 shows not only the improvement vs. the wild-type HPPD polypeptide (SEQ ID NO:1), but also vs. the prior art (WO2014/043435) mutant HPPD polypeptide corresponding to SEQ ID NO:2 in this invention across all four depicted different herbicide classes.

Further improvements in HPPD inhibitor tolerance are apparent in variants with residue exchanges at the disclosed amino acid positions 268 and 270.

Starting from SEQ ID NO: 24, SEQ ID NO:31 differ only at the stated positions 268 and 270. These changes increase significantly the residual turnover in the presence of HPPD inhibitor Cmpd. 1 and MST (Table 3a and 3c), and keeps the already achieved high residual turnover in the presence of Cmpd. 2 (Table 3b) and DKN (Table 3d). These results are also seen by significantly improved ki values of SEQ ID NO: 31 (Table 4) compared to the HPPD polypeptide (SEQ ID NO:1), and prior art mutant HPPD polypeptide (WO2014/043435) corresponding to SEQ ID NO:2 in this invention.

Starting from mutant HPPD polypeptide corresponding to SEQ ID NO:8, further change of amino acid 330 (see SEQ ID NO: 12) shows further improved HPPD inhibitor tolerance (see Table 3)

Starting from mutant HPPD polypeptide corresponding to SEQ ID NO:12, further change of amino acid position 264 (see SEQ ID NO: 18) show further significant improved HPPD inhibitor tolerance towards Cmpd. 1 and Cmpd. 2 (see Tables 3a, 3b).

Introducing all above mentioned exchanges in the four positions 264, 268, 270, 330 on top of mutant HPPD polypeptide corresponding to SEQ ID NO:10 leading to SEQ ID NO:19, the strongest tolerance of all depicted polypeptides in Table 3a with residual activity and turnover of 68% and 79% towards Cmpd. 1 was detected, demonstrating the importance of the combinatorial residue exchanges at the disclosed amino acid positions. Also the mutant HPPD polypeptide corresponding to SEQ ID NO:19 having improved ki values for Cmpd. 1 and Cmpd. 2 (Table 4) compared to SEQ ID NO:2.

TABLE 4

Evaluation of tolerance of mutated HPPD polypeptides against different HPPD inhibitor herbicides belonging to various chemical classes by the determiniation of the ki values

| SEQ ID | Amino acid position relative to HPPD polypeptide SEQ ID NO: 1 | | | | | | | | | | | | | | | Cmpd. 1 ki | Cmpd. 2 ki | Cmpd. 3 ki |
|---|---|---|---|---|---|---|---|---|---|---|---|---|---|---|---|---|---|---|
| NO | 213 | 264 | 268 | 270 | 315 | 330 | 331 | 335 | 336 | 337 | 338 | 339 | 340 | 344 | 345 | [μM] | [μM] | [μM] |
| 1 | R | M | P | T | T | D | D | E | G | N | F | K | A | S | I | | | |
| 2 | | | | | | | | P | W | | | A | Q | | | 1 | 3 | 22 |
| 8 | | | | | | | | P | D | S | | | V | | | 4.8 | 90 | 72 |
| 17 | | | G | E | | | | P | D | S | | | V | | V | 19 | 190 | 130 |
| 31 | | | G | E | | | | P | H | S | | | V | | V | 25 | 120 | 75 |
| 32 | | | R | E | | | | P | H | S | | | V | | V | 41 | 110 | 120 |
| 33 | | | G | E | | | | P | D | S | | | R | | V | 17 | 100 | 85 |
| 34 | | | G | E | | H | | P | D | S | | | R | | K | 21 | 89 | 120 |
| 35 | | | G | E | | | | P | D | S | | | R | | K | 88 | 160 | 150 |
| 16 | | | S | S | | | | P | D | S | | | V | | K | 9.5 | 180 | 150 |
| 18 | | R | | | | H | | P | D | S | | | V | | | 19 | 190 | 34 |
| 19 | | R | G | E | | H | | P | D | S | | | V | | V | 33 | 180 | 35 |
| 36 | | R | G | E | | H | | P | D | S | | | V | | M | 39 | 120 | 39 |
| 37 | | | G | R | | H | | P | D | S | | | V | | K | 12 | 76 | 81 |
| 38 | | | G | E | | V | | P | D | S | | | V | | V | 74 | 170 | 490 |
| 45 | | | G | E | R | | | P | D | S | | | V | | V | 9.7 | 110 | 120 |
| 48 | | | G | E | | | H | P | D | S | | | V | | V | 39 | 160 | 210 |

TABLE 4-continued

Evaluation of tolerance of mutated HPPD polypeptides against different HPPD inhibitor herbicides belonging to various chemical classes by the determiniation of the ki values

| SEQ ID NO | Amino acid position relative to HPPD polypeptide SEQ ID NO: 1 | | | | | | | | | | | | | | | Cmpd. 1 ki [μM] | Cmpd. 2 ki [μM] | Cmpd. 3 ki [μM] |
|---|---|---|---|---|---|---|---|---|---|---|---|---|---|---|---|---|---|---|
| | 213 | 264 | 268 | 270 | 315 | 330 | 331 | 335 | 336 | 337 | 338 | 339 | 340 | 344 | 345 | | | |
| 50 | | | G | E | | | P | P | D | S | | | V | | V | 47 | 130 | 140 |
| 60 | | R | G | E | | H | | P | D | S | | | V | Q | V | 24 | 130 | 32 |
| 96 | K | | G | E | | | | P | H | S | | | V | | V | 19 | 98 | 93 |
| 97 | | | G | R | | H | S | P | D | S | | | V | | K | 17 | 86 | 130 |
| 98 | | | G | E | | H | S | P | D | S | | | R | | K | 33 | 40 | 150 |
| 99 | | | G | E | | | | P | D | S | V | | R | | V | 100 | 160 | 150 |
| 100 | | L | G | E | | H | | P | D | S | | | V | Q | M | 100 | 120 | 120 |
| 101 | | L | G | E | R | | | P | D | S | | | V | Q | M | 45 | 96 | 89 |
| 102 | | L | G | E | R | | | P | H | S | | | V | Q | M | 40 | 230 | 290 |
| 103 | K | L | G | E | R | | | P | H | S | | | V | Q | M | 24 | 260 | 280 |
| 104 | K | L | G | E | | | | P | H | S | | | V | Q | M | 43 | 370 | 270 |
| 105 | K | L | G | E | | | | P | H | S | | | R | Q | M | 140 | 270 | 100 |
| 106 | | L | G | E | | H | P | P | D | S | | | V | Q | M | 95 | 240 | 120 |
| 107 | K | | G | E | | | | P | H | S | V | | R | | V | 110 | 190 | 100 |
| 108 | | | G | E | M | H | | P | D | S | | | V | | M | 33 | 150 | 98 |

For clarity, empty cells at the respective amino acid position in SEQ ID NO:2 to SEQ ID NO:108 are defined as identical to the amino acids corresponding to SEQ ID NO:1, highlighting only the exchanges in the mutant HPPD polypeptides. The mutant HPPD polypeptides represented here are examples by a way of illustration, not by a way of limitation. Data were obtained by measuring the initial reaction rates with increasing concentrations of Cmpd. 1 (2-chloro-3-(methylsulfanyl)-N-(1-methyl-1H-tetrazol-5-yl)-4-(trifluoromethyl)benzamide), Cmpd. 2 (2-methyl-N-(5-methyl-1,3,4-oxadiazol-2-yl)-3-(methylsulfonyl)-4-(trifluoromethyl)benzamide), and mesotrione (MST) according to Example 3. Generally, six different concentrations of HPP substrate (0-1350 μM) and four different concentrations of the respective inhibitor were applied (see FIG. 4). The inhibitor concentrations were adopted for the respective HPPD polypeptide/inhibitor pairs to generate dynamic data, i.e. variants with lower tolerance were analyzed in a range of lower inhibitor concentrations, and concentrations of up to 1200 μM were used for variants with maximized tolerance. GraphPad Prism (version 6.00 for Windows, GraphPad Software, La Jolla Calif. USA) were used for data analysis and fitting of kinetic constants applying constraints according to a competitive inhibition mode. Where obvious outliers occurred, or activities obtained at very high substrate concentrations didn't obey the mathematics underlying the competitive inhibition mode, respective values were excluded from the fit.

Some results of systematical variants generated on the basis of the two already significantly improved mutated HPPD polypeptides SEQ ID NO:17 and SEQ ID NO:19 are outlined in Table 5.

SEQ ID NO:17 and SEQ ID NO:19 differ at two amino acid positions, and SEQ ID NO:17 shows a ~20-fold, SEQ ID NO:19 a ~30-fold increased ki towards Cmpd. 1 compared to mutant HPPD polypeptide corresponding to SEQ ID NO:2 (see Table 4).

The mutant HPPD polypeptide corresponding to SEQ ID NO:17 has residue exchanges at positions 268, 270, 335, 336, 337, 340, and 345 and exhibits 29% residual activity and the substrate turnover is reduced by only 46% in the presence of 50 μM Cmpd. 1. A reversion of residues at position 268, 270, 340, 345 to the respective wild-type residue (according to SEQ ID NO:1) is attended by a drop in tolerance to 19%, 24%, 17%, and 20% residual activity, respectively (Table 5; SEQ ID NO:71, SEQ ID NO:63, SEQ ID NO:81, SEQ ID NO:88, respectively) emphasizing the advantageous properties of these positions and mutations. Accordingly, a reversion of the residue Valine at position 345 in SEQ ID:19 to the respective wild-type residue Isoleucine is attended by a drop in residual activity from 67% to 57% (Table 5; SEQ ID NO:93).

On the other hand, the introduction of further single residue exchanges into SEQ ID:17 at position 204, 213, 264, 310, 315, 330, 331, 338, 339 or 344 resulted for every position in at least one variant with a further significantly increased residual activity of greater than 38%, e.g. A204M (SEQ ID NO:40), R213L (SEQ ID NO:44), M264K (SEQ ID NO:67), Q310K (SEQ ID NO:65), T315R (SEQ ID NO:45), D330V (SEQ ID NO:38), D331I (SEQ ID NO:49), F338V (SEQ ID NO:53), K339E (SEQ ID NO:55) and S344P (SEQ ID NO:58).

In summary, specific additional residue exchanges beyond mutations 335 (glutamic acid (E)=>proline (P)), 336 (glycine (G)=>aspartic acid (D)/histidine (H)), and 337 (asparagine (N)=>serine (S)) in the HPPD polypeptides provide improvements in the herbicide tolerance and demonstrates the additional importance of the disclosed positions 204, 213, 264, 268, 270, 310, 315, 330, 331, 338, 339, 340, 344, 345 conferring tolerance improvements to HPPD inhibitor herbicides (Table 5). Finally, the combination of these disclosed positions lead to ki improvements across the different HPPD inhibitor classes, as demonstrated in Table 4 (e.g. SEQ ID NO:99, 100, 105, and 107) against Cmpd. 1 with more than 100-fold, against Cmpd. 2 with up to 90-fold, and at the same time up to ~7-fold improvements against mesotrione (MST) compared to wild-type HPPD polypeptide (SEQ ID NO:1) and prior art mutant HPPD polypeptide (WO2014/043435) corresponding to SEQ ID NO:2 in this invention.

TABLE 5

Effect of single residue exhchanges in SEQ ID No: 17 and SEQ ID NO: 19 analysed according to Example 3 at low substrate concentration and 50 μM inhibitor Cmpd. 1.

| SEQ ID NO | Amino acid position relative to HPPD polypeptide SEQ ID NO: 1 | | | | | | | | | | | | | | | | | Residual activity | Residual turnover |
|---|---|---|---|---|---|---|---|---|---|---|---|---|---|---|---|---|---|---|---|
| | 204 | 213 | 264 | 268 | 270 | 310 | 315 | 330 | 331 | 335 | 336 | 337 | 338 | 339 | 340 | 344 | 345 | | |
| 17 | | | | G | E | | | | | P | D | S | | | V | | V | 29% | 54% |
| 31 | | | | G | E | | | | | P | H | S | | | V | | V | 50% | 81% |
| 39 | L | | | G | E | | | | | P | D | S | | | V | | V | 34% | 61% |
| 40 | M | | | G | E | | | | | P | D | S | | | V | | V | 65% | 77% |
| 41 | S | | | G | E | | | | | P | D | S | | | V | | V | 54% | 77% |
| 42 | T | | | G | E | | | | | P | D | S | | | V | | V | 59% | 87% |
| 43 | | K | | G | E | | | | | P | D | S | | | V | | V | 28% | 61% |
| 44 | | L | | G | E | | | | | P | D | S | | | V | | V | 58% | 78% |
| 67 | | | K | G | E | | | | | P | D | S | | | V | | V | 73% | 96% |
| 68 | | | L | G | E | | | | | P | D | S | | | V | | V | 42% | 70% |
| 69 | | | Q | G | E | | | | | P | D | S | | | V | | V | 60% | 90% |
| 70 | | | R | G | E | | | | | P | D | S | | | V | | V | 55% | 74% |
| 71 | | | | | E | | | | | P | D | S | | | V | | V | 19% | 41% |
| 72 | | | | R | E | | | | | P | D | S | | | V | | V | 25% | 55% |
| 73 | | | | S | E | | | | | P | D | S | | | V | | V | 29% | 58% |
| 63 | | | | G | | | | | | P | D | S | | | V | | V | 24% | 54% |
| 74 | | | | G | L | | | | | P | D | S | | | V | | V | 26% | 59% |
| 75 | | | | G | P | | | | | P | D | S | | | V | | V | 36% | 67% |
| 76 | | | | G | R | | | | | P | D | S | | | V | | V | 19% | 50% |
| 77 | | | | G | S | | | | | P | D | S | | | V | | V | 19% | 44% |
| 64 | | | | G | E | H | | | | P | D | S | | | V | | V | 60% | 64% |
| 65 | | | | G | E | K | | | | P | D | S | | | V | | V | 90% | 96% |
| 66 | | | | G | E | S | | | | P | D | S | | | V | | V | 87% | 91% |
| 45 | | | | G | E | | R | | | P | D | S | | | V | | V | 39% | 68% |
| 46 | | | | G | E | | M | | | P | D | S | | | V | | V | 32% | 59% |
| 47 | | | | G | E | | H | | | P | D | S | | | V | | V | 31% | 59% |
| 78 | | | | G | E | | | A | | P | D | S | | | V | | V | 33% | 63% |
| 79 | | | | G | E | | | F | | P | D | S | | | V | | V | 39% | 66% |
| 80 | | | | G | E | | | G | | P | D | S | | | V | | V | 49% | 74% |
| 38 | | | | G | E | | | V | | P | D | S | | | V | | V | 78% | 94% |

TABLE 5-continued

Effect of single residue exhchanges in SEQ ID No: 17 and SEQ ID NO: 19 analysed according to Example 3 at low substrate concentration and 50 µM inhibitor Cmpd. 1.

| SEQ ID | Amino acid position relative to HPPD polypeptide SEQ ID NO: 1 | | | | | | | | | | | | | | | | | Residual acti- | Residual turn- |
|---|---|---|---|---|---|---|---|---|---|---|---|---|---|---|---|---|---|---|---|
| NO | 204 | 213 | 264 | 268 | 270 | 310 | 315 | 330 | 331 | 335 | 336 | 337 | 338 | 339 | 340 | 344 | 345 | vity | over |
| 48 | | | | G | E | | | H | | P | D | S | | | V | | V | 47% | 74% |
| 49 | | | | G | E | | | I | | P | D | S | | | V | | V | 58% | 78% |
| 50 | | | | G | E | | | P | | P | D | S | | | V | | V | 46% | 80% |
| 51 | | | | G | E | | | L | | P | D | S | | | V | | V | 27% | 56% |
| 52 | | | | G | E | | | S | | P | D | S | | | V | | V | 31% | 57% |
| 53 | | | | G | E | | | | | P | D | S | V | | V | | V | 50% | 63% |
| 54 | | | | G | E | | | | | P | D | S | | A | V | | V | 33% | 55% |
| 55 | | | | G | E | | | | | P | D | S | | E | V | | V | 46% | 81% |
| 56 | | | | G | E | | | | | P | D | S | | R | V | | V | 27% | 59% |
| 57 | | | | G | E | | | | | P | D | S | | T | V | | V | 33% | 68% |
| 81 | | | | G | E | | | | | P | D | S | | | | | V | 17% | 51% |
| 82 | | | | G | E | | | | | P | D | S | | | E | | V | 37% | 74% |
| 83 | | | | G | E | | | | | P | D | S | | | G | | V | 53% | 87% |
| 84 | | | | G | E | | | | | P | D | S | | | L | | V | 17% | 43% |
| 85 | | | | G | E | | | | | P | D | S | | | M | | V | 17% | 25% |
| 86 | | | | G | E | | | | | P | D | S | | | Q | | V | 23% | 45% |
| 33 | | | | G | E | | | | | P | D | S | | | R | | V | 40% | 65% |
| 58 | | | | G | E | | | | | P | D | S | | | V | P | V | 49% | 59% |
| 59 | | | | G | E | | | | | P | D | S | | | V | R | V | 19% | 46% |
| 87 | | | | G | E | | | | | P | D | S | | | V | | A | 17% | 53% |
| 88 | | | | G | E | | | | | P | D | S | | | V | | | 20% | 44% |
| 89 | | | | G | E | | | | | P | D | S | | | V | | K | 23% | 43% |
| 90 | | | | G | E | | | | | P | D | S | | | V | | M | 16% | 43% |
| 91 | | | | G | E | | | | | P | D | S | | | V | | R | 25% | 52% |
| 19 | | | R | G | E | | | H | | P | D | S | | | V | | V | 67% | 88% |
| 60 | | | R | G | E | | | H | | P | D | S | | | V | Q | V | 64% | 84% |
| 61 | | | R | G | E | | | H | | P | D | S | | | V | P | V | 61% | 88% |
| 62 | | | R | G | E | | | H | | P | D | S | | | V | R | V | 52% | 72% |
| 92 | | | R | G | E | | | H | | P | D | S | | | V | | A | 61% | 81% |
| 93 | | | R | G | E | | | H | | P | D | S | | | V | | | 57% | 75% |
| 94 | | | R | G | E | | | H | | P | D | S | | | V | | K | 20% | 62% |
| 36 | | | R | G | E | | | H | | P | D | S | | | V | | M | 67% | 85% |
| 95 | | | R | G | E | | | H | | P | D | S | | | V | | R | 40% | 81 |

For clarity, empty cells at the respective amino acid position in SEQ ID NO:2 to NO:108 are defined as identical to the amino acids corresponding to SEQ ID NO:1, highlighting only the exchanges in the mutated HPPD polypeptide. Residual activities and residual turnover were determined according to Example 3 by measuring $k_{app}$ and total change in signal respectively in the presence and absence of Cmpd. 1 (2-chloro-3-(methylsulfanyl)-N-(1-methyl-1H-tetrazol-5-yl)-4-(trifluoromethyl)benzamide) (50 μM) at low substrate concentration. For each mutant HPPD polypeptide the $k_{app}$ and total change in signal without HPPD inhibitor herbicides served for normalization of the $k_{app}$ and total change in signal in the presence of the herbicide, and resulting %-values are summarized.

Example 5: Brown Color Assay to Test for Mutant HPPD Polypeptides, Tolerant to HPPD Inhibitor Herbicides Mutant HPPD polypeptides were analyzed using a brown color assay (WO2014/043435). Bacterial cells expressing the mutant HPPD polypeptide according to the invention were assayed in 96 well format for HPPD inhibitor tolerance by spotting on solid media containing LB-agar, selection agent for the expression vector pSE420(RI)NX (WO2014/043435), 5 mM tyrosine (Sigma-Aldrich, St. Louis, USA), 42 mM succinate (Sigma-Aldrich, St. Louis, USA) and six different concentrations of the HPPD inhibitor herbicide Cmpd. 1 (0-500 μM). In the brown color assay, an overnight culture of the *E. coli* cells expressing one of the respective mutant HPPD polypeptides were diluted to an OD600 of 1 and 10 μl extract was spotted in triplicates on plates containing 0, 25, 50, 100, 250, or 500 μM of Cmpd. 1. Plates were covered with airpore tape and incubated at 30 degrees C. After 24 hours, the cells were kept in darkness at room temperature and after 7 days the brown pigment formation was scored visually. In the presence of an HPPD inhibitor herbicide, this pigment formation is inhibited and the color of the agar plate will not alter, unless an HPPD inhibitor herbicide tolerant HPPD polypeptide is expressed and active. The rating "+++" means a dark brown coloring as seen for *E. coli* cells expressing one of the respective mutant HPPD polypeptide without inhibitor in the LB agar plate. The "++" and "+" scores a medium and light brown pigmentation, respectively, and the "0" means that no brown pigmentation development was detected on the LB agar plates.

TABLE 6

Evaluation of the tolerance of mutant HPPD polypeptides towards Cmpd. 1 (0-500 μM) using the Brown Color Assay.

| | *E. coli* cells expressing an HPPD polypeptide | | | | | | |
|---|---|---|---|---|---|---|---|
| Concentration Cmpd. 1 [μM] | SEQ ID NO: 1 | SEQ ID NO: 2 | SEQ ID NO: 31 | SEQ ID NO: 32 | SEQ ID NO: 96 | SEQ ID NO: 103 | SEQ ID NO: 104 |
| 0 | +++ | +++ | +++ | +++ | +++ | +++ | +++ |
| 25 | 0 | ++ | +++ | +++ | +++ | ++ | +++ |
| 50 | 0 | ++ | +++ | +++ | ++ | ++ | +++ |
| 100 | 0 | ++ | +++ | +++ | ++ | ++ | +++ |
| 250 | 0 | + | ++ | ++ | ++ | + | ++ |
| 500 | 0 | 0 | + | + | + | 0 | ++ |

The exemplary mutant HPPD polypeptides, summarized in Table 6, showed improved tolerance towards Cmpd. 1 (2-chloro-3-(methylsulfanyl)-N-(1-methyl-1H-tetrazol-5-yl)-4-(trifluoromethyl)benzamide) compared to the HPPD polypeptide corresponding to SEQ ID NO: 1 in this invention. Already at a concentration of 25 μM Cmpd. 1, the *E. coli* cells expressing the HPPD polypeptide (corresponding to SEQ ID NO:1) do not produce any brown pigmentation and several mutant HPPD polypeptides show a dark to medium brown pigmentation.

A prior art mutant HPPD polypeptide (WO2014/043435) corresponding to SEQ ID NO: 2 in this invention developed only a slight brown pigmentation at 250 μM Cmpd. 1. and lost their brown pigmentation at 500 μM of Cmpd. 1, illustrating a complete inhibition of the expressed HPPD polypeptides in the cell. In comparison, several mutant HPPD polypeptides depicted in the Table 6 with SEQ ID NO:31, 32, 96, and especially with SEQ ID NO:104 show stronger brown coloring in the presence of 25, 50, 100, 250, and even 500 μM of Cmpd. 1.

In an additional experiment, mutant HPPD polypeptides were analyzed using the principle of a colorimetric brown color assay (as, for example, described in U.S. Pat. No. 6,768,044). Bacterial cells expressing the HPPD polypeptides according to this invention were assayed in 96 well plate format (Nunc® 96 DeepWell™ plate, Sigma-Aldrich, St. Louis, USA) for HPPD polypeptides with improved HPPD inhibitor herbicide tolerance.

*E. coli* cells were grown in liquid LB medium (Carl Roth GmbH+Co. KG, Karlsruhe, Germany) containing the selection agent for the expression vector pSE420(RI)NX (WO2014/043435) and 5 mM para-hydroxyphenylpyruvate (HPP; Sigma-Aldrich, St. Louis, USA), in the presence of absence of the HPPD inhibitor herbicide e.g. Cmpd. 1 (1000 μM). An overnight culture of *E. coli* culture expressing one of the respective HPPD polypeptides according to this invention were adjusted to an OD600 of 0.3-0.5 in a final volume of 500 μL and incubated at 30 degree Celsius. Residual brown color formation was determined by measuring the brown color formation (BCF) in the presence and absence of Cmpd. 1 (2-chloro-3-(methylsulfanyl)-N-(1-methyl-1H-tetrazol-5-yl)-4-(trifluoromethyl)benzamide). Therefore, after 96 hours the culture was centrifuged and the supernatant of the culture was used to measure the optical density of the soluble brown pigment formation at 440 nm ($OD_{440\ nm}$).

TABLE 7

Evaluation of the tolerance of exemplary mutant HPPD polypeptides towards Cmpd. 1 (1000 μM) using the brown color bioassay and detecting the residual brown color formation (BCF) after 96 hours.

| SEQ ID | Amino acid position relative to HPPD polypeptide SEQ ID NO: 1 | | | | | | | | | | | | | | | | | Control BCF | Residual BCF $OD_{440nm}$ |
|---|---|---|---|---|---|---|---|---|---|---|---|---|---|---|---|---|---|---|---|
| NO | 204 | 213 | 264 | 268 | 270 | 310 | 315 | 330 | 331 | 335 | 336 | 337 | 338 | 339 | 340 | 344 | 345 | $OD_{440nm}$ | [%] |
| 1 | A | R | M | P | T | Q | T | D | D | E | G | N | F | K | A | S | I | 2.66 | 15% |
| 2 | | | | | | | | | | P | W | | | A | Q | | | 2.68 | 18% |
| 7 | | | | | | | | | | P | D | S | | | | | | 1.83 | 40% |
| 10 | | | | | | | | | | P | D | S | | | V | | V | 1.09 | 65% |
| 14 | | | | | | | | H | | P | D | S | | | V | | V | 1.42 | 63% |
| 19 | | | R | G | E | | | H | | P | D | S | | | V | | V | 1.65 | 60% |
| 21 | | | | | | | | | | P | H | S | | | | | | 0.99 | 65% |
| 22 | | | | | | | | | | P | H | S | | | V | | | 1.67 | 58% |
| 24 | | | | | | | | | | P | H | S | | | V | | V | 1.56 | 48% |
| 29 | | | | S | S | | | | | P | H | S | | | V | | V | 2.03 | 42% |
| 30 | | | | S | S | | | | | P | H | S | | | V | | K | 1.70 | 56% |
| 39 | L | | | G | E | | | | | P | D | S | | | V | | V | 1.63 | 55% |
| 40 | M | | | G | E | | | | | P | D | S | | | V | | V | 1.89 | 58% |
| 44 | | L | | G | E | | | | | P | D | S | | | V | | V | 1.60 | 40% |
| 46 | | | | G | E | | M | | | P | D | S | | | V | | V | 2.47 | 66% |
| 52 | | | | G | E | | | | S | P | D | S | | | V | | V | 2.08 | 65% |
| 56 | | | | G | E | | | | | P | D | S | | R | V | | V | 1.98 | 68% |
| 57 | | | | G | E | | | | | P | D | S | | T | V | | V | 1.39 | 46% |
| 59 | | | | G | E | | | | | P | D | S | | | V | R | V | 1.29 | 51% |
| 67 | | | K | G | E | | | | | P | D | S | | | V | | V | 1.93 | 71% |
| 72 | | | | R | E | | | | | P | D | S | | | V | | V | 2.77 | 72% |
| 73 | | | | S | E | | | | | P | D | S | | | V | | V | 2.75 | 72% |
| 76 | | | | G | R | | | | | P | D | S | | | V | | V | 2.73 | 58% |
| 77 | | | | G | S | | | | | P | D | S | | | V | | V | 2.57 | 67% |
| 81 | | | | G | E | | | | | P | D | S | | | | | V | 2.05 | 39% |
| 83 | | | | G | E | | | | | P | D | S | | | G | | V | 1.83 | 47% |
| 86 | | | | G | E | | | | | P | D | S | | | Q | | V | 1.94 | 74% |
| 87 | | | | G | E | | | | | P | D | S | | | V | | A | 1.91 | 68% |
| 88 | | | | G | E | | | | | P | D | S | | | V | | | 2.21 | 77% |
| 89 | | | | G | E | | | | | P | D | S | | | V | | K | 2.36 | 67% |
| 92 | | | R | G | E | | | H | | P | D | S | | | V | | A | 1.38 | 59% |
| 97 | | | | G | R | | | H | S | P | D | S | | | V | | K | 1.54 | 49% |
| 99 | | | | G | E | | | | | P | D | S | V | | R | | V | 1.52 | 87% |
| 100 | | | L | G | E | | | H | | P | D | S | | | V | Q | M | 2.48 | 33% |
| 102 | | | L | R | E | | R | | | P | D | S | | | V | Q | M | 2.47 | 26% |

TABLE 7 -continued

Evaluation of the tolerance of exemplary mutant HPPD polypeptides towards Cmpd. 1 (1000 µM) using the brown color bioassay and detecting the residual brown color formation (BCF) after 96 hours.

| SEQ ID | Amino acid position relative to HPPD polypeptide SEQ ID NO: 1 | | | | | | | | | | | | | | | | | Control BCF | Residual BCF $OD_{440nm}$ |
|---|---|---|---|---|---|---|---|---|---|---|---|---|---|---|---|---|---|---|---|
| NO | 204 | 213 | 264 | 268 | 270 | 310 | 315 | 330 | 331 | 335 | 336 | 337 | 338 | 339 | 340 | 344 | 345 | $OD_{440nm}$ | [%] |
| 106 | | | L | G | E | | | H | P | P | D | S | | | V | Q | M | 1.50 | 73% |
| 107 | | K | | G | E | | | | | P | D | S | V | | R | | V | 1.38 | 84% |

The exemplary mutant HPPD polypeptides, summarized in Table 7 showed improved tolerance towards Cmpd. 1 (2-chloro-3-(methylsulfanyl)-N-(1-methyl-1H-tetrazol-5-yl)-4-(trifluoromethyl)benzamide) compared to the HPPD polypeptide corresponding to SEQ ID NO: 1 and the prior art mutant HPPD polypeptide (WO2014/043435) corresponding to SEQ ID NO: 2 in this invention. Both HPPD polypeptides corresponding to SEQ ID NO:1 and SEQ ID NO: 2 did not produce a substantial brown pigmentation in the presence of the HPPD inhibitor. Several mutant HPPD polypeptides showed a medium to dark brown pigmentation. The summarized resulting "%-values" in the respective Table 7 are means of at least two independent experiments with an average standard deviation of 5%.

Example 6: Soybean Transformation and Tolerance of the T0 Soybean Plants

Soybean transformation was achieved by using methods well known in the art, such as the one described using the *Agrobacterium tumefaciens* mediated transformation soybean half-seed explants using essentially the method described by Paz et al. (2006), Plant cell Rep. 25:206. Transformants were identified by using the HPPD inhibitor herbicide "tembotrione" as selection marker. The appearance of green shoots was observed, and documented as an indicator of tolerance to the HPPD inhibitor herbicide tembotrione. The tolerant transgenic shoots showed normal greening comparable to wild-type soybean shoots not treated with HPPD inhibitor herbicide tembotrione, whereas wild-type soybean shoots treated with the same amount of HPPD inhibitor herbicide tembotrione were entirely bleached. This indicated that the presence of the respective HPPD polypeptide enabled the tolerance to HPPD inhibitor herbicides, like tembotrione.

Tolerant green shoots were transferred to rooting media or grafted. Rooted plantlets were transferred to the greenhouse after an acclimation period. Plants containing the transgene were then sprayed with HPPD inhibitor herbicides, as for example with mesotrione at a rate of 300-600 g AI/ha, or with Cmpd. 1 (2-chloro-3-(methylsulfanyl)-N-(1-methyl-1H-tetrazol-5-yl)-4-(trifluoromethyl)benzamide) at a rate of 150 g-300 g AI/ha supplemented with ammonium sulfate and methyl ester rapeseed oil. Five to ten days after the application, the symptoms due to the application of the herbicide were evaluated and compared to the symptoms observed on wild-type plants under the same conditions.

For example, T0 soybean plants having a "plant expression cassette", which includes an HPPD inhibitor tolerant HPPD polypeptide of the present invention, were tested towards the tolerance of Cmpd. 1.

Prior greenhouse trials with the transgenic plants, soybean transformants were routinely analyzed for the expression and presence of the transgenes using the ELISA protein detection method (see detailed description under item D and H). Only plants recovering in the selection media and having a detectable HPPD transgene protein expression were used for the herbicide tolerance analysis. A DeVries Tracker Sprayer was calibrated prior to each spraying. The chemical formulation used for Cmpd. 1 was supplemented with ammonium sulfate and methylated rape seed oil. Spray tests were conducted with a concentration, which equals to 300 grams AI per hectare (300 g AI/ha). Tolerance was evaluated 5 days after spraying. Wild-type soybean plants sprayed with the same herbicide formulation were totally bleached and exhibited more than 95% leaf damage of the top two trifoliate leaves. A rating of "1" was assigned to plants having slight tolerance, i.e., the top two trifoliate leaves show significant bleaching and little sign of recovery with 50-95% leaf damage. A rating of "2" was assigned to plants showing moderate tolerance, i.e., between 10-49% of the leaf area of the top three trifoliate leaves showing significant amounts of resistance to the herbicide treatment. A rating of "3" was assigned to plants showing good tolerance, i.e. less than 10% of the leaf area from the top three trifoliate leaves showing chlorosis or only very slight bleaching. The results are summarized in Table 8.

TABLE 8

Evaluation of leaf area damage from transgenic soybean T0 events five days after the application of Cmpd. 1 at a rate of 300 g AI/ha.

| Soybean Events expressing HPPD | Herbicide Tolerance Rating | | | | Total number | Percentage events rated |
|---|---|---|---|---|---|---|
| polpypetide of | 0 | 1 | 2 | 3 | events treated | "2 & 3" |
| SEQ ID NO: 2 | 5 | 10 | 26 | 49 | 90 | 83.3% |
| SEQ ID NO: 32 | 1 | 0 | 10 | 28 | 39 | 97.4% |
| SEQ ID NO: 96 | 0 | 5 | 43 | 34 | 82 | 93.9% |
| SEQ ID NO: 31 | 4 | 1 | 21 | 30 | 56 | 91.1% |

The results in Table 8 show that a significant portion of independent soybean T0 events are tolerant to the HPPD inhibitor herbicide Cmpd. 1 (2-chloro-3-(methylsulfanyl)-N-(1-methyl-1H-tetrazol-5-yl)-4-(trifluoromethyl)benzamide) at a rate of 300 g AI/ha compared to wild-type soybean control plants also treated with the HPPD inhibitor herbicide Cmpd. 1.

More than 90% of T0 soybean events with the mutant HPPD polypeptides corresponding to SEQ ID NO: 32, SEQ ID NO: 96, and SEQ ID NO: 31 have less than 50% leaf damage and therefore also better than prior art HPPD polypeptide (WO2014/043435) T0 population with a proportion of 83% corresponding to SEQ ID NO:2 in this invention. In addition ~72% of T0 soybean events with the mutant HPPD polypeptide corresponding to SEQ ID NO: 32 show less than 10% leaf damage, which again shows an improvement compared to the T0 soybean event population (54%) overexpressing the prior art HPPD polypeptide (WO2014/043435) corresponding to SEQ ID NO:2 in this invention.

In additional greenhouse trials, 21 to 94 independent T0 soybean events per construct containing an exemplary mutant HPPD polypeptide were sprayed with the HPPD inhibitor herbicide Cmpd. 1 (2-chloro-3-(methylsulfanyl)-N-(1-methyl-1H-tetrazol-5-yl)-4-(trifluoromethyl)benzamide) at the rate of 300 grams AI/ha, supplemented with ammonium sulfate and methyl ester rapeseed oil. Five days after the application, the leaf damaged area due to the HPPD inhibitor herbicide is scored in a scale from 0 (no damage) to 100 (complete bleaching). Under those conditions, the wild-type plants were completely bleached and their damage scores were in the 95-100 range.

Table 9 presents the distribution of the HPPD inhibitor herbicide damage score data as percentile for exemplary mutant HPPD inhibitor herbicide tolerant polypeptides (SEQ ID NOs). The percentiles normalize ranks of the damage score from an individual plant in a population. The value of the 25th percentile is the damage score where 25% of the soybean events in the given population had a lower and 75% higher damage scores. The median is the 50th percentile. Half the values had higher damage scores; half had lower damage scores. The value of the 75th and 90th percentile is the damage score where 75% and 90% of the soybean events had lower damage scores, respectively. The difference between the 75th and 25th percentile is called the interquartile range and a marker to quantify scattering in the population. All constructs had only one single cassette insertion in the soybean genome.

In Table 9, the constructs were ranked based on injury scores according to the 75th percentile, from smallest to highest score. All exemplary HPPD polypeptide variants are better in all percentile analyses than the prior art mutant HPPD polypeptide (WO2014/043435) corresponding to SEQ ID NO:2 in this invention. The scoring of the prior art mutant HPPD polypeptide (WO2014/043435) corresponding to SEQ ID NO:2 in this invention is listed in the bottom row of Table 9.

TABLE 9

Evaluation of leaf area damage from transgenic soybean T0 events five days after the application of Cmpd. 1 at a rate of 300 g AI/ha by percentile distribution.

| T0 Soybean Events expressing polpypetide of | Total number independent events sprayed | 25th | Median | 75th | Interquartile range | 90th |
|---|---|---|---|---|---|---|
| SEQ ID NO: 9 | 21 | 10.0 | 10.0 | 15.0 | 5.0 | 19.0 |
| SEQ ID NO: 30 | 57 | 10.0 | 15.0 | 15.0 | 5.0 | 25.0 |
| SEQ ID NO: 22 | 50 | 10.0 | 10.0 | 15.0 | 5.0 | 34.5 |
| SEQ ID NO: 101 | 75 | 5.0 | 10.0 | 15.0 | 10.0 | 49.0 |
| SEQ ID NO: 105 | 58 | 5.0 | 10.0 | 15.0 | 10.0 | 70.0 |
| SEQ ID NO: 8 | 70 | 10.0 | 10.0 | 16.3 | 6.3 | 38.5 |
| SEQ ID NO: 24 | 56 | 10.0 | 10.0 | 20.0 | 10.0 | 35.0 |
| SEQ ID NO: 102 | 92 | 8.0 | 10.0 | 20.0 | 12.0 | 45.0 |
| SEQ ID NO: 54 | 44 | 10.0 | 10.0 | 20.0 | 10.0 | 62.5 |
| SEQ ID NO: 56 | 33 | 10.0 | 15.0 | 20.0 | 10.0 | 65.0 |
| SEQ ID NO: 43 | 27 | 10.0 | 15.0 | 20.0 | 10.0 | 67.0 |
| SEQ ID NO: 34 | 44 | 10.0 | 15.0 | 20.0 | 10.0 | 70.0 |
| SEQ ID NO: 5 | 55 | 10.0 | 15.0 | 20.0 | 10.0 | 72.0 |
| SEQ ID NO: 104 | 94 | 5.0 | 15.0 | 20.0 | 15.0 | 72.5 |
| SEQ ID NO: 42 | 59 | 10.0 | 15.0 | 20.0 | 10.0 | 75.0 |
| SEQ ID NO: 44 | 54 | 10.0 | 15.0 | 21.3 | 11.3 | 70.0 |
| SEQ ID NO: 21 | 59 | 10.0 | 15.0 | 25.0 | 15.0 | 35.0 |
| SEQ ID NO: 45 | 74 | 5.0 | 15.0 | 26.3 | 21.3 | 67.5 |
| SEQ ID NO: 2 | 75 | 15.0 | 20.0 | 45.0 | 30.0 | 87.0 |

Example 7: Cotton T0 Plant Establishment and Selection

Cotton transformation is achieved by using methods well known in the art, especially preferred method in the one described in the PCT patent publication WO 00/71733. Regenerated plants are transferred to the greenhouse. Following an acclimation period, sufficiently grown plants are sprayed with HPPD inhibitor herbicides as for example tembotrione equivalent to 100 or 200 gAI/ha supplemented with ammonium sulfate and methyl ester rapeseed oil. Seven days after the spray application, the symptoms due to the treatment with the HPPD inhibitor herbicide are evaluated and compared to the symptoms observed on wild-type cotton plants subjected to the same treatment under the same conditions.

Example 8: Transformation of Maize Plant Cells by *Agrobacterium*-Mediated Transformation Constructing the plant expression cassette for stable expression in the maize plant and maize transformation are well known in the art and in this particular example the methods were described and used from WO2014/043435 and WO2008/100353. The polynucleotide sequences encoding the mutant HPPD polypeptides in this application are stacked with a polynucleotide sequence encoding an EPSPS protein variant to confer tolerance to herbicides, which target the EPSPS. The EPSPS gene was isolated and mutated from *Arthrobacter globiformis* (WO2008/100353) and joined in-frame to a transit peptide sequence to guide translocation of the translated protein to the chloroplast.

Stable expression is achieved with a ubiquitous promoter (Ubiquitin 4 promoter from sugarcane, U.S. Pat. No. 6,638,766), and a 35S terminator sequence from Cauliflower Mosaic Virus, which is cloned upstream and downstream of the EPSPS gene, respectively.

The corresponding mutant HPPD polypeptide will be cloned with the same promoter, chloroplast transit peptide, and terminator sequence as described for the EPSPS gene expression cassette. The coding sequences for both genes are codon optimized for maize expression. For the maize transformation ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark.

However, it is not necessary per se to incubate the embryos overnight. Embryos are contacted with an *Agrobacterium* strain containing the appropriate vectors having a nucleotide sequence of the present invention for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media with glyphosate for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants. Plants are routinely analyzed for the expression and presence of the transgenes using the ELISA protein detection method. Only plants recovering in the selection media and having a detectable HPPD transgene protein expression are used for the herbicide tolerance analysis.

Example 9. Tolerance of T1 Soybean Plants to HPPD Inhibitor Herbicides/Field Trials Soybean plants expressing an HPPD inhibitor tolerant polypeptide of the present invention alone, or along with a gene conferring tolerance to glyphosate and/or a gene conferring tolerance to glufosinate or having a "plant expression cassette", which includes only an HPPD inhibitor tolerant polypeptide of the present invention, were tested for tolerance to different HPPD inhibitor herbicide chemical classes. The transgenic plants were routinely analyzed for the expression and presence of the transgenes using the ELISA protein detection method (see detailed description under item D and H). Only plants recovering in the selection media and having a detectable HPPD transgene protein expression were regenerated, transferred to the greenhouse and used at V2-V4 growth stage for the HPPD inhibitor herbicide tolerance analysis of the T0 soybean events in the greenhouse (Example 6). The chemical formulation with HPPD inhibitor herbicides was supplemented with ammonium sulfate and methyl ester rapeseed oil. Herbicide tolerance evaluation was taken 5-21 days after spraying. The best performing independent T0 soybean events were selfed to produce T1 soybean seeds. In the field trails, the advanced T1 soybean seeds were planted and treated with either 210 g/ha of isoxaflutole or 150 g/ha of Cmpd. 1 (2-chloro-3-(methylsulfanyl)-N-(1-methyl-1H-tetrazol-5-yl)-4-(trifluoromethyl) benzamide) at growth stage V2-V4 (Table 10) and leaf damage was scored eight days after the HPPD inhibitor herbicide application. All wild-type soybean plants or the segregated T1 soybean plants without the HPPD inhibitor tolerant polypeptide were sprayed with the same herbicide formulation and totally bleached and exhibited 100% leaf damage eight days after application.

In Table 10, the frequency of the soybean events showing a good tolerance, i.e. equal or less than 15% damage of the total leaf area are summarized All exemplary HPPD inhibitor herbicide tolerant polypeptide variants listed here had a higher frequency in the population with a good tolerance with equal or less than 15% leaf damage and therefore were better than the prior art mutant HPPD polypeptide (WO2014/043435) corresponding to SEQ ID NO:2 in this invention.

TABLE 10

Field trial evaluation of leaf area damage from exemplary transgenic T1 soybean events at stage growth V2-V4 expressing different HPPD polypeptide variants treated with either 210 g/ha of isoxaflutole (Table 10a) or 150 g/ha of Cmpd. 1 (Table 10b).

| T1 Soybean Events expressing HPPD polpypetide of | Total number independent events sprayed | Independent events with ≤15% leaf damage after spray | Frequency in the population |
|---|---|---|---|
| Table 10.a) Field trails of exemplary transgenic T1 soybean events sprayed with 210 g/ha of isoxaflutole and scored eight days after application: | | | |
| SEQ ID NO: 2 | 39 | 10 | 26% |
| SEQ ID NO: 16 | 20 | 19 | 95% |
| SEQ ID NO: 18 | 20 | 12 | 60% |
| SEQ ID NO: 31 | 14 | 13 | 93% |
| SEQ ID NO: 32 | 24 | 12 | 50% |
| SEQ ID NO: 96 | 20 | 11 | 55% |
| Table 10.b) Field trails of exemplary transgenic T1 soybean events sprayed with 150 g/ha of Cmpd. 1 and and scored eight days after application: | | | |
| SEQ ID NO: 2 | 39 | 16 | 41% |
| SEQ ID NO: 16 | 20 | 19 | 95% |
| SEQ ID NO: 18 | 20 | 12 | 60% |
| SEQ ID NO: 31 | 14 | 12 | 86% |
| SEQ ID NO: 32 | 24 | 10 | 42% |
| SEQ ID NO: 96 | 20 | 14 | 70% |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A recombinant nucleic acid molecule encoding a 4-hydroxyphenylpyruvate dioxygenase (HPPD) polypeptide, wherein said HPPD polypeptide comprises an amino acid sequence comprising (a) a proline at the amino acid position corresponding to amino acid position 335 of SEQ ID NO:1, (b) a histidine or an aspartic acid at the position corresponding to amino acid position 336 of SEQ ID NO:1, and (c) a serine at the position corresponding to amino acid position 337 of SEQ ID NO:1, and wherein said HPPD polypeptide is tolerant to one or more HPPD inhibitor herbicide(s).

2. The recombinant nucleic acid molecule of claim 1, wherein the amino acid sequence of said HPPD polypeptide further comprises:

i. a methionine, threonine, serine, or leucine at the amino acid position corresponding to amino acid position 204 of SEQ ID NO:1; and/or ii. a lysine or leucine at the amino acid position corresponding to amino acid position 213 of SEQ ID NO:1; and/or iii. an arginine, lysine, glutamine, or leucine at the amino acid position corresponding to amino acid position 264 of SEQ ID NO:1; and/or iv. an arginine, glycine, or serine at the amino acid position corresponding to amino acid position 268 of SEQ ID NO:1; and/or v. an arginine, leucine, glutamic acid, proline or serine at the amino acid position corresponding to amino acid position 270 of SEQ ID NO:1; and/or vi. a serine, histidine, or lysine at the amino acid position corresponding to amino acid position 310 of SEQ ID NO:1; and/or vii. an arginine, methionine or histidine at the amino acid position corresponding to amino acid position 315 of SEQ ID NO:1; and/or viii. a histidine, alanine, phenylalanine, valine, or glycine at the amino acid position corresponding to amino acid position 330 of SEQ ID NO:1; and/or ix. a proline, histidine, serine, isoleucine, or leucine at the amino acid position corresponding to amino acid position 331 of SEQ ID NO:1; and/or x. a valine at the amino acid position corresponding to amino acid position 338 of SEQ ID NO:1; and/or xi. a glutamic acid, arginine, alanine, or threonine at the amino acid position corresponding to amino acid position 339 of SEQ ID NO:1; and/or xii. an arginine, glutamine, methionine, glutamic acid, glycine, leucine, or valine at the amino acid position corresponding to amino acid position 340 of SEQ ID NO:1; and/or xiii. a glutamine, proline, or arginine at the amino acid position corresponding to amino acid position 344 of SEQ ID NO:1; and/or xiv. a lysine, arginine, methionine, alanine, or valine at the amino acid position corresponding to amino acid position 345 of SEQ ID NO:1.

3. The recombinant nucleic acid molecule of claim 1, wherein the amino acid sequence of said HPPD polypeptide further comprises:

i. a leucine or lysine at the amino acid position corresponding to amino acid position 213 of SEQ ID NO:1; and/or ii. an arginine or leucine at the amino acid position corresponding to amino acid position 264 of SEQ ID NO:1; and/or iii. an arginine, glycine or serine at the amino acid position corresponding to amino acid position 268 of SEQ ID NO:1; and/or iv. a glutamic acid or serine at the amino acid position corresponding to amino acid position 270 of SEQ ID NO:1; and/or v. an arginine or methionine at the amino acid position corresponding to amino acid position 315 of SEQ ID NO:1; and/or vi. a histidine at the amino acid position corresponding to amino acid position 330 of SEQ ID NO:1; and/or vii. a valine at the amino acid position corresponding to amino acid position 338 of SEQ ID NO:1; and/or viii. an arginine, or valine at the amino acid position corresponding to amino acid position 340 of SEQ ID NO:1; and/or ix. a glutamine at the amino acid position corresponding to amino acid position 344 of SEQ ID NO:1; and/or x. a lysine, valine, or methionine at the amino acid position corresponding to amino acid position 345 of SEQ ID NO:1.

4. The recombinant nucleic acid molecule of claim 1, wherein the amino acid sequence of said HPPD polypeptide further comprises:

i. a lysine at the amino acid position corresponding to amino acid position 213 of SEQ ID NO:1; and/or ii. an arginine or leucine at the amino acid position corresponding to amino acid position 264 of SEQ ID NO:1; and/or iii. a glycine or arginine at the amino acid position corresponding to amino acid position 268 of SEQ ID NO:1; and/or iv. a glutamic acid at the amino acid position corresponding to amino acid position 270 of SEQ ID NO:1; and/or v. an arginine at the amino acid position corresponding to amino acid position 315 of SEQ ID NO:1; and/or vi. a histidine at the amino acid position corresponding to amino acid position 330 of SEQ ID NO:1; and/or vii. a valine at the amino acid position corresponding to amino acid position 338 of SEQ ID NO:1; and/or viii. an arginine or valine at the amino acid position corresponding to amino acid position 340 of SEQ ID NO:1; and/or ix. a glutamine at the amino acid position corresponding to amino acid position 344 of SEQ ID NO:1; and/or x. a lysine, valine, or methionine at the amino acid position corresponding to amino acid position 345 of SEQ ID NO:1.

5. The recombinant nucleic acid molecule of claim 1, wherein said HPPD polypeptide comprises an amino acid sequence having at least 53% sequence identity to the amino acid sequence set forth in SEQ ID NO: 1.

6. The recombinant nucleic acid molecule of claim 5, wherein said HPPD polypeptide comprises an amino acid sequence having at least 90% sequence identity to the amino acid sequence set forth in SEQ ID NO: 1.

7. The recombinant nucleic acid molecule of claim 6, wherein said HPPD polypeptide comprises an amino acid sequence having at least 95% sequence identity to the amino acid sequence set forth in SEQ ID NO: 1.

8. The recombinant nucleic acid molecule of claim 1, wherein the recombinant nucleic acid molecule is a synthetic nucleic acid molecule that has been designed for expression in a plant.

9. The recombinant nucleic acid molecule of claim 1, wherein the recombinant nucleic acid molecule is operably linked to a promoter, wherein said promoter is capable of directing expression of the HPPD polypeptide in a plant cell.

10. The recombinant nucleic acid molecule of claim 1, wherein said HPPD inhibitor herbicide is selected from the group consisting of triketones, diketonitriles, isoxazoles, hydroxypyrazoles, N-(1,2,5-oxadiazol-3yl)benzamides, N-(1,3,4-oxadiazol-2-yl)benzamides, N-(tetrazol-5-yl)- or N-(triazol-5-yl)-arylcarboxamides, pyridazinone derivatives, oxoprazine derivatives, N-(triazol-2-yl)arylcarboxamides, triazinones, and pyrazolones.

11. The recombinant nucleic acid molecule of claim 10, wherein said HPPD inhibitor herbicide is selected from the group consisting of benzobicyclon, sulcotrione, mesotrione, tembotrione, tefuryltrione, bicyclopyrone, fenquinotrione, isoxaflutole, diketonitrile, pyrazoxyfen, benzofenap, pyrazolynate, pyrasulfotole, topramezone, tolpyralate, 2-methyl-N-(5-methyl-1,3,4-oxadiazol-2-yl)-3-(methylsulfonyl)-4-(trifluoromethyl)benzamide, 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide, 2-chloro-3-(methylsulfanyl)-N-(1-methyl-1H-tetrazol-5-yl)-4-(trifluoromethyl)benzamide, and 2-(methoxymethyl)-3-(methylsulfinyl)-N-(1-methyl-1H-tetrazol-5-yl)-4-(trifluoromethyl)benzamide.

12. A host cell comprising the recombinant nucleic acid molecule of claim 1.

13. The host cell of claim 12, wherein the host cell is a bacterial host cell.

14. The host cell of claim 12, wherein the host cell is a plant cell.

15. A method for producing a polypeptide with HPPD inhibitor herbicide tolerance activity, comprising culturing the host cell of claim 12 under conditions in which the HPPD polypeptide is expressed.

16. A transgenic plant comprising the recombinant nucleic acid molecule of claim 1.

17. The plant of claim 16, wherein said plant is selected from the group consisting of maize, sorghum, wheat, sunflower, tomato, crucifers, peppers, potato, cotton, rice, soybean, sugar beet, sugarcane, tobacco, barley, and oilseed rape.

18. A transgenic seed comprising the recombinant nucleic acid molecule of claim 1.

19. A plant or plant part comprising a stably incorporated DNA construct in the genome thereof, wherein said DNA construct comprises a promoter operably linked with the nucleic acid molecule of claim 1.

20. The plant part of claim 19, wherein said plant part is selected from the group consisting of a plant cell, a plant tissue, and a plant seed.

21. The plant or plant part of claim 19, wherein said plant is selected from the group consisting of maize, sorghum, wheat, sunflower, tomato, crucifers, peppers, potato, cotton, rice, soybean, sugar beet, sugarcane, tobacco, barley, and oilseed rape.

22. A method of controlling weeds in a field comprising planting the plant of claim 19 or a seed thereof in a field and applying to said field an effective concentration of an HPPD inhibitor herbicide, wherein the seed comprises the DNA construct.

23. The method of claim 22, wherein said HPPD inhibitor herbicide is selected from the group consisting of triketones, diketonitriles, isoxazoles, hydroxypyrazoles, N-(1,2,5-oxadiazol-3-yl)benzamides, N-(1,3,4-oxadiazol-2-yl)benzamides, N-(tetrazol-5-yl)- or N-(triazol-5-yl)-arylcarboxamides, pyridazinone derivatives, oxoprazine derivatives, N-(triazol-2-yl)arylcarboxamides, triazinones, and pyrazolones.

24. The method of claim 23, wherein said HPPD inhibitor herbicide is selected from the group consisting of benzobicyclon, sulcotrione, mesotrione, tembotrione, tefuryltrione, bicyclopyrone, fenquinotrione, isoxaflutole, diketonitrile, pyrazoxyfen, benzofenap, pyrazolynate, pyrasulfotole, topramezone, tolpyralate, 2-methyl-N-(5-methyl-1,3,4-oxadiazol-2-yl)-3-(methylsulfonyl)-4-(trifluoromethyl)benzamide, 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl) benzamide, 2-chloro-3-(methylsulfanyl)-N-(1-methyl-1H-tetrazol-5-yl)-4-(trifluoromethyl)benzamide, and 2-(methoxymethyl)-3-(methylsulfinyl)-N-(1-methyl-1H-tetrazol-5-yl)-4-(trifluoromethyl)benzamide.

25. Transgenic seed of a plant comprising a stably incorporated DNA construct in the genome thereof, said DNA construct comprising a promoter operably linked with the nucleic acid molecule of claim 1.

26. A product comprising a nucleic acid of claim 1 for rendering a plant tolerant to one or more HPPD inhibitor herbicide(s).

27. A commodity product comprising the nucleic acid molecule of claim 1, wherein said product is selected from the group consisting of whole or processed seeds or grain, animal feed, corn or soybean meal, corn or soybean flour, corn starch, soybean meal, soybean flour, flakes, soybean protein concentrate, soybean protein isolates, texturized soybean protein concentrate, cosmetics, hair care products, soybean nut butter, natto, tempeh, hydrolyzed soybean protein, whipped topping, shortening, lecithin, edible whole soybeans, soybean yogurt, soybean cheese, tofu, yuba, and cooked, polished, steamed, baked or parboiled grain.

28. A recombinant polypeptide comprising an HPPD polypeptide, wherein said HPPD polypeptide is tolerant to one or more HPPD inhibitor herbicide(s), and wherein said HPPD polypeptide comprises an amino acid sequence comprising (a) a proline at the amino acid position corresponding to amino acid position 335 of SEQ ID NO:1, (b) a histidine or an aspartic acid at the position corresponding to amino acid position 336 of SEQ ID NO:1, and (c) a serine at the position corresponding to amino acid position 337 of SEQ ID NO:1.

29. The recombinant polypeptide of claim 28, wherein the amino acid sequence of said HPPD polypeptide further comprises:

i. a methionine, threonine, serine, or leucine at the amino acid position corresponding to amino acid position 204 of SEQ ID NO:1; and/or ii. a lysine or leucine at the amino acid position corresponding to amino acid position 213 of SEQ ID NO:1; and/or iii. an arginine, lysine, glutamine, or leucine at the amino acid position corresponding to amino acid position 264 of SEQ ID NO:1; and/or iv. an arginine, glycine, or serine at the amino acid position corresponding to amino acid position 268 of SEQ ID NO:1; and/or v. an arginine, leucine, glutamic acid, proline or serine at the amino acid position corresponding to amino acid position 270 of SEQ ID NO:1; and/or vi. a serine, histidine, or lysine at the amino acid position corresponding to amino acid position 310 of SEQ ID NO:1; and/or vii. an arginine, methionine or histidine at the amino acid position corresponding to amino acid position 315 of SEQ ID NO:1; and/or viii. a histidine, alanine, phenylalanine, valine, or glycine at the amino acid position corresponding to amino acid position 330 of SEQ ID NO:1; and/or ix. a proline, histidine, serine, isoleucine, or leucine at the amino acid position corresponding to amino acid position 331 of SEQ ID NO:1; and/or x. a valine at the amino acid position corresponding to amino acid position 338 of SEQ ID NO:1; and/or xi. a glutamic acid, arginine, alanine, or threonine at the amino acid position corresponding to amino acid position 339 of SEQ ID NO:1; and/or xii. an arginine, glutamine, methionine, glutamic acid, glycine, leucine, or valine at the amino acid position corresponding to amino acid position 340 of SEQ ID NO:1; and/or xiii. a glutamine, proline, or arginine at the amino acid position corresponding to amino acid position 344 of SEQ ID NO:1; and/or xiv. a lysine, arginine, methionine, alanine, or valine at the amino acid position corresponding to amino acid position 345 of SEQ ID NO:1.

30. The recombinant polypeptide of claim 28, wherein the amino acid sequence of said HPPD polypeptide further comprises:

i. a leucine or lysine at the amino acid position corresponding to amino acid position 213 of SEQ ID NO:1; and/or ii. an arginine or leucine at the amino acid position corresponding to amino acid position 264 of SEQ ID NO:1; and/or iii. an arginine, glycine or serine at the amino acid position corresponding to amino acid position 268 of SEQ ID NO:1; and/or iv. a glutamic acid or serine at the amino acid position corresponding to amino acid position 270 of SEQ ID NO:1; and/or v. an arginine or methionine at the amino acid position corresponding to amino acid position 315 of SEQ ID NO:1; and/or vi. a histidine at the amino acid position corresponding to amino acid position 330 of SEQ ID NO:1; and/or vii. a valine at the amino acid position corresponding to amino acid position 338 of SEQ ID NO:1; and/or viii. an arginine, or valine at the amino acid position corresponding to amino acid position 340 of SEQ ID NO:1; and/or ix. a glutamine at the amino acid position corresponding to amino acid position 344 of SEQ ID NO:1; and/or x. a lysine, valine, or methionine at the amino acid position corresponding to amino acid position 345 of SEQ ID NO:1.

31. The recombinant polypeptide of claim 28, wherein the amino acid sequence of said HPPD polypeptide further comprises:

i. a lysine at the amino acid position corresponding to amino acid position 213 of SEQ ID NO:1; and/or ii. an arginine or leucine at the amino acid position corresponding to amino acid position 264 of SEQ ID NO:1; and/or iii. a glycine or arginine at the amino acid position corresponding to amino acid position 268 of SEQ ID NO:1; and/or iv. a glutamic acid at the amino acid position corresponding to amino acid position 270 of SEQ ID NO:1; and/or v. an arginine at the amino acid position corresponding to amino acid position 315 of SEQ ID NO:1; and/or vi. a histidine at the amino acid position corresponding to amino acid position 330 of SEQ ID NO:1; and/or vii. a valine at the amino acid position corresponding to amino acid position 338 of SEQ ID NO:1; and/or viii. an arginine or valine at the amino acid position corresponding to amino acid position 340 of SEQ ID NO:1; and/or ix. a glutamine at the amino acid position corresponding to amino acid position 344 of SEQ ID NO:1; and/or x. a lysine, valine, or methionine at the amino acid position corresponding to amino acid position 345 of SEQ ID NO:1.

32. The recombinant polypeptide of claim 28, wherein said HPPD polypeptide comprises an amino acid sequence having at least 53% sequence identity to the amino acid sequence set forth in SEQ ID NO:1.

33. The recombinant polypeptide of claim 32, wherein said HPPD polypeptide comprises an amino acid sequence having at least 90% sequence identity to the amino acid sequence set forth in SEQ ID NO:1.

34. The recombinant polypeptide of claim 33, wherein said HPPD polypeptide comprises an amino acid sequence having at least 95% sequence identity to the amino acid sequence set forth in SEQ ID NO:1.

35. The recombinant polypeptide of claim 28, wherein said HPPD inhibitor herbicide is selected from the group consisting of triketones, diketontriles, isoxazoles, hydroxypyrazoles, N-(1,2,5-oxadiazol-3-yl)benzamides, N-(1,3,4-oxadiazol-2-yl)benzamides, N-(tetrazol-5-yl)- or N-(triazol-5-yl)-arylcarboxamides, pyridazinone derivatives, oxoprazine derivatives, N-(triazol-2-yl)arylcarboxamides, triazinones, and pyrazolones.

36. The recombinant polypeptide of claim 35, wherein said HPPD inhibitor herbicide is selected from the group consisting of benzobicyclon, sulcotrione, mesotrione, tembotrione, tefuryltrione, bicyclopyrone, fenquinotrione, isoxaflutole, diketonitrile, pyrazoxyfen, benzofenap, pyrazolynate, pyrasulfotole, topramezone, tolpyralate, 2-methyl-N-(5-methyl-1,3,4-oxadiazol-2-yl)-3-(methylsulfonyl)-4-(trifluoromethyl)benzamide, 2-chloro-3-ethoxy-4-(methylsulfonyl)-N-(1-methyl-1H-tetrazol-5-yl)benzamide, 4-(difluoromethyl)-2-methoxy-3-(methylsulfonyl)-N-(1-methyl-1H-tetrazol-5-yl)benzamide, 2-chloro-3-(methylsulfanyl)-N-(1-methyl-1H-tetrazol-5-yl)-4-(trifluoromethyl) benzamide, and 2-(methoxymethyl)-3-(methylsulfinyl)-N-(1-methyl-1H-tetrazol-5-yl)-4-(trifluoromethyl)benzamide.

37. A recombinant polypeptide comprising an HPPD polypeptide, wherein said HPPD polypeptide is tolerant to one or more HPPD inhibitor herbicide(s), and wherein said HPPD polypeptide comprises an amino acid sequence comprising a glycine or arginine at the amino acid position corresponding to amino acid position 268 of SEQ ID NO:1, a glutamic acid at the amino acid position corresponding to amino acid position 270 of SEQ ID NO:1, a proline at the amino acid position corresponding to amino acid position 335 of SEQ ID NO:1, a histidine or an aspartic acid at the position corresponding to amino acid position 336 of SEQ ID NO:1, a serine at the position corresponding to amino acid position 337 of SEQ ID NO:1, a valine at the amino acid position corresponding to amino acid position 340 of SEQ ID NO:1; and a valine at the amino acid position corresponding to amino acid position 345 of SEQ ID NO:1.

* * * * *

SEQUENCE LISTING

```
<160> NUMBER OF SEQ ID NOS: 109

<210> SEQ ID NO 1
<211> LENGTH: 358
```

-continued

<212> TYPE: PRT
<213> ORGANISM: Pseudomonas fluorescens
<220> FEATURE:
<221> NAME/KEY: 4-hydroxyphenylpyruvate dioxygenase (HPPD; Pseudomonas fluorescens)
<222> LOCATION: (1)..(358)

<400> SEQUENCE: 1

Met Ala Asp Leu Tyr Glu Asn Pro Met Gly Leu Met Gly Phe Glu Phe
1 5 10 15

Ile Glu Phe Ala Ser Pro Thr Pro Gly Thr Leu Glu Pro Ile Phe Glu
20 25 30

Ile Met Gly Phe Thr Lys Val Ala Thr His Arg Ser Lys Asn Val His
35 40 45

Leu Tyr Arg Gln Gly Glu Ile Asn Leu Ile Leu Asn Asn Glu Pro Asn
50 55 60

Ser Ile Ala Ser Tyr Phe Ala Ala Glu His Gly Pro Ser Val Cys Gly
65 70 75 80

Met Ala Phe Arg Val Lys Asp Ser Gln Lys Ala Tyr Asn Arg Ala Leu
85 90 95

Glu Leu Gly Ala Gln Pro Ile His Ile Asp Thr Gly Pro Met Glu Leu
100 105 110

Asn Leu Pro Ala Ile Lys Gly Ile Gly Gly Ala Pro Leu Tyr Leu Ile
115 120 125

Asp Arg Phe Gly Glu Gly Ser Ser Ile Tyr Asp Ile Asp Phe Val Tyr
130 135 140

Leu Glu Gly Val Glu Arg Asn Pro Val Gly Ala Gly Leu Lys Val Ile
145 150 155 160

Asp His Leu Thr His Asn Val Tyr Arg Gly Arg Met Val Tyr Trp Ala
165 170 175

Asn Phe Tyr Glu Lys Leu Phe Asn Phe Arg Glu Ala Arg Tyr Phe Asp
180 185 190

Ile Lys Gly Glu Tyr Thr Gly Leu Thr Ser Lys Ala Met Ser Ala Pro
195 200 205

Asp Gly Met Ile Arg Ile Pro Leu Asn Glu Glu Ser Ser Lys Gly Ala
210 215 220

Gly Gln Ile Glu Glu Phe Leu Met Gln Phe Asn Gly Glu Gly Ile Gln
225 230 235 240

His Val Ala Phe Leu Thr Asp Asp Leu Val Lys Thr Trp Asp Ala Leu
245 250 255

Lys Lys Ile Gly Met Arg Phe Met Thr Ala Pro Pro Asp Thr Tyr Tyr
260 265 270

Glu Met Leu Glu Gly Arg Leu Pro Asp His Gly Glu Pro Val Asp Gln
275 280 285

Leu Gln Ala Arg Gly Ile Leu Leu Asp Gly Ser Ser Val Glu Gly Asp
290 295 300

Lys Arg Leu Leu Leu Gln Ile Phe Ser Glu Thr Leu Met Gly Pro Val
305 310 315 320

Phe Phe Glu Phe Ile Gln Arg Lys Gly Asp Asp Gly Phe Gly Glu Gly
325 330 335

Asn Phe Lys Ala Leu Phe Glu Ser Ile Glu Arg Asp Gln Val Arg Arg
340 345 350

Gly Val Leu Thr Ala Asp
355

-continued

<210> SEQ ID NO 2
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 2

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Ala Gln Leu Phe Glu Ser Ile Glu Arg Asp Gln Val Arg Arg
            340                 345                 350

Gly Val Leu Thr Ala Asp
        355
```

<210> SEQ ID NO 3
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 3

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Gly
                325                 330                 335

Asn Phe Lys Ala Leu Phe Glu Ser Ile Glu Arg Asp Gln Val Arg Arg
            340                 345                 350

Gly Val Leu Thr Ala Asp
        355
```

<210> SEQ ID NO 4
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 4

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Ser Phe Lys Ala Leu Phe Glu Ser Ile Glu Arg Asp Gln Val Arg Arg
            340                 345                 350

Gly Val Leu Thr Ala Asp
        355
```

<210> SEQ ID NO 5
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 5

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Gly
                325                 330                 335

Ser Phe Lys Ala Leu Phe Glu Ser Ile Glu Arg Asp Gln Val Arg Arg
            340                 345                 350

Gly Val Leu Thr Ala Asp
        355
```

<210> SEQ ID NO 6
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 6

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Asn Phe Lys Ala Leu Phe Glu Ser Ile Glu Arg Asp Gln Val Arg Arg
            340                 345                 350

Gly Val Leu Thr Ala Asp
        355
```

<210> SEQ ID NO 7
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 7

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Ala Leu Phe Glu Ser Ile Glu Arg Asp Gln Val Arg Arg
            340                 345                 350

Gly Val Leu Thr Ala Asp
        355
```

-continued

<210> SEQ ID NO 8
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 8

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Ile Glu Arg Asp Gln Val Arg Arg
            340                 345                 350

Gly Val Leu Thr Ala Asp
        355
```

-continued

<210> SEQ ID NO 9
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 9

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Ala Leu Phe Glu Ser Val Glu Arg Asp Gln Val Arg Arg
            340                 345                 350

Gly Val Leu Thr Ala Asp
        355
```

```
<210> SEQ ID NO 10
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 10

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 11
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 11

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Ala Leu Phe Glu Ser Ile Glu Arg Asp Gln Val Arg Arg
            340                 345                 350

Gly Val Leu Thr Ala Asp
        355
```

-continued

<210> SEQ ID NO 12
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 12

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Ile Glu Arg Asp Gln Val Arg Arg
            340                 345                 350

Gly Val Leu Thr Ala Asp
        355
```

<210> SEQ ID NO 13
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 13

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Ala Leu Phe Glu Ser Val Glu Arg Asp Gln Val Arg Arg
            340                 345                 350

Gly Val Leu Thr Ala Asp
        355
```

<210> SEQ ID NO 14
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 14

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

```
<210> SEQ ID NO 15
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 15

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Ser Asp Ser Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 16
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 16

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Ser Asp Ser Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Lys Glu Arg Asp Gln Val Arg Arg
            340                 345                 350

Gly Val Leu Thr Ala Asp
        355
```

```
<210> SEQ ID NO 17
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 17

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 18
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 18

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Ile Glu Arg Asp Gln Val Arg Arg
            340                 345                 350

Gly Val Leu Thr Ala Asp
        355
```

<210> SEQ ID NO 19
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 19

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

```
<210> SEQ ID NO 20
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 20

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Asn Phe Lys Ala Leu Phe Glu Ser Ile Glu Arg Asp Gln Val Arg Arg
            340                 345                 350

Gly Val Leu Thr Ala Asp
        355
```

<210> SEQ ID NO 21
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 21

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Ala Leu Phe Glu Ser Ile Glu Arg Asp Gln Val Arg Arg
            340                 345                 350

Gly Val Leu Thr Ala Asp
        355
```

-continued

```
<210> SEQ ID NO 22
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 22

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Ser Ile Glu Arg Asp Gln Val Arg Arg
            340                 345                 350

Gly Val Leu Thr Ala Asp
        355
```

-continued

<210> SEQ ID NO 23
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 23

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Ala Leu Phe Glu Ser Val Glu Arg Asp Gln Val Arg Arg
            340                 345                 350

Gly Val Leu Thr Ala Asp
        355
```

-continued

<210> SEQ ID NO 24
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 24

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 25
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 25

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro His
                325                 330                 335

Ser Phe Lys Ala Leu Phe Glu Ser Ile Glu Arg Asp Gln Val Arg Arg
            340                 345                 350

Gly Val Leu Thr Ala Asp
        355
```

```
<210> SEQ ID NO 26
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 26

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro His
                325                 330                 335

Ser Phe Lys Val Leu Phe Glu Ser Ile Glu Arg Asp Gln Val Arg Arg
            340                 345                 350

Gly Val Leu Thr Ala Asp
        355
```

-continued

<210> SEQ ID NO 27
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 27

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro His
                325                 330                 335

Ser Phe Lys Ala Leu Phe Glu Ser Val Glu Arg Asp Gln Val Arg Arg
            340                 345                 350

Gly Val Leu Thr Ala Asp
        355
```

-continued

<210> SEQ ID NO 28
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 28

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro His
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 29
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 29

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Ser Asp Ser Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 30
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 30

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Ser Asp Ser Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Ser Lys Glu Arg Asp Gln Val Arg Arg
            340                 345                 350

Gly Val Leu Thr Ala Asp
        355
```

-continued

<210> SEQ ID NO 31
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 31

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 32
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 32

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Arg Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 33
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 33

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Arg Leu Phe Glu Ser Val Glu Arg Asp Gln Val Arg Arg
            340                 345                 350

Gly Val Leu Thr Ala Asp
        355
```

<210> SEQ ID NO 34
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 34

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Arg Leu Phe Glu Ser Lys Glu Arg Asp Gln Val Arg Arg
            340                 345                 350

Gly Val Leu Thr Ala Asp
        355
```

<210> SEQ ID NO 35
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 35

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Arg Leu Phe Glu Ser Lys Glu Arg Asp Gln Val Arg Arg
            340                 345                 350

Gly Val Leu Thr Ala Asp
        355
```

<210> SEQ ID NO 36
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 36

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Met Glu Arg Asp Gln Val Arg Arg
            340                 345                 350

Gly Val Leu Thr Ala Asp
        355
```

-continued

<210> SEQ ID NO 37
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 37

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Arg Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Lys Glu Arg Asp Gln Val Arg Arg
            340                 345                 350

Gly Val Leu Thr Ala Asp
        355
```

<210> SEQ ID NO 38
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 38

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Val Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 39
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 39

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Leu Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 40
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 40

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Met Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 41
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 41

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ser Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 42
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 42

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Thr Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 43
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 43

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Lys Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 44
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 44

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Leu Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 45
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 45

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Arg Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 46
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 46

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Met Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 47
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 47

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu His Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 48
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 48

Met Ala Asp Leu Tyr Glu Asn Pro Met Gly Leu Met Gly Phe Glu Phe
1 5 10 15

Ile Glu Phe Ala Ser Pro Thr Pro Gly Thr Leu Glu Pro Ile Phe Glu
20 25 30

Ile Met Gly Phe Thr Lys Val Ala Thr His Arg Ser Lys Asn Val His
35 40 45

Leu Tyr Arg Gln Gly Glu Ile Asn Leu Ile Leu Asn Asn Glu Pro Asn
50 55 60

Ser Ile Ala Ser Tyr Phe Ala Ala Glu His Gly Pro Ser Val Cys Gly
65 70 75 80

Met Ala Phe Arg Val Lys Asp Ser Gln Lys Ala Tyr Asn Arg Ala Leu
85 90 95

Glu Leu Gly Ala Gln Pro Ile His Ile Asp Thr Gly Pro Met Glu Leu
100 105 110

Asn Leu Pro Ala Ile Lys Gly Ile Gly Gly Ala Pro Leu Tyr Leu Ile
115 120 125

Asp Arg Phe Gly Glu Gly Ser Ser Ile Tyr Asp Ile Asp Phe Val Tyr
130 135 140

Leu Glu Gly Val Glu Arg Asn Pro Val Gly Ala Gly Leu Lys Val Ile
145 150 155 160

Asp His Leu Thr His Asn Val Tyr Arg Gly Arg Met Val Tyr Trp Ala
165 170 175

Asn Phe Tyr Glu Lys Leu Phe Asn Phe Arg Glu Ala Arg Tyr Phe Asp
180 185 190

Ile Lys Gly Glu Tyr Thr Gly Leu Thr Ser Lys Ala Met Ser Ala Pro
195 200 205

Asp Gly Met Ile Arg Ile Pro Leu Asn Glu Glu Ser Ser Lys Gly Ala
210 215 220

Gly Gln Ile Glu Glu Phe Leu Met Gln Phe Asn Gly Glu Gly Ile Gln
225 230 235 240

His Val Ala Phe Leu Thr Asp Asp Leu Val Lys Thr Trp Asp Ala Leu
245 250 255

Lys Lys Ile Gly Met Arg Phe Met Thr Ala Pro Gly Asp Glu Tyr Tyr
260 265 270

Glu Met Leu Glu Gly Arg Leu Pro Asp His Gly Glu Pro Val Asp Gln
275 280 285

Leu Gln Ala Arg Gly Ile Leu Leu Asp Gly Ser Ser Val Glu Gly Asp
290 295 300

Lys Arg Leu Leu Leu Gln Ile Phe Ser Glu Thr Leu Met Gly Pro Val
305 310 315 320

Phe Phe Glu Phe Ile Gln Arg Lys Gly Asp His Gly Phe Gly Pro Asp
325 330 335

Ser Phe Lys Val Leu Phe Glu Ser Val Glu Arg Asp Gln Val Arg Arg
340 345 350

Gly Val Leu Thr Ala Asp
355

-continued

<210> SEQ ID NO 49
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 49

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Ile Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 50
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 50

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Pro Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 51
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 51

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Leu Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 52
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 52

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Ser Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 53
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 53

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Val Lys Val Leu Phe Glu Ser Val Glu Arg Asp Gln Val Arg Arg
            340                 345                 350

Gly Val Leu Thr Ala Asp
        355
```

<210> SEQ ID NO 54
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 54

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Ala Val Leu Phe Glu Ser Val Glu Arg Asp Gln Val Arg Arg
            340                 345                 350

Gly Val Leu Thr Ala Asp
        355
```

-continued

<210> SEQ ID NO 55
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 55

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Glu Val Leu Phe Glu Ser Val Glu Arg Asp Gln Val Arg Arg
            340                 345                 350

Gly Val Leu Thr Ala Asp
        355
```

<210> SEQ ID NO 56
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 56

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Arg Val Leu Phe Glu Ser Val Glu Arg Asp Gln Val Arg Arg
            340                 345                 350

Gly Val Leu Thr Ala Asp
        355
```

<210> SEQ ID NO 57
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 57

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Thr Val Leu Phe Glu Ser Val Glu Arg Asp Gln Val Arg Arg
            340                 345                 350

Gly Val Leu Thr Ala Asp
        355
```

-continued

<210> SEQ ID NO 58
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 58

Met Ala Asp Leu Tyr Glu Asn Pro Met Gly Leu Met Gly Phe Glu Phe
1 5 10 15

Ile Glu Phe Ala Ser Pro Thr Pro Gly Thr Leu Glu Pro Ile Phe Glu
20 25 30

Ile Met Gly Phe Thr Lys Val Ala Thr His Arg Ser Lys Asn Val His
35 40 45

Leu Tyr Arg Gln Gly Glu Ile Asn Leu Ile Leu Asn Asn Glu Pro Asn
50 55 60

Ser Ile Ala Ser Tyr Phe Ala Ala Glu His Gly Pro Ser Val Cys Gly
65 70 75 80

Met Ala Phe Arg Val Lys Asp Ser Gln Lys Ala Tyr Asn Arg Ala Leu
85 90 95

Glu Leu Gly Ala Gln Pro Ile His Ile Asp Thr Gly Pro Met Glu Leu
100 105 110

Asn Leu Pro Ala Ile Lys Gly Ile Gly Gly Ala Pro Leu Tyr Leu Ile
115 120 125

Asp Arg Phe Gly Glu Gly Ser Ser Ile Tyr Asp Ile Asp Phe Val Tyr
130 135 140

Leu Glu Gly Val Glu Arg Asn Pro Val Gly Ala Gly Leu Lys Val Ile
145 150 155 160

Asp His Leu Thr His Asn Val Tyr Arg Gly Arg Met Val Tyr Trp Ala
165 170 175

Asn Phe Tyr Glu Lys Leu Phe Asn Phe Arg Glu Ala Arg Tyr Phe Asp
180 185 190

Ile Lys Gly Glu Tyr Thr Gly Leu Thr Ser Lys Ala Met Ser Ala Pro
195 200 205

Asp Gly Met Ile Arg Ile Pro Leu Asn Glu Glu Ser Ser Lys Gly Ala
210 215 220

Gly Gln Ile Glu Glu Phe Leu Met Gln Phe Asn Gly Glu Gly Ile Gln
225 230 235 240

His Val Ala Phe Leu Thr Asp Asp Leu Val Lys Thr Trp Asp Ala Leu
245 250 255

Lys Lys Ile Gly Met Arg Phe Met Thr Ala Pro Gly Asp Glu Tyr Tyr
260 265 270

Glu Met Leu Glu Gly Arg Leu Pro Asp His Gly Glu Pro Val Asp Gln
275 280 285

Leu Gln Ala Arg Gly Ile Leu Leu Asp Gly Ser Ser Val Glu Gly Asp
290 295 300

Lys Arg Leu Leu Leu Gln Ile Phe Ser Glu Thr Leu Met Gly Pro Val
305 310 315 320

Phe Phe Glu Phe Ile Gln Arg Lys Gly Asp Asp Gly Phe Gly Pro Asp
325 330 335

Ser Phe Lys Val Leu Phe Glu Pro Val Glu Arg Asp Gln Val Arg Arg
340 345 350

Gly Val Leu Thr Ala Asp
355

-continued

<210> SEQ ID NO 59
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 59

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Arg Val Glu Arg Asp Gln Val Arg Arg
            340                 345                 350

Gly Val Leu Thr Ala Asp
        355
```

-continued

<210> SEQ ID NO 60
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 60

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Gln Val Glu Arg Asp Gln Val Arg Arg
            340                 345                 350

Gly Val Leu Thr Ala Asp
        355
```

<210> SEQ ID NO 61
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 61

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Pro Val Glu Arg Asp Gln Val Arg Arg
            340                 345                 350

Gly Val Leu Thr Ala Asp
        355
```

<210> SEQ ID NO 62
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 62

Met Ala Asp Leu Tyr Glu Asn Pro Met Gly Leu Met Gly Phe Glu Phe
1 5 10 15

Ile Glu Phe Ala Ser Pro Thr Pro Gly Thr Leu Glu Pro Ile Phe Glu
20 25 30

Ile Met Gly Phe Thr Lys Val Ala Thr His Arg Ser Lys Asn Val His
35 40 45

Leu Tyr Arg Gln Gly Glu Ile Asn Leu Ile Leu Asn Asn Glu Pro Asn
50 55 60

Ser Ile Ala Ser Tyr Phe Ala Ala Glu His Gly Pro Ser Val Cys Gly
65 70 75 80

Met Ala Phe Arg Val Lys Asp Ser Gln Lys Ala Tyr Asn Arg Ala Leu
85 90 95

Glu Leu Gly Ala Gln Pro Ile His Ile Asp Thr Gly Pro Met Glu Leu
100 105 110

Asn Leu Pro Ala Ile Lys Gly Ile Gly Gly Ala Pro Leu Tyr Leu Ile
115 120 125

Asp Arg Phe Gly Glu Gly Ser Ser Ile Tyr Asp Ile Asp Phe Val Tyr
130 135 140

Leu Glu Gly Val Glu Arg Asn Pro Val Gly Ala Gly Leu Lys Val Ile
145 150 155 160

Asp His Leu Thr His Asn Val Tyr Arg Gly Arg Met Val Tyr Trp Ala
165 170 175

Asn Phe Tyr Glu Lys Leu Phe Asn Phe Arg Glu Ala Arg Tyr Phe Asp
180 185 190

Ile Lys Gly Glu Tyr Thr Gly Leu Thr Ser Lys Ala Met Ser Ala Pro
195 200 205

Asp Gly Met Ile Arg Ile Pro Leu Asn Glu Glu Ser Ser Lys Gly Ala
210 215 220

Gly Gln Ile Glu Glu Phe Leu Met Gln Phe Asn Gly Glu Gly Ile Gln
225 230 235 240

His Val Ala Phe Leu Thr Asp Asp Leu Val Lys Thr Trp Asp Ala Leu
245 250 255

Lys Lys Ile Gly Met Arg Phe Arg Thr Ala Pro Gly Asp Glu Tyr Tyr
260 265 270

Glu Met Leu Glu Gly Arg Leu Pro Asp His Gly Glu Pro Val Asp Gln
275 280 285

Leu Gln Ala Arg Gly Ile Leu Leu Asp Gly Ser Ser Val Glu Gly Asp
290 295 300

Lys Arg Leu Leu Leu Gln Ile Phe Ser Glu Thr Leu Met Gly Pro Val
305 310 315 320

Phe Phe Glu Phe Ile Gln Arg Lys Gly His Asp Gly Phe Gly Pro Asp
325 330 335

Ser Phe Lys Val Leu Phe Glu Arg Val Glu Arg Asp Gln Val Arg Arg
340 345 350

Gly Val Leu Thr Ala Asp
355

-continued

<210> SEQ ID NO 63
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 63

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 64
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 64

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu His Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 65
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 65

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Lys Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 66
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 66

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Ser Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 67
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 67

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Lys Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 68
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 68

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Leu Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 69
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 69

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Gln Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 70
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 70

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 71
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 71

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 72
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 72

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Arg Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 73
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 73

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Ser Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 74
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 74

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Leu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 75
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 75

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Pro Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 76
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 76

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Arg Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 77
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 77

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Ser Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 78
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 78

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Ala Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 79
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 79

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Phe Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 80
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 80

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Gly Asp Gly Phe Gly Pro Asp
                325                 330                 335

Ser Phe Lys Val Leu Phe Glu Ser Val Glu Arg Asp Gln Val Arg Arg
            340                 345                 350

Gly Val Leu Thr Ala Asp
        355
```

<210> SEQ ID NO 81
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 81

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Ala Leu Phe Glu Ser Val Glu Arg Asp Gln Val Arg Arg
            340                 345                 350

Gly Val Leu Thr Ala Asp
        355
```

<210> SEQ ID NO 82
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 82

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Glu Leu Phe Glu Ser Val Glu Arg Asp Gln Val Arg Arg
            340                 345                 350

Gly Val Leu Thr Ala Asp
        355
```

<210> SEQ ID NO 83
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 83

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Gly Leu Phe Glu Ser Val Glu Arg Asp Gln Val Arg Arg
            340                 345                 350

Gly Val Leu Thr Ala Asp
        355
```

-continued

<210> SEQ ID NO 84
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 84

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Leu Leu Phe Glu Ser Val Glu Arg Asp Gln Val Arg Arg
            340                 345                 350

Gly Val Leu Thr Ala Asp
        355
```

<210> SEQ ID NO 85
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 85

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Met Leu Phe Glu Ser Val Glu Arg Asp Gln Val Arg Arg
            340                 345                 350

Gly Val Leu Thr Ala Asp
        355
```

-continued

<210> SEQ ID NO 86
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 86

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Gln Leu Phe Glu Ser Val Glu Arg Asp Gln Val Arg Arg
            340                 345                 350

Gly Val Leu Thr Ala Asp
        355
```

<210> SEQ ID NO 87
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 87

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Ala Glu Arg Asp Gln Val Arg Arg
            340                 345                 350

Gly Val Leu Thr Ala Asp
        355
```

<210> SEQ ID NO 88
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 88

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Ile Glu Arg Asp Gln Val Arg Arg
            340                 345                 350

Gly Val Leu Thr Ala Asp
        355
```

<210> SEQ ID NO 89
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 89

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Lys Glu Arg Asp Gln Val Arg Arg
            340                 345                 350

Gly Val Leu Thr Ala Asp
        355
```

-continued

<210> SEQ ID NO 90
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 90

Met Ala Asp Leu Tyr Glu Asn Pro Met Gly Leu Met Gly Phe Glu Phe
1 5 10 15

Ile Glu Phe Ala Ser Pro Thr Pro Gly Thr Leu Glu Pro Ile Phe Glu
20 25 30

Ile Met Gly Phe Thr Lys Val Ala Thr His Arg Ser Lys Asn Val His
35 40 45

Leu Tyr Arg Gln Gly Glu Ile Asn Leu Ile Leu Asn Asn Glu Pro Asn
50 55 60

Ser Ile Ala Ser Tyr Phe Ala Ala Glu His Gly Pro Ser Val Cys Gly
65 70 75 80

Met Ala Phe Arg Val Lys Asp Ser Gln Lys Ala Tyr Asn Arg Ala Leu
85 90 95

Glu Leu Gly Ala Gln Pro Ile His Ile Asp Thr Gly Pro Met Glu Leu
100 105 110

Asn Leu Pro Ala Ile Lys Gly Ile Gly Gly Ala Pro Leu Tyr Leu Ile
115 120 125

Asp Arg Phe Gly Glu Gly Ser Ser Ile Tyr Asp Ile Asp Phe Val Tyr
130 135 140

Leu Glu Gly Val Glu Arg Asn Pro Val Gly Ala Gly Leu Lys Val Ile
145 150 155 160

Asp His Leu Thr His Asn Val Tyr Arg Gly Arg Met Val Tyr Trp Ala
165 170 175

Asn Phe Tyr Glu Lys Leu Phe Asn Phe Arg Glu Ala Arg Tyr Phe Asp
180 185 190

Ile Lys Gly Glu Tyr Thr Gly Leu Thr Ser Lys Ala Met Ser Ala Pro
195 200 205

Asp Gly Met Ile Arg Ile Pro Leu Asn Glu Glu Ser Ser Lys Gly Ala
210 215 220

Gly Gln Ile Glu Glu Phe Leu Met Gln Phe Asn Gly Glu Gly Ile Gln
225 230 235 240

His Val Ala Phe Leu Thr Asp Asp Leu Val Lys Thr Trp Asp Ala Leu
245 250 255

Lys Lys Ile Gly Met Arg Phe Met Thr Ala Pro Gly Asp Glu Tyr Tyr
260 265 270

Glu Met Leu Glu Gly Arg Leu Pro Asp His Gly Glu Pro Val Asp Gln
275 280 285

Leu Gln Ala Arg Gly Ile Leu Leu Asp Gly Ser Ser Val Glu Gly Asp
290 295 300

Lys Arg Leu Leu Leu Gln Ile Phe Ser Glu Thr Leu Met Gly Pro Val
305 310 315 320

Phe Phe Glu Phe Ile Gln Arg Lys Gly Asp Asp Gly Phe Gly Pro Asp
325 330 335

Ser Phe Lys Val Leu Phe Glu Ser Met Glu Arg Asp Gln Val Arg Arg
340 345 350

Gly Val Leu Thr Ala Asp
355

```
<210> SEQ ID NO 91
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 91

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Ser Arg Glu Arg Asp Gln Val Arg Arg
            340                 345                 350

Gly Val Leu Thr Ala Asp
        355
```

-continued

<210> SEQ ID NO 92
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 92

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Ala Glu Arg Asp Gln Val Arg Arg
            340                 345                 350

Gly Val Leu Thr Ala Asp
        355
```

<210> SEQ ID NO 93
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 93

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Ile Glu Arg Asp Gln Val Arg Arg
            340                 345                 350

Gly Val Leu Thr Ala Asp
        355
```

<210> SEQ ID NO 94
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 94

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Lys Glu Arg Asp Gln Val Arg Arg
            340                 345                 350

Gly Val Leu Thr Ala Asp
        355
```

<210> SEQ ID NO 95
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 95

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Arg Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Arg Glu Arg Asp Gln Val Arg Arg
            340                 345                 350

Gly Val Leu Thr Ala Asp
        355
```

<210> SEQ ID NO 96
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 96

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Lys Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Ser Val Glu Arg Asp Gln Val Arg Arg
            340                 345                 350

Gly Val Leu Thr Ala Asp
        355
```

-continued

<210> SEQ ID NO 97
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 97

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Arg Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Ser Gly Phe Gly Pro Asp
                325                 330                 335

Ser Phe Lys Val Leu Phe Glu Ser Lys Glu Arg Asp Gln Val Arg Arg
            340                 345                 350

Gly Val Leu Thr Ala Asp
        355
```

<210> SEQ ID NO 98
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 98

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Ser Gly Phe Gly Pro Asp
                325                 330                 335

Ser Phe Lys Arg Leu Phe Glu Ser Lys Glu Arg Asp Gln Val Arg Arg
            340                 345                 350

Gly Val Leu Thr Ala Asp
        355
```

-continued

<210> SEQ ID NO 99
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 99

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Asp
                325                 330                 335

Ser Val Lys Arg Leu Phe Glu Ser Val Glu Arg Asp Gln Val Arg Arg
            340                 345                 350

Gly Val Leu Thr Ala Asp
        355
```

<210> SEQ ID NO 100
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 100

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Leu Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Gln Met Glu Arg Asp Gln Val Arg Arg
            340                 345                 350

Gly Val Leu Thr Ala Asp
        355
```

<210> SEQ ID NO 101
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 101

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Leu Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Arg Leu Met Gly Pro Val
305                 310                 315                 320

Phe Phe Glu Phe Ile Gln Arg Lys Gly Asp Asp Gly Phe Gly Pro Asp
                325                 330                 335

Ser Phe Lys Val Leu Phe Glu Gln Met Glu Arg Asp Gln Val Arg Arg
            340                 345                 350

Gly Val Leu Thr Ala Asp
        355
```

```
<210> SEQ ID NO 102
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 102

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Leu Thr Ala Pro Arg Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Arg Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Gln Met Glu Arg Asp Gln Val Arg Arg
            340                 345                 350

Gly Val Leu Thr Ala Asp
        355
```

<210> SEQ ID NO 103
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 103

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Lys Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Leu Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Arg Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Gln Met Glu Arg Asp Gln Val Arg Arg
            340                 345                 350

Gly Val Leu Thr Ala Asp
        355
```

<210> SEQ ID NO 104
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 104

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Lys Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Leu Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Val Leu Phe Glu Gln Met Glu Arg Asp Gln Val Arg Arg
            340                 345                 350

Gly Val Leu Thr Ala Asp
        355
```

-continued

<210> SEQ ID NO 105
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 105

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Lys Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Leu Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Phe Lys Arg Leu Phe Glu Gln Met Glu Arg Asp Gln Val Arg Arg
            340                 345                 350

Gly Val Leu Thr Ala Asp
        355
```

```
<210> SEQ ID NO 106
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 106

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Leu Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly His Pro Gly Phe Gly Pro Asp
                325                 330                 335

Ser Phe Lys Val Leu Phe Glu Gln Met Glu Arg Asp Gln Val Arg Arg
            340                 345                 350

Gly Val Leu Thr Ala Asp
        355
```

<210> SEQ ID NO 107
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 107

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Lys Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro His
                325                 330                 335

Ser Val Lys Arg Leu Phe Glu Ser Val Glu Arg Asp Gln Val Arg Arg
            340                 345                 350

Gly Val Leu Thr Ala Asp
        355
```

-continued

<210> SEQ ID NO 108
<211> LENGTH: 358
<212> TYPE: PRT
<213> ORGANISM: Artificial Sequence
<220> FEATURE:
<223> OTHER INFORMATION: mutant HPPD polypeptide

<400> SEQUENCE: 108

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Gly Asp Glu Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Met Leu Met Gly Pro Val
305                 310                 315                 320

Phe Phe Glu Phe Ile Gln Arg Lys Gly His Asp Gly Phe Gly Pro Asp
                325                 330                 335

Ser Phe Lys Val Leu Phe Glu Ser Met Glu Arg Asp Gln Val Arg Arg
            340                 345                 350

Gly Val Leu Thr Ala Asp
        355
```

-continued

```
<210> SEQ ID NO 109
<211> LENGTH: 1074
<212> TYPE: DNA
<213> ORGANISM: Pseudomonas fluorescens
<220> FEATURE:
<221> NAME/KEY: CDS 4-hydroxyphenylpyruvate dioxygenase (HPPD)
<222> LOCATION: (1)..(1074)

<400> SEQUENCE: 109

atggcagatc tatacgaaaa cccaatgggc ctgatgggct ttgaattcat cgaattcgcg     60

tcgccgacgc cgggtaccct ggagccgatc ttcgagatca tgggcttcac caaagtcgcg    120

acccaccgtt ccaagaacgt gcacctgtac cgccagggcg agatcaacct gatcctcaac    180

aacgagccca acagcatcgc ctcctacttt gcggccgaac acggcccgtc ggtgtgcggc    240

atggcgttcc gcgtgaagga ctcgcaaaag gcctacaacc gcgccctgga actcggcgcc    300

cagccgatcc atattgacac cgggccgatg gaattgaacc tgccggcgat caagggcatc    360

ggcggcgcgc cgttgtacct gatcgaccgt ttcggcgaag gcagctcgat ctacgacatc    420

gacttcgtgt acctcgaagg tgtggagcgc aatccggtcg gtgcaggtct caaagtcatc    480

gaccacctga cccacaacgt ctatcgcggc cgcatggtct actgggccaa cttctacgag    540

aaattgttca acttccgtga agcgcgttac ttcgatatca agggcgagta caccggcctg    600

acttccaagg ccatgagtgc gccggacggc atgatccgca tcccgctgaa cgaagagtcg    660

tccaagggcg cggggcagat cgaagagttc ctgatgcagt tcaacggcga aggcatccag    720

cacgtggcgt tcctcaccga cgacctggtc aagacctggg acgcgttgaa gaaaatcggc    780

atgcgcttca tgaccgcgcc gccagacact tattacgaaa tgctcgaagg ccgcctgcct    840

gaccacggcg agccggtgga tcaactgcag gcacgcggta tcctgctgga cggatcttcc    900

gtggaaggcg acaaacgcct gctgctgcag atcttctcgg aaaccctgat gggcccggtg    960

ttcttcgaat tcatccagcg caagggcgac gatgggtttg gcgaggggaa cttcaaggcg   1020

ctgttcgagt ccatcgaacg tgaccaggtg cgtcgtggtg tattgaccgc cgat         1074
```